US012046347B2

(12) United States Patent
Burroughs et al.

(10) Patent No.: US 12,046,347 B2
(45) Date of Patent: Jul. 23, 2024

(54) SELECTING AND CORRELATING PHYSICAL ACTIVITY DATA WITH IMAGE DATA

(71) Applicant: NIKE, Inc., Beaverton, OR (US)

(72) Inventors: Brandon S. Burroughs, Portland, OR (US); Richard J. Engelberg, Portland, OR (US); Jordan M. Rice, Portland, OR (US); Bob Sweet, Beaverton, OR (US); Aaron B. Weast, Portland, OR (US); Wade Convay, New York, NY (US); Joshua Rooke-Ley, New York, NY (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 17/495,071

(22) Filed: Oct. 6, 2021

(65) Prior Publication Data

US 2022/0028521 A1    Jan. 27, 2022

Related U.S. Application Data

(63) Continuation of application No. 16/232,628, filed on Dec. 26, 2018, now Pat. No. 11,170,885, which is a
(Continued)

(51) Int. Cl.
*G16H 20/30* (2018.01)
*A63B 24/00* (2006.01)
(Continued)

(52) U.S. Cl.
CPC ......... *G16H 20/30* (2018.01); *A63B 24/0062* (2013.01); *A63B 71/0622* (2013.01);
(Continued)

(58) Field of Classification Search
None
See application file for complete search history.

(56) References Cited

U.S. PATENT DOCUMENTS

| 5,419,562 A | 5/1995 | Cromarty |
|---|---|---|
| 6,148,262 A | 11/2000 | Fry |

(Continued)

FOREIGN PATENT DOCUMENTS

| CN | 1139388 A | 1/1997 |
|---|---|---|
| CN | 101202994 A | 6/2008 |

(Continued)

OTHER PUBLICATIONS

Zhang et al. "Interpolation calculation made EZ." 14th Annual Conference Proceedings, NorthEast SAS Users Group NESUG, Baltimore, MD. 2001 (Year: 2001).*

(Continued)

*Primary Examiner* — Saptarshi Mazumder
(74) *Attorney, Agent, or Firm* — Banner & Witcoff, Ltd.

(57) ABSTRACT

Example embodiments may relate systems, methods, apparatuses, and computer readable media configured to correlate image data of a user performing physical activity with data collected during the user's performance. Data may include sensor data measuring, force, acceleration, speed, and/or processed sensor data from one or more sensors. Certain embodiments may determine whether the user is within a performance zone based on user attributes. Correlation of the image data with physical activity data may be based, at least in part, whether the user is within a performance zone.

20 Claims, 42 Drawing Sheets

Related U.S. Application Data continuation of application No. 15/197,014, filed on Jun. 29, 2016, now Pat. No. 10,179,263, which is a continuation of application No. 13/399,452, filed on Feb. 17, 2012, now Pat. No. 9,411,940.

(60) Provisional application No. 61/443,808, filed on Feb. 17, 2011.

(51) Int. Cl.
  *A63B 71/06* (2006.01)
  *G09B 19/00* (2006.01)
  *G09G 5/14* (2006.01)
  *G16Z 99/00* (2019.01)
  *H04N 7/18* (2006.01)
  *A63B 43/00* (2006.01)
  *A63B 43/06* (2006.01)

(52) U.S. Cl.
  CPC ........... *G09B 19/0038* (2013.01); *G09G 5/14* (2013.01); *G16Z 99/00* (2019.02); *H04N 7/183* (2013.01); *A63B 43/00* (2013.01); *A63B 43/06* (2013.01); *A63B 2225/50* (2013.01); *G09G 2340/10* (2013.01)

(56) References Cited

U.S. PATENT DOCUMENTS

| | | | |
|---|---|---|---|
| 6,226,577 | B1 | 5/2001 | Yeo |
| 6,430,997 | B1 | 8/2002 | French et al. |
| 6,876,947 | B1 | 4/2005 | Darley et al. |
| 7,030,861 | B1 | 4/2006 | Westerman et al. |
| 7,739,076 | B1* | 6/2010 | Vock .................. A63B 71/0622 702/182 |
| 2001/0054043 | A1 | 12/2001 | Harlan |
| 2003/0208335 | A1 | 11/2003 | Unuma et al. |
| 2004/0100566 | A1* | 5/2004 | Valleriano .............. H04N 5/772 386/E5.072 |
| 2004/0215413 | A1* | 10/2004 | Weldum ............. H04N 1/32128 702/85 |
| 2007/0011919 | A1* | 1/2007 | Case .................... A43B 1/0036 36/132 |
| 2007/0072156 | A1* | 3/2007 | Kaufman ................ G16H 20/60 434/236 |
| 2007/0232455 | A1 | 10/2007 | Hanoun |
| 2007/0239562 | A1 | 10/2007 | Lawson |
| 2008/0140444 | A1 | 6/2008 | Karkanias et al. |
| 2008/0291272 | A1 | 11/2008 | Krahnstoever et al. |
| 2008/0297608 | A1 | 12/2008 | Border et al. |
| 2009/0076765 | A1 | 3/2009 | Kulach et al. |
| 2009/0099924 | A1 | 4/2009 | Lensch et al. |
| 2009/0126818 | A1 | 5/2009 | Zeloof et al. |
| 2009/0129402 | A1 | 5/2009 | Moller et al. |
| 2009/0171614 | A1 | 7/2009 | Damen |
| 2009/0235739 | A1 | 9/2009 | Morris Bamberg et al. |
| 2010/0023531 | A1 | 1/2010 | Brisebois et al. |
| 2010/0065886 | A1 | 3/2010 | Kamata et al. |
| 2010/0120584 | A1 | 5/2010 | Oshima et al. |
| 2010/0126825 | A1 | 5/2010 | Nieminen et al. |
| 2010/0184563 | A1* | 7/2010 | Molyneux ............ A43B 1/0054 473/570 |
| 2010/0259407 | A1 | 10/2010 | Tilvis et al. |
| 2010/0286601 | A1 | 11/2010 | Yodfat et al. |
| 2011/0003665 | A1 | 1/2011 | Burton et al. |
| 2011/0107369 | A1* | 5/2011 | O'Brien ................ G06F 16/435 725/38 |
| 2011/0298301 | A1 | 12/2011 | Wong et al. |
| 2012/0116684 | A1* | 5/2012 | Ingrassia, Jr. .......... G16H 10/60 702/19 |

FOREIGN PATENT DOCUMENTS

| | | |
|---|---|---|
| CN | 101454812 A | 6/2009 |
| CN | 101583403 A | 11/2009 |
| CN | 101599179 A | 12/2009 |
| CN | 101616718 A | 12/2009 |
| CN | 101636711 A | 1/2010 |
| CN | 101822895 A | 9/2010 |
| CN | 101853133 A | 10/2010 |
| CN | 101909705 A | 12/2010 |
| CN | 101918950 A | 12/2010 |
| CN | 102015037 A | 4/2011 |
| CN | 102218214 A | 10/2011 |
| CN | 102341194 A | 2/2012 |
| CN | 102481478 A | 5/2012 |
| EP | 2189191 A2 | 5/2010 |
| JP | H08-076926 A | 3/1996 |
| JP | H08-126632 A | 5/1996 |
| JP | H11-178967 A | 7/1999 |
| JP | 2000005368 A | 1/2000 |
| JP | 2001523140 A | 11/2001 |
| JP | 2002163404 A | 6/2002 |
| JP | 2002177432 A | 6/2002 |
| JP | 2006308346 A | 11/2006 |
| JP | 2007054450 A | 3/2007 |
| JP | 2008048757 A | 3/2008 |
| JP | 2008084158 A | 4/2008 |
| JP | 20083752 A | 10/2008 |
| JP | 2009148338 A | 7/2009 |
| JP | 2009525538 A | 7/2009 |
| JP | 2010502368 A | 1/2010 |
| JP | 2010192012 A | 9/2010 |
| JP | 2012510873 A | 5/2012 |
| JP | 2014511528 A | 5/2014 |
| JP | 6-142087 B2 | 6/2017 |
| KR | 20060053976 A | 5/2006 |
| KR | 20070033396 A | 3/2007 |
| KR | 20070051323 A | 5/2007 |
| KR | 100819205 B1 | 4/2008 |
| KR | 100892665 B1 | 4/2009 |
| KR | 20100089177 A | 8/2010 |
| WO | 2009027917 A1 | 3/2009 |
| WO | 2009126818 A2 | 10/2009 |
| WO | 2009152456 A2 | 12/2009 |
| WO | 2010065836 A2 | 6/2010 |
| WO | 2010126825 A1 | 11/2010 |

OTHER PUBLICATIONS

Zhang et al. "Interpolation calculation made EZ," 14th Annual Conference Proceedings, NorthEast SAS Users Group NESUG, Baltimore, MD, 2001.

Jun. 6, 2012—International Search Report from International Application No. PCT/US2012/025664 mailed Jun. 6, 2012, 4 pages.

Jun. 29, 2012—International Search Report from International Application No. PCT/US2012/025701, 4 pages.

United States Patent and Trademark Office, "Non-Final Office Action," issued in connection with U.S. Appl. No. 13/399,562, mailed Jul. 17, 2013, 13 pages.

International Bureau, "International Preliminary Report on Patentability," issued in connection with international application serial No. PCT/US2012/025664, mailed Aug. 29, 2013, 6 pages.

PCT/US2012/025667 International Search Report dated Jul. 20, 2012 (5 pages).

United States Patent and Trademark Office, "Non-Final Office Action," issued in connection with U.S. Appl. No. 13/399,555, mailed Dec. 13, 2013, 8 pages.

Jul. 31, 2012 (WO) International Search Report and Written Opinion—App PCT/US2012/025667, 3 pages.

Making a chart with dynamic range of values Posted on Oct. 15, 2009, in Charts and Graphs, Excel Howtos << https://chandoo.org/wp/2009/10/15/dynamic-chart-data-series/>>, by Chandoo.org, 17 pages.

Oct. 9, 2012 (EP) Communication pursuant to Article 94(3) EPC—App 09763744.1 (5 pages).

Dec. 7, 2012 (US) Office Action—U.S. Appl. No. 12/483,828 (24 pages).

Dec. 7, 2012 (US) Office Action—U.S. Appl. No. 12/483,824 (14 pages).

(56) References Cited

OTHER PUBLICATIONS

"Daphne (Carrefour shop at Zhongguancun)", by Meiweizi, www.dianping.com/photos/2847055#single-img, Oct. 5, 2009, 1 page.
"Statement in Accordance with the Notice from the European Patent Office Dated Oct. 1, 2007 concerning business methods—PCT/Erklaerung Gemaess der Mitteilung des Europaeischen Patentamts Vom 1.Oktober 2007 ueber geschaeftsmethoden—PCT/Declaration Conformement Au Communique de l'office Europ", Nov. 1, 2007.
EPO: "Mitteilung des Europaischen Patentamts vom 1. Oktober 2007 uber Geschaftsmethoden = Notice from the European Patent Office dated Oct. 1, 2007 concerning business methods = Communique de l'Office europeen des brevets, en date du 1er octobre 2007, concernant les methodes dans le domaine des activites", Journal Officiel de L'Office Europeen des Brevets. Official Journal of the European Patent Office, Amtsblattt des Europaeischen Patentamts, OEB, Munchen, DE, vol. 30, No. 11, Nov. 1, 2007, pp. 592-593.

\* cited by examiner

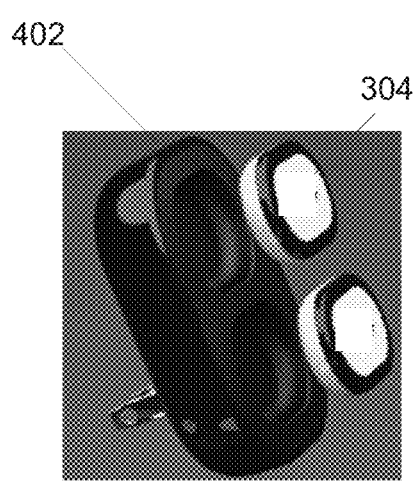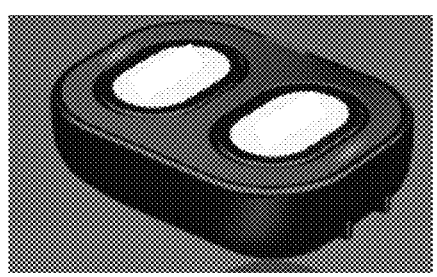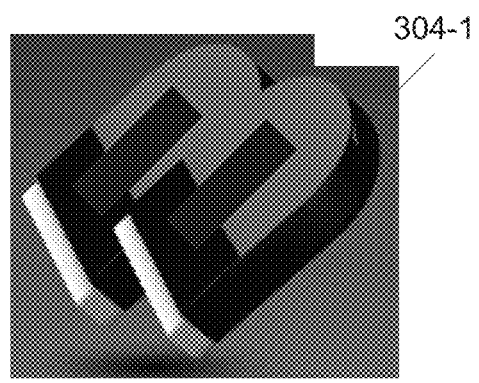
FIG. 4A  FIG. 4B

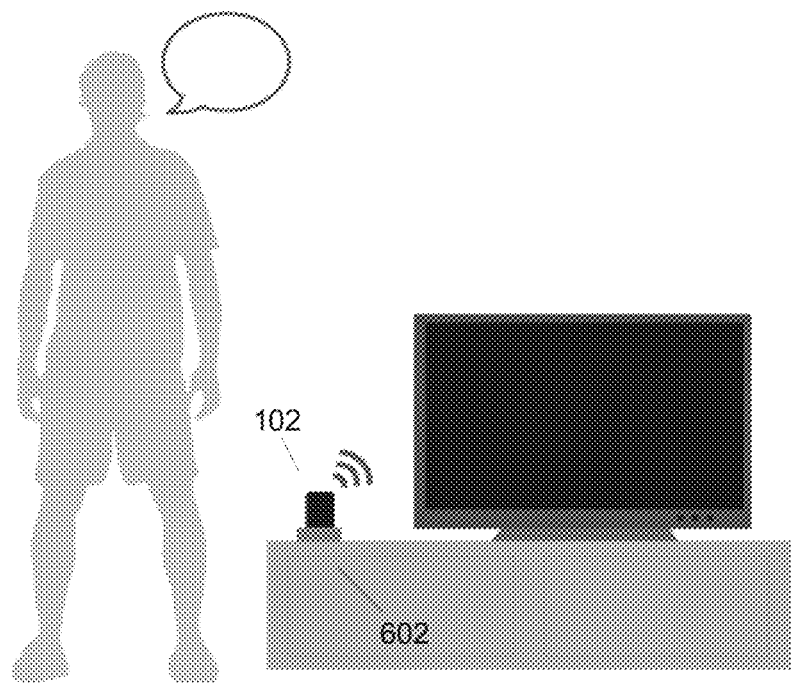
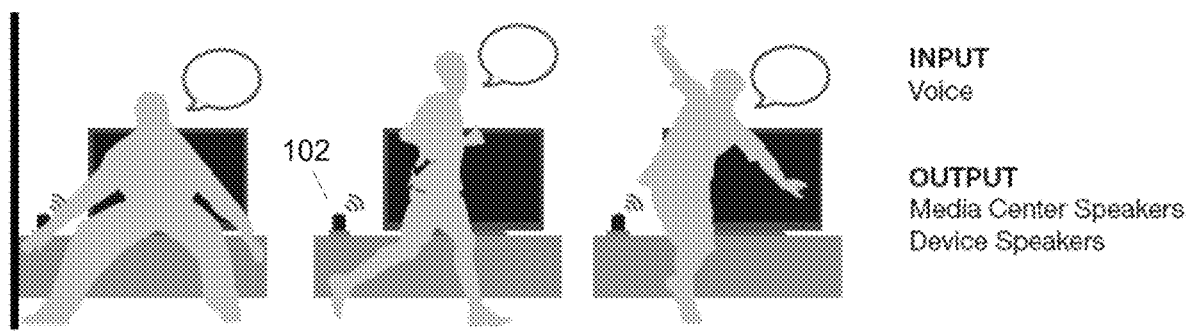
FIG. 6

| | | |
|---|---|---|
| ⌚ TOTAL PLAY TIME | 48 | MINUTES |
| ⊙ Total Activity Points | 932 | POINTS |
| ⊙ Activity Points Rate | 48 | PTS/MIN |
| 👟 HUSTLE | ▇ | HIGH |
| 📱 TOP VERTICAL | 26 | INCHES |
| 📱 AVERAGE VERTICAL | 8 | INCHES |
| 📱 TOTAL VERTICAL | 120 | FEET |
| ✈ TOP AIR TIME | 1.2 | SECONDS |
| ✈ AVERAGE AIR TIME | 0.4 | SECONDS |
| ✈ TOTAL AIR TIME | 42 | SECONDS |

| | | |
|---|---|---|
| ⚡ QUICKNESS | 45 | STEPS/SEC |
| ▬ DISTANCE | 3.2 | MILES |
| ⚡ MOST POWER | 89 | WATTS |
| ⚡ AVERAGE POWER | 33 | WATTS |
| ⚡ TOTAL POWER | 542 | WATTS |
| ⬥ BALANCE | 71 | ON TOES |
| ⬥ BALANCE | 👣 | FRONT |
| ⚽ PLAY STYLE | ▇ | AGGRESSIVE |
| ♥ ENDURANCE | ▇ | HIGH |
| ♥ TOTAL CALORIES | 345 | CALORIES |

FIG. 9

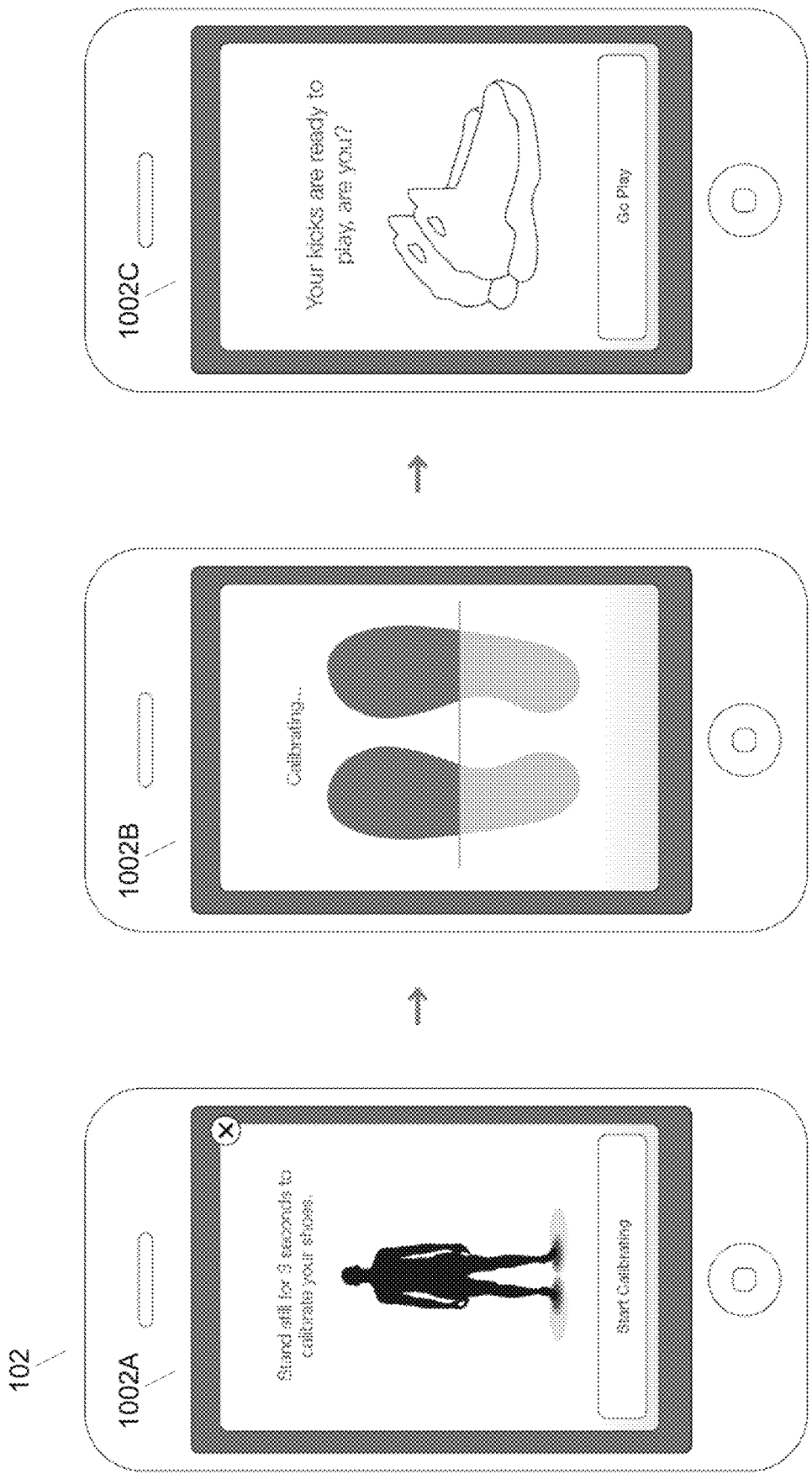

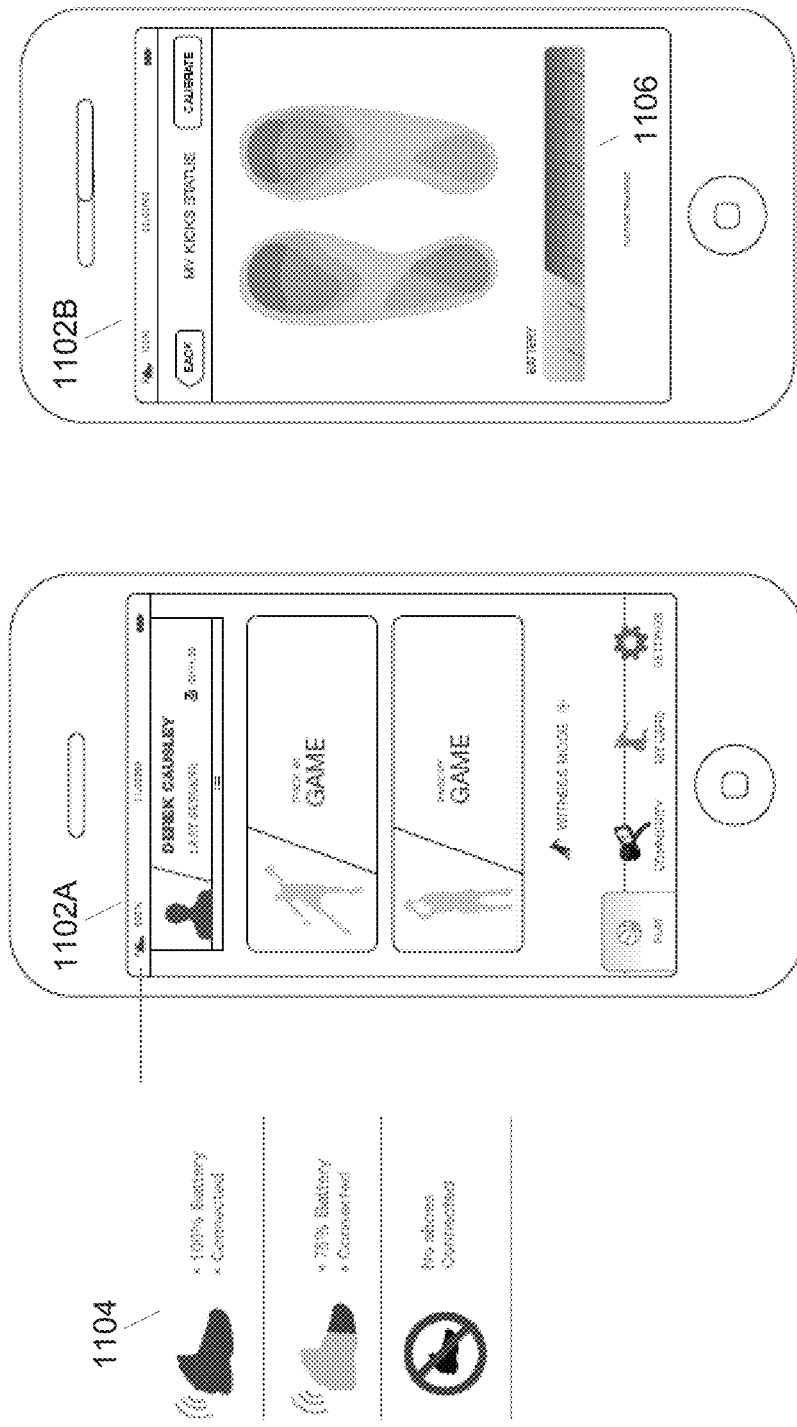

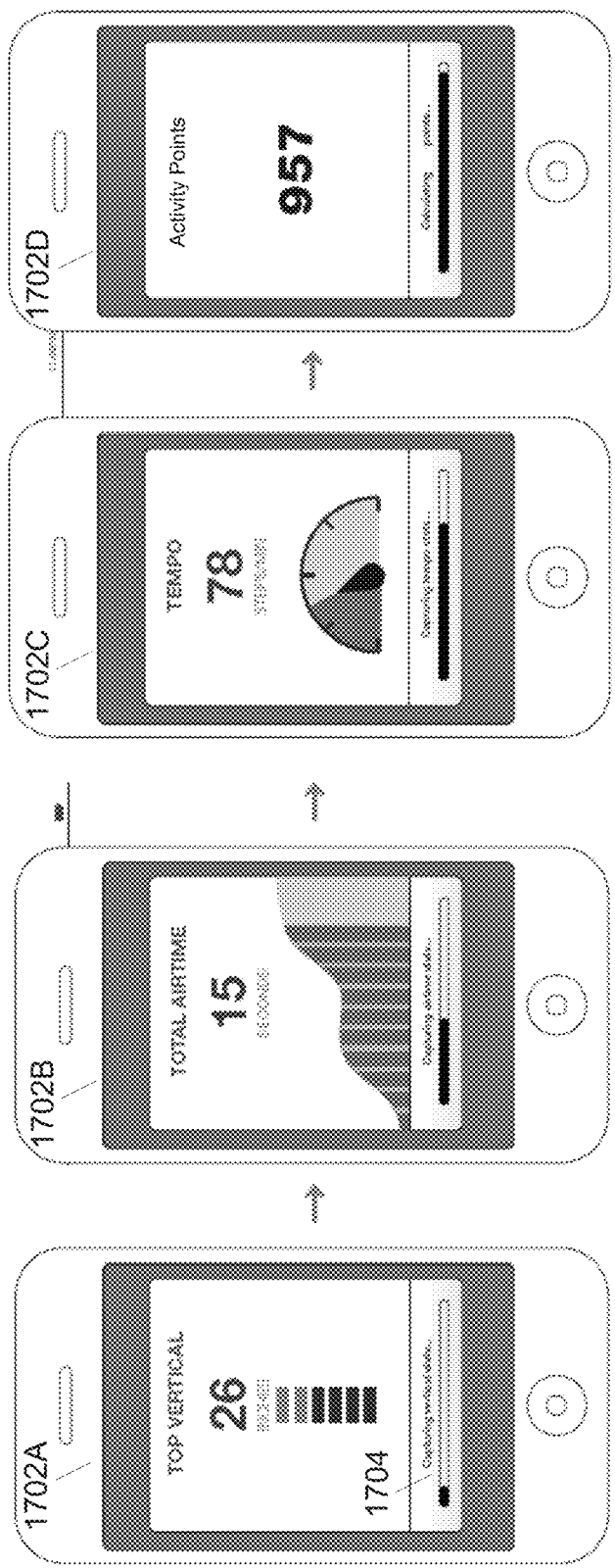
FIG. 17A  Capturing vertical stats
FIG. 17B  Capturing airtime stats
FIG. 17C  Capturing tempo stats
FIG. 17D  Calculating Activity Points

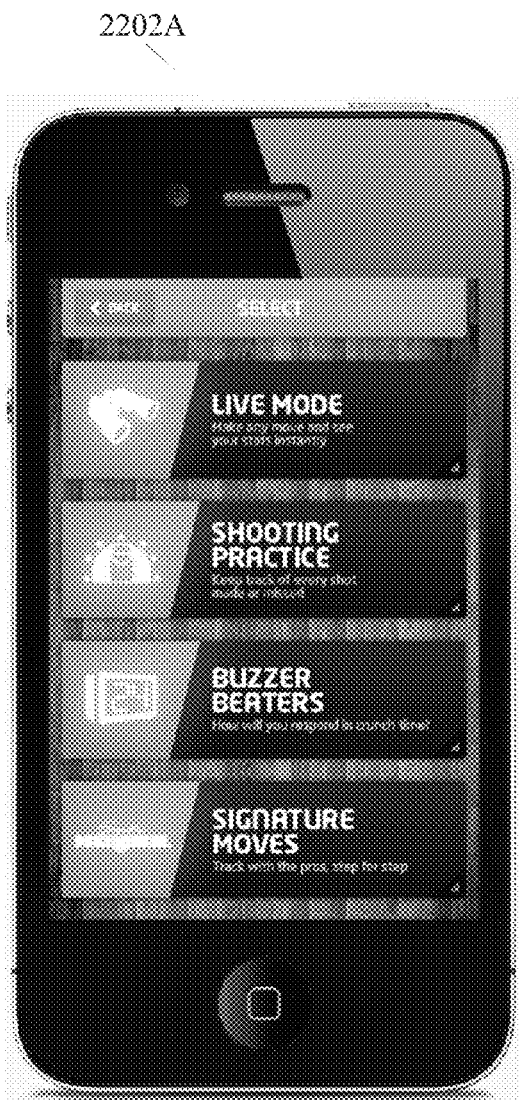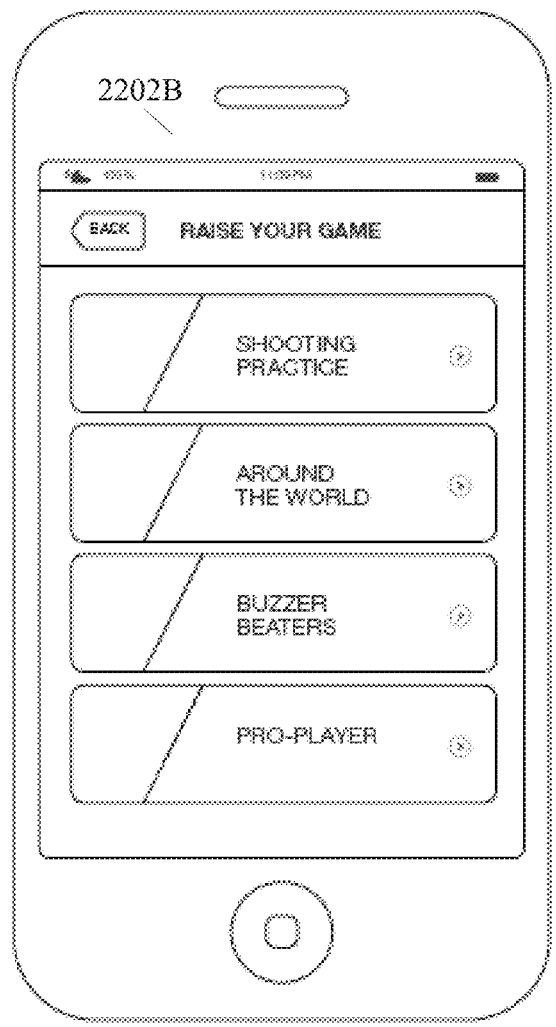
FIG. 22A                    FIG. 22B

| GAME TITLE | DESCRIPTION | METRICS |
|---|---|---|
| SHOOTING PRACTICE | Shoot around mode will allow players to use simple gestures on the device tap/swipe) to keep track of every shot made or missed. | - Activity Points<br>- Play Time<br>- Made/Missed Shots<br>- Total Shots<br>- Shooting Percentage<br>- Hot Streak (Most shots made in a row)<br>- Vertical Sweet Spot (Jump height of most shots made)<br>- Number of Balanced/Off-Balanced Shots |
| AROUND THE WORLD | Ballers practice quick transition jump shots by being prompted to shoot at a set number of specific spots around the mid-range or long-distance perimeter. The player can only advances to the next spot if the shot is made. The goal is to make all the shots in the least amount of time or with least amount of shot attempts. | - Activity Points<br>- Time Finished<br>- Made/Missed Shots<br>- Total Shots<br>- Shooting Percentage<br>- Hot Streak<br>- Quickness (Steps/Min)<br>- Average Vertical |
| BUZZER BEATERS | Ballers will begin by setting the shot clock time and increasing the level of distraction. Each level of the game will randomly pick a different type of shot that the user has to take: half-court, lay-ups, fade-away jumpers etc. Users may track made/missed shots using a gesture. | - Activity Points<br>- Made/Missed Shots<br>- Total Shots<br>- Shooting Percentage<br>- Quickness (Steps/Min)<br>- Fakes/Change of Direction<br>- Average Vertical |

FIG. 23

| GAME TITLE | DESCRIPTION | METRICS |
|---|---|---|
| PRO- PLAYER | In this inspirational game, players will be given a series of Pro classic moment videos and challenged to match the movements and stats of the Pro Player. If the player matches a high percentage of the Pro Player's stat, they will unlock a badge and exclusive content about the history of that shot. | - Activity Points<br>- Shot Accuracy (Percentage of Stats Matched to Pro)<br>- Vertical Jump (Pro vs Player)<br>- Airtime (Pro vs Player)<br>- Quickness (Pro vs Player)<br>- Fake/Change of Direction (Pro vs Player) |
| BASIC | This is a basic live inside feature within the app that allows users to quickly get statistics. Users will use this app to see how high they can jump or total airtime they can grab without having to go into the Track Game section. Ultimately, this feature can be used by ballers to create their own challenges and compare stats with their friends. | - Vertical Jump Height<br>- Airtime<br>- Quickness |
| AIR TIME | This non-shooting game allows players to strengthen the skill for rebounding and second hops ability by tasking them to consistently throw a basketball against a backboard while in mid-air. The objective of the game is to max out their Total Airtime in a limited amount of time. | - Total Number of Jumps<br>- Total Airtime<br>- Top Airtime<br>- Second Jump Ability |

FIG. 24

| GAME TITLE | DESCRIPTION | METRICS |
|---|---|---|
| CONTINUOUS CROSSOVER | This game tests the user's ability to dribble between their legs as many times as possible in a set period of time. Each dribble between the legs will be tracked by the player's feet movement (alternating split lunges). | - Total Number of Crossovers<br>- Quickness (lunges or steps per min)<br>- Hot Streak (top number of consecutive crossovers) |
| FREE THROW | To improve a player's free throw form consistency, this game tasks the user to shoot a predetermined number of free throw shots. The objective may not be to make the shots, but to shoot each shot with consistency of selected metrics (e.g., consistent balance). Meeting a specific gauge of balance (e.g., percentage) consistency may result in a higher score. Game levels may be integrated and with each advancement increases the level of noise and distraction. | - Balance Consistency (% of Shots Made with Consistent Balance)<br>- Percentage of Time on Toes<br>- Percentage of Time on Heels<br>- Balance Heat Map per Shot |
| SIGNATURE MOVES | This non-shooting game allows players to try and mimic the stats of Pro signature moves. This can be based on those signature moves that currently fire on a website. Similar to Pro-Moments, users can unlock exclusive tips and tricks from their favorite pros. | - Total Number of Jumps<br>- Total Airtime<br>- Top Airtime<br>- Second Jump Ability<br>- Fakes/Change of Direction |

FIG. 25

| GAME TITLE | DESCRIPTION | METRICS |
|---|---|---|
| PRO BATTLES | This shooting game allows users to choose a pro to go into a shooting contest with. The player must shoot anywhere behind the 3-point line. If the player makes a shot, he or she receives one point. If the player misses a shot, the pro receives 2 points. First player to 10 wins. Obviously, the object of the game is to make 10 3-pointers before you miss 5 3-pointers in order to win. | - Score (Player vs Pro)<br>- Made/Missed Shots<br>- Total Shots<br>- Shooting Percentage<br>- Vertical Sweet Spot (Jump height of most shots made)<br>- Number of Balanced/Off-Balanced Shots |
| H-O-R-S-E | This version of H-O-R-S-E can be played against a Pro or another player         . For the Pro version, the user is challenged to make a shot with specific      stats to match. If the user makes the shot, but it does not match the      stats, the shot does not count. Similarly, for the multi-player version, users challenge each other with shots, but have to match the         stats as well. | - Total Number of Jumps<br>- Total Airtime<br>- Top Airtime<br>- Second Jump Ability<br>- Fakes/Change of Direction |

FIG. 26

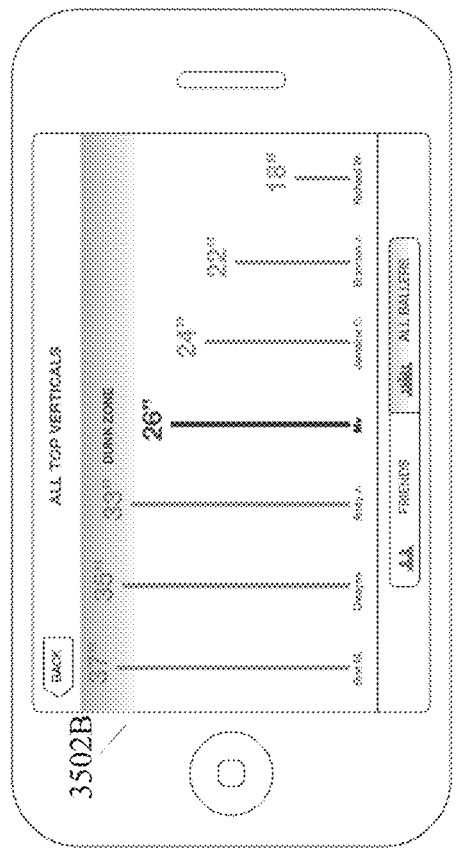
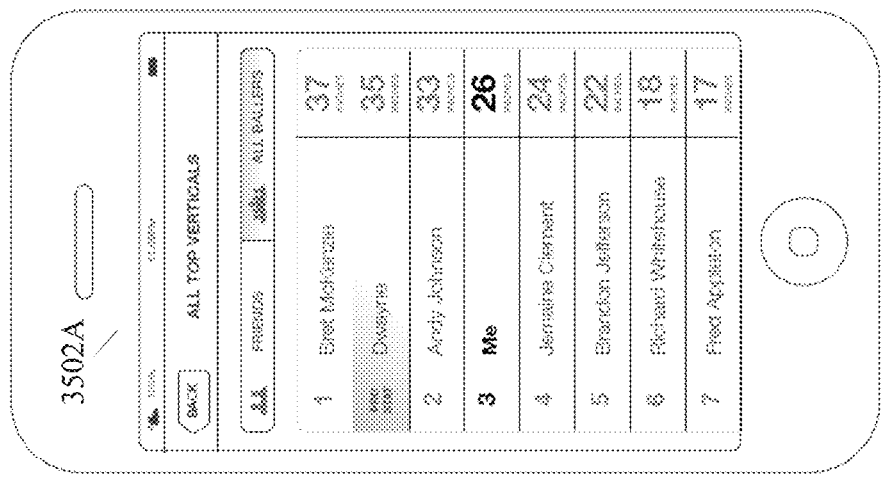
FIG. 35A
FIG. 35B

SELECTING AND CORRELATING PHYSICAL ACTIVITY DATA WITH IMAGE DATA

CROSS REFERENCE TO RELATED APPLICATIONS

This application claims the benefit of and is a continuation of U.S. patent application Ser. No. 16/232,628 filed Dec. 26, 2018, which is a continuation of U.S. patent application Ser. No. 15/197,014 filed Jun. 29, 2016, issued as U.S. Pat. No. 10,179,263 on Jan. 15, 2019, which is a continuation of U.S. patent application Ser. No. 13/399,452 filed Feb. 17, 2012, issued as U.S. Pat. No. 9,411,940 on Aug. 9, 2016, which claims the benefit of and priority to, U.S. Provisional Patent No. 61/443,808 filed Feb. 17, 2011, The contents of the above noted applications are incorporated herein by reference herein in their entirety for any and all non-limiting purposes.

BACKGROUND

Exercise and fitness have become increasingly popular and the benefits from such activities are well known. Various types of technology have been incorporated into fitness and other athletic activities. For example, a wide variety of portable electronic devices are available for use in fitness activity such as MP3 or other audio players, radios, portable televisions, DVD players, or other video playing devices, watches, GPS systems, pedometers, mobile telephones, pagers, beepers, etc. Many fitness enthusiasts or athletes use one or more of these devices when exercising or training to keep them entertained, provide performance data or to keep them in contact with others, etc. Such users have also demonstrated an interest in recording their athletic activities and metrics associated therewith. Accordingly, various sensors may be used to detect, store and/or transmit athletic performance information. Oftentimes, however, athletic performance information is presented in a vacuum or based on the overall athletic activity. Exercisers may be interested in obtaining additional information about their workouts.

SUMMARY

The following presents a general summary of example aspects to provide a basic understanding of example embodiments. This summary is not an extensive overview. It is not intended to identify key or critical elements or to delineate scope of the invention. The following summary merely presents some concepts of the invention in a general form as a prelude to the more detailed description provided below.

One or more aspects describe systems, apparatuses, computer readable media, and methods for tracking performance metrics of a user during an exercise session.

In some example aspects, the systems, apparatuses, computer readable media, and methods may be configured to process input specifying a user attribute, adjust a performance zone based on the user attribute, receive data generated by at least one of an accelerometer and a force sensor, determine whether the data is within the performance zone, and output the determination.

In some example aspects, the systems, apparatuses, computer readable media, and methods may include receiving data generated by a sensor (e.g., an accelerometer, a force sensor, temperature sensor, heart rate monitor, etc.) as a user performs an athletic movement, and comparing the data with comparison data of a plurality of playing styles to determine a particular one of the playing styles most closely matching the data.

In some example aspects, the systems, apparatuses, computer readable media, and methods may include receiving data generated by a force sensor indicating a weight distribution during a performance of a plurality of exercise tasks, processing first input indicating successful completion of an exercise task, associating a first weight distribution at a time preceding the first input with the successful completion of the exercise task, processing second input indicating unsuccessful completion of the exercise task, and associating a second weight distribution at a time preceding the second input with the unsuccessful completion of the exercise task.

In some example aspects, the systems, apparatuses, computer readable media, and methods may include receiving signature move data corresponding to acceleration and force measurement data measured by a first user performing a sequence of events, receiving player data from at least one of an accelerometer and a force sensor by monitoring a second user attempting to perform the sequence of events, and generating a similarity metric indicating how similar the player data is to the signature move data.

In some example aspects, the systems, apparatuses, computer readable media, and methods may include receiving data generated by at least one of an accelerometer and a force sensor, comparing the data to jump data to determine that the data is consistent with a jump, processing the data to determine a lift off time, a landing time, and a loft time, and calculating a vertical leap based on the loft time.

Other aspects and features are described throughout the disclosure.

BRIEF DESCRIPTION OF THE DRAWINGS

To understand the example embodiments, it will now be described by way of example, with reference to the accompanying drawings in which:

FIGS. 4A-B illustrate examples of pod sensors that may be embedded and removed from a shoe in accordance with example embodiments.

FIGS. 6-7 illustrates example various off-body configurations for a computer in accordance with example embodiments.

FIG. 9 illustrates example performance metrics for user selection in accordance with example embodiments.

FIGS. 10A-C illustrate an example of calibrating sensors in accordance with example embodiments.

FIGS. 11A-B illustrate an example of calibrating sensors in accordance with example embodiments.

FIGS. 17A-D illustrate further example displays of a GUI for displaying performance metrics to a user in accordance with example embodiments.

FIGS. 22A-B illustrate example training displays presenting user-selectable training sessions in accordance with example embodiments.

FIGS. 23-26 illustrate example training sessions in accordance with example embodiments.

FIGS. 35A-B illustrate example displays for comparing a user's performance metrics to other individuals in accordance with example embodiments.

DETAILED DESCRIPTION

In the following description of the various embodiments, reference is made to the accompanying drawings, which form a part hereof, and in which is shown by way of illustration various embodiments in which the disclosure may be practiced. It is to be understood that other embodiments may be utilized and structural and functional modifications may be made without departing from the scope and spirit of the present disclosure. Further, headings within this disclosure should not be considered as limiting aspects of the disclosure. Those skilled in the art with the benefit of this disclosure will appreciate that the example embodiments are not limited to the example headings.

I. Example Personal Training System

A. Illustrative Computing Devices

Figure 1A:
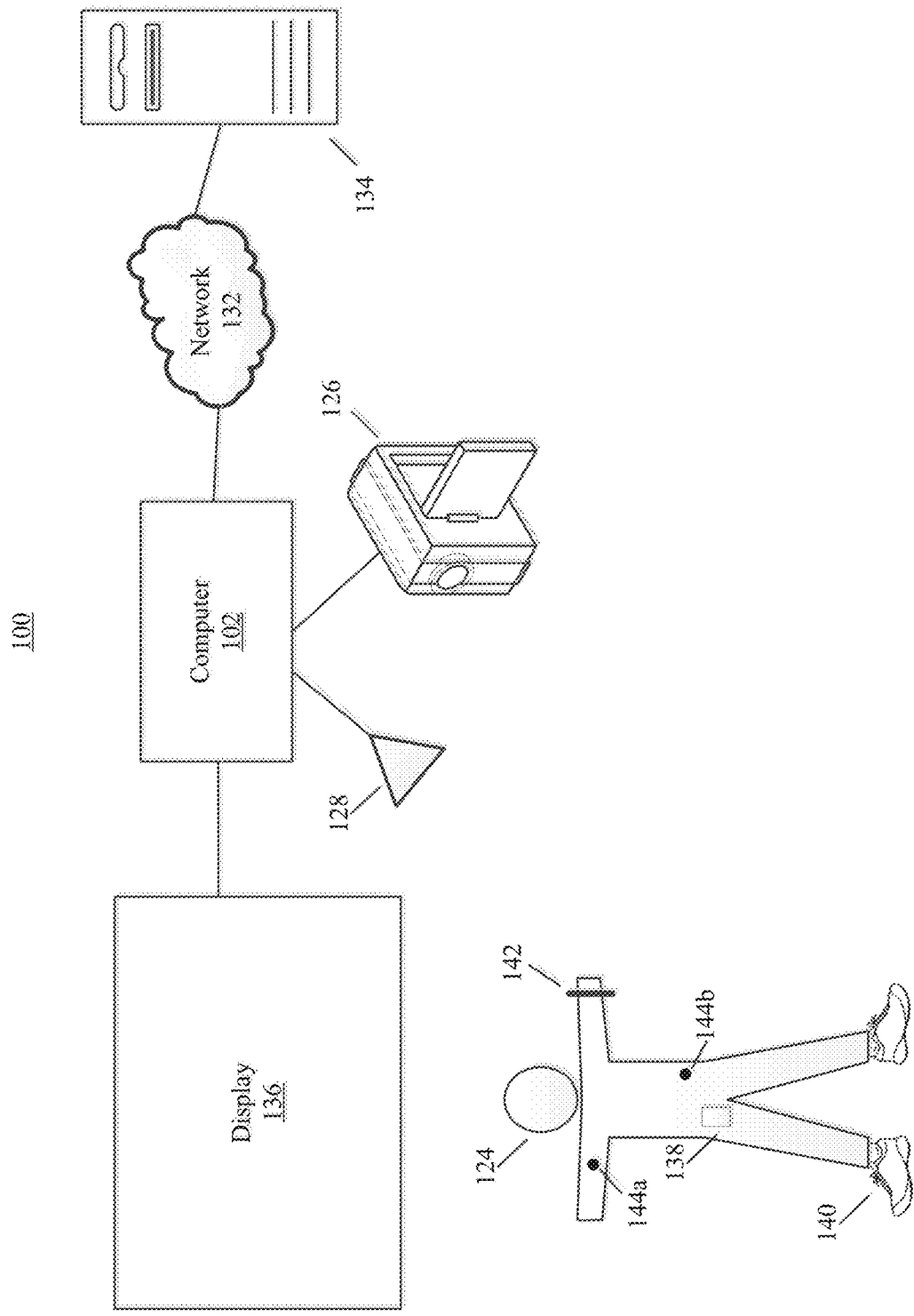
FIGS. 1A-B illustrate an example of a personal training system in accordance with example embodiments.

FIG. 1A illustrates an example of a personal training system 100 in accordance with example embodiments. Example system 100 may include one or more electronic devices, such as computer 102. Computer 102 may comprise a mobile terminal, such as a telephone, music player, tablet, netbook or any portable device. In other embodiments, computer 102 may comprise a set-top box (STB), desktop computer, digital video recorder(s) (DVR), computer server(s), and/or any other desired computing device. In certain configurations, computer 102 may comprise a gaming console, such as for example, a Microsoft® XBOX, Sony® Playstation, and/or a Nintendo® Wii gaming consoles. Those skilled in the art will appreciate that these are merely example consoles for descriptive purposes and this disclosure is not limited to any console or device.

Figure 1B:
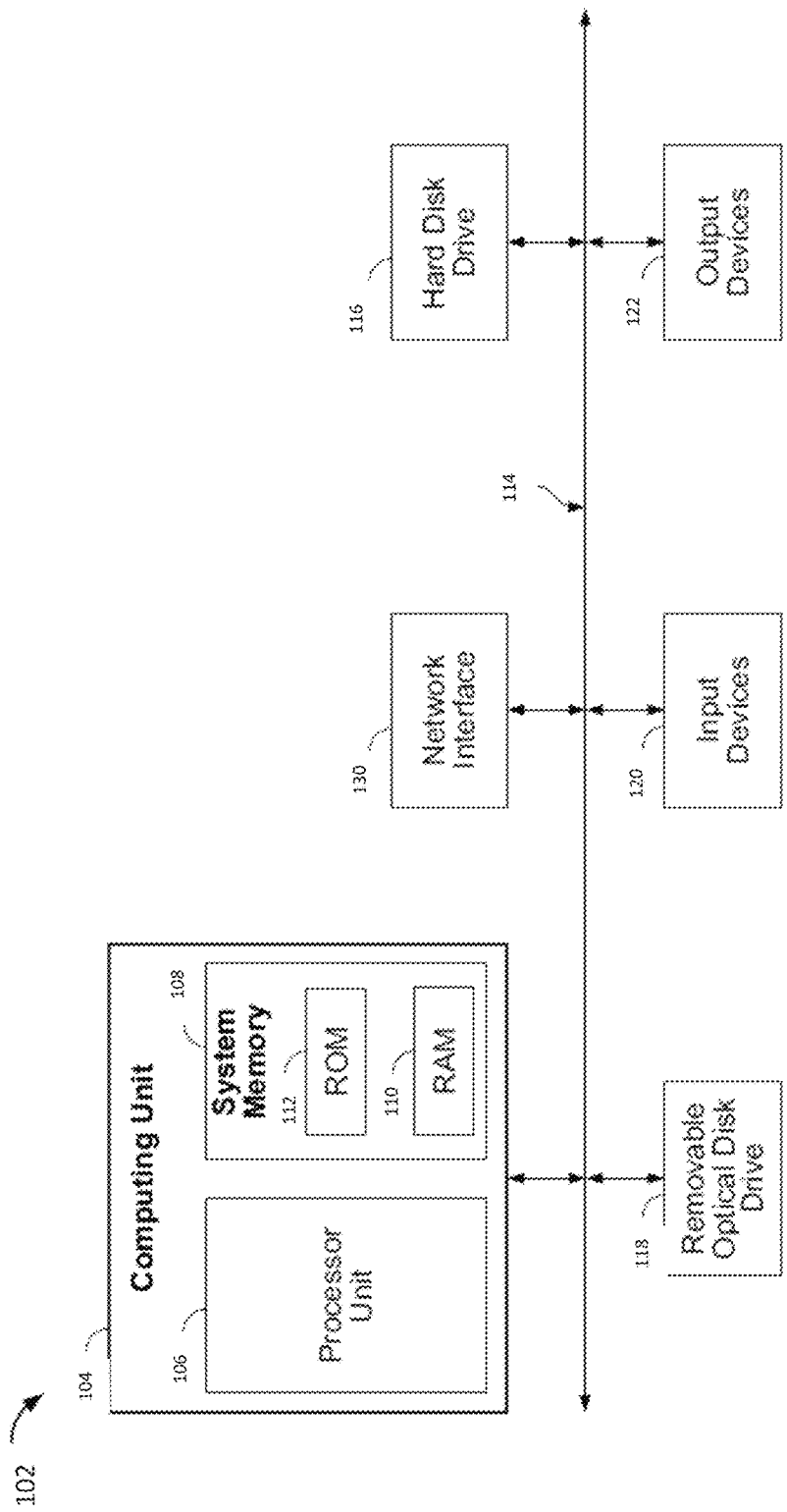

Turning briefly to FIG. 1B, computer 102 may include computing unit 104, which may comprise at least one processing unit 106. Processing unit 106 may be any type of processing device for executing software instructions, such as for example, a microprocessor device. Computer 102 may include a variety of non-transitory computer readable media, such as memory 108. Memory 108 may include, but is not limited to, random access memory (RAM) such as RAM 110, and/or read only memory (ROM), such as ROM 112. Memory 108 may include any of: electronically erasable programmable read only memory (EEPROM), flash memory or other memory technology, CD-ROM, digital versatile disks (DVD) or other optical disk storage, magnetic storage devices, or any other medium that can be used to store the desired information and that can be accessed by computer 102.

The processing unit 106 and the system memory 108 may be connected, either directly or indirectly, through a bus 114 or alternate communication structure to one or more peripheral devices. For example, the processing unit 106 or the system memory 108 may be directly or indirectly connected to additional memory storage, such as a hard disk drive 116, a removable magnetic disk drive, an optical disk drive 118, and a flash memory card. The processing unit 106 and the system memory 108 also may be directly or indirectly connected to one or more input devices 120 and one or more output devices 122. The output devices 122 may include, for example, a display device 136, television, printer, stereo, or speakers. In some embodiments one or more display devices may be incorporated into eyewear. The display devices incorporated into eyewear may provide feedback to users. Eyewear incorporating one or more display devices also provides for a portable display system. The input devices 120 may include, for example, a keyboard, touch screen, a remote control pad, a pointing device (such as a mouse, touchpad, stylus, trackball, or joystick), a scanner, a camera or a microphone. In this regard, input devices 120 may comprise one or more sensors configured to sense, detect, and/or measure athletic movement from a user, such as user 124, shown in FIG. 1A.

Looking again to FIG. 1A, image-capturing device 126 and/or sensor 128 may be utilized in detecting and/or measuring athletic movements of user 124. In one embodiment, data obtained from image-capturing device 126 or sensor 128 may directly detect athletic movements, such that the data obtained from image-capturing device 126 or sensor 128 is directly correlated to a motion parameter. Yet, in other embodiments, data from image-capturing device 126 and/or sensor 128 may be utilized in combination, either with each other or with other sensors to detect and/or measure movements. Thus, certain measurements may be determined from combining data obtained from two or more devices. Image-capturing device 126 and/or sensor 128 may include or be operatively connected to one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Example uses of illustrative sensors 126, 128 are provided below in Section I.C, entitled "Illustrative Sensors." Computer 102 may also use touch screens or image capturing device to determine where a user is pointing to make selections from a graphical user interface. One or more embodiments may utilize one or more wired and/or wireless technologies, alone or in combination, wherein examples of wireless technologies include Bluetooth® technologies, Bluetooth® low energy technologies, and/or ANT technologies.

B. Illustrative Network

Computer 102, computing unit 104, and/or any other electronic devices may be directly or indirectly connected to one or more network interfaces, such as example interface 130 (shown in FIG. 1B) for communicating with a network, such as network 132. In the example of FIG. 1B, network interface 130, may comprise a network adapter or network interface card (NIC) configured to translate data and control signals from the computing unit 104 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 130 may employ any suitable connection agent for connecting to a network, including, for example, a wireless transceiver, a power line adapter, a modem, or an Ethernet connection. Network 132, however, may be any one or more information distribution network(s), of any type(s) or topology(s), alone or in combination(s), such as internet(s), intranet(s), cloud(s), LAN(s). Network 132 may be any one or more of cable, fiber, satellite, telephone, cellular, wireless, etc. Networks are well known in the art, and thus will not be discussed here in more detail. Network 132 may be variously configured such as having one or more wired or wireless communication channels to connect one or more locations (e.g., schools, businesses, homes, consumer dwellings, network resources, etc.), to one or more remote servers 134, or to other computers, such as similar or identical to computer 102.

Indeed, system 100 may include more than one instance of each component (e.g., more than one computer 102, more than one display 136, etc.).

Regardless of whether computer 102 or other electronic device within network 132 is portable or at a fixed location, it should be appreciated that, in addition to the input, output and storage peripheral devices specifically listed above, the computing device may be connected, such as either directly, or through network 132 to a variety of other peripheral devices, including some that may perform input, output and storage functions, or some combination thereof. In certain embodiments, a single device may integrate one or more components shown in FIG. 1A. For example, a single device may include computer 102, image-capturing device 126, sensor 128, display 136 and/or additional components. In one embodiment, sensor device 138 may comprise a mobile terminal having a display 136, image-capturing device 126, and one or more sensors 128. Yet, in another embodiment, image-capturing device 126, and/or sensor 128 may be peripherals configured to be operatively connected to a media device, including for example, a gaming or media system. Thus, it goes from the foregoing that this disclosure is not limited to stationary systems and methods. Rather, certain embodiments may be carried out by a user 124 in almost any location.

C. Illustrative Sensors

Computer 102 and/or other devices may comprise one or more sensors 126, 128 configured to detect and/or monitor at least one fitness parameter of a user 124. Sensors 126 and/or 128 may include, but are not limited to: an accelerometer, a gyroscope, a location-determining device (e.g., GPS), light sensor, temperature sensor (including ambient temperature and/or body temperature), sleep pattern sensors, heart rate monitor, image-capturing sensor, moisture sensor and/or combinations thereof. Network 132 and/or computer 102 may be in communication with one or more electronic devices of system 100, including for example, display 136, an image capturing device 126 (e.g., one or more video cameras), and sensor 128, which may be an infrared (IR) device. In one embodiment sensor 128 may comprise an IR transceiver. For example, sensors 126, and/or 128 may transmit waveforms into the environment, including towards the direction of user 124 and receive a "reflection" or otherwise detect alterations of those released waveforms. In yet another embodiment, image-capturing device 126 and/or sensor 128 may be configured to transmit and/or receive other wireless signals, such as radar, sonar, and/or audible information. Those skilled in the art will readily appreciate that signals corresponding to a multitude of different data spectrums may be utilized in accordance with various embodiments. In this regard, sensors 126 and/or 128 may detect waveforms emitted from external sources (e.g., not system 100). For example, sensors 126 and/or 128 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology. As a non-limited example, image-capturing devices configured to perform range phenomenology are commercially available from Flir Systems, Inc. of Portland, Oregon Although image capturing device 126 and sensor 128 and display 136 are shown in direct (wirelessly or wired) communication with computer 102, those skilled in the art will appreciate that any may directly communicate (wirelessly or wired) with network 132.

1. Multi-Purpose Electronic Devices

User 124 may possess, carry, and/or wear any number of electronic devices, including sensory devices 138, 140, 142, and/or 144. In certain embodiments, one or more devices 138, 140, 142, 144 may not be specially manufactured for fitness or athletic purposes. Indeed, aspects of this disclosure relate to utilizing data from a plurality of devices, some of which are not fitness devices, to collect, detect, and/or measure athletic data. In one embodiment, device 138 may comprise a portable electronic device, such as a telephone or digital music player, including an IPOD®, IPAD®, or iPhone®, brand devices available from Apple, Inc. of Cupertino, California or Zune® or Microsoft® Windows devices available from Microsoft of Redmond, Washington. As known in the art, digital media players can serve as both an output device for a computer (e.g., outputting music from a sound file or pictures from an image file) and a storage device. In one embodiment, device 138 may be computer 102, yet in other embodiments, computer 102 may be entirely distinct from device 138. Regardless of whether device 138 is configured to provide certain output, it may serve as an input device for receiving sensory information. Devices 138, 140, 142, and/or 144 may include one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. In certain embodiments, sensors may be passive, such as reflective materials that may be detected by image-capturing device 126 and/or sensor 128 (among others). In certain embodiments, sensors 144 may be integrated into apparel, such as athletic clothing. For instance, the user 124 may wear one or more on-body sensors 144*a-b*. Sensors 144 may be incorporated into the clothing of user 124 and/or placed at any desired location of the body of user 124. Sensors 144 may communicate (e.g., wirelessly) with computer 102, sensors 128, 138, 140, and 142, and/or camera 126. Examples of interactive gaming apparel are described in U.S. patent application Ser. No. 10/286,396, filed Oct. 30, 2002, and published as U.S. Pat. Pub, No. 2004/0087366, the contents of which are incorporated herein by reference in its entirety for any and all non-limiting purposes. In certain embodiments, passive sensing surfaces may reflect waveforms, such as infrared light, emitted by image-capturing device 126 and/or sensor 128. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Devices 138-144, as well as any other electronic device disclosed herein, including any sensory device, may communicate with each other, either directly or through a network, such as network 132. Communication between one or more of devices 138-144 may take place via computer 102. For example, two or more of devices 138-144 may be peripherals operatively connected to bus 114 of computer 102. In yet another embodiment, a first device, such as device 138 may communicate with a first computer, such as computer 102 as well as another device, such as device 142, however, device 142 may not be configured to connect to computer 102 but may communicate with device 138. Further, one or more electronic devices may be configured to communicate through multiple communication pathways. For example, device 140 may be configured to communicate via a first wireless communication protocol with device 138 and further communicate through a second wireless communication protocol with a different device, such as for example, computer 102. Example wireless protocols are discussed throughout this disclosure and are known in the art. Those skilled in the art will appreciate that other configurations are possible.

Some implementations of the example embodiments may alternately or additionally employ computing devices that are intended to be capable of a wide variety of functions, such as a desktop or laptop personal computer. These computing devices may have any combination of peripheral devices or additional components as desired. Also, the components shown in FIG. 1B may be included in the server 134, other computers, apparatuses, etc.

2. Illustrative Apparel/Accessory Sensors

In certain embodiments, sensory devices 138, 140, 142 and/or 144 may be formed within or otherwise associated with user's 124 clothing or accessories, including a watch, armband, wristband, necklace, shirt, shoe, or the like. Examples of shoe-mounted and wrist-worn devices (devices 140 and 142, respectively) are described immediately below, however, these are merely example embodiments and this disclosure should not be limited to such.

i. Shoe-Mounted Device

In certain embodiments, sensory device 140 may comprise footwear which may include one or more sensors, including but not limited to: an accelerometer, location-sensing components, such as GPS, and/or a force sensor system. FIG. 2A illustrates one example embodiment of a sensor system 202 in accordance with example embodiments. In certain embodiments, system 202 may include a sensor assembly 204. Assembly 204 may comprise one or more sensors, such as for example, an accelerometer, location-determining components, and/or force sensors. In the illustrated embodiment, assembly 204 incorporates a plurality of sensors, which may include force-sensitive resistor (FSR) sensors 206. In yet other embodiments, other sensor(s) may be utilized. Port 208 may be positioned within a sole structure 209 of a shoe. Port 208 may optionally be provided to be in communication with an electronic module 210 (which may be in a housing 211) and a plurality of leads 212 connecting the FSR sensors 206 to the port 208. Module 210 may be contained within a well or cavity in a sole structure of a shoe. The port 208 and the module 210 include complementary interfaces 214, 216 for connection and communication.

In certain embodiments, at least one force-sensitive resistor 206 shown in FIG. 2A may contain first and second electrodes or electrical contacts 218, 220 and a force-sensitive resistive material 222 disposed between the electrodes 218, 220 to electrically connect the electrodes 218, 220 together. When pressure is applied to the force-sensitive material 222, the resistivity and/or conductivity of the force-sensitive material 222 changes, which changes the electrical potential between the electrodes 218, 220. The change in resistance can be detected by the sensor system 202 to detect the force applied on the sensor 216. The force-sensitive resistive material 222 may change its resistance under pressure in a variety of ways. For example, the force-sensitive material 222 may have an internal resistance that decreases when the material is compressed, similar to the quantum tunneling composites described in greater detail below. Further compression of this material may further decrease the resistance, allowing quantitative measurements, as well as binary (on/off) measurements. In some circumstances, this type of force-sensitive resistive behavior may be described as "volume-based resistance," and materials exhibiting this behavior may be referred to as "smart materials." As another example, the material 222 may change the resistance by changing the degree of surface-to-surface contact. This can be achieved in several ways, such as by using microprojections on the surface that raise the surface resistance in an uncompressed condition, where the surface resistance decreases when the microprojections are compressed, or by using a flexible electrode that can be deformed to create increased surface-to-surface contact with another electrode. This surface resistance may be the resistance between the material 222 and the electrodes 218, 220 and/or the surface resistance between a conducting layer (e.g., carbon/graphite) and a force-sensitive layer (e.g., a semiconductor) of a multi-layer material 222. The greater the compression, the greater the surface-to-surface contact, resulting in lower resistance and enabling quantitative measurement. In some circumstances, this type of force-sensitive resistive behavior may be described as "contact-based resistance." It is understood that the force-sensitive resistive material 222, as defined herein, may be or include a doped or non-doped semiconducting material.

The electrodes 218, 220 of the FSR sensor 206 can be formed of any conductive material, including metals, carbon/graphite fibers or composites, other conductive composites, conductive polymers or polymers containing a conductive material, conductive ceramics, doped semiconductors, or any other conductive material. The leads 212 can be connected to the electrodes 218, 220 by any suitable method, including welding, soldering, brazing, adhesively joining, fasteners, or any other integral or non-integral joining method. Alternately, the electrode 218, 220 and associated lead 212 may be formed of a single piece of the same material.

Other embodiments of the sensor system 202 may contain a different quantity and/or configuration of sensors and generally include at least one sensor. For example, in one embodiment, the system 202 includes a much larger number of sensors, and in another embodiment, the system 202 includes two sensors, one in the heel and one in the forefoot of a shoe or device to be close proximity to a user's foot. In addition, one or more sensors 206 may communicate with the port 214 in a different manner, including any known type of wired or wireless communication, including Bluetooth and near-field communication. A pair of shoes may be provided with sensor systems 202 in each shoe of the pair, and it is understood that the paired sensor systems may operate synergistically or may operate independently of each other, and that the sensor systems in each shoe may or may not communicate with each other. It is further understood that the sensor system 202 may be provided with computer-executable instructions stored on one or more computer-readable media that when executed by a processor control collection and storage of data (e.g., pressure data from interaction of a user's foot with the ground or other contact surface), and that these executable instructions may be stored in and/or executed by the sensors 206, any module, and/or an external device, such as device 128, computer 102, server 134 and/or network 132 of FIG. 1A.

ii. Wrist-Worn Device

Figure 2B:
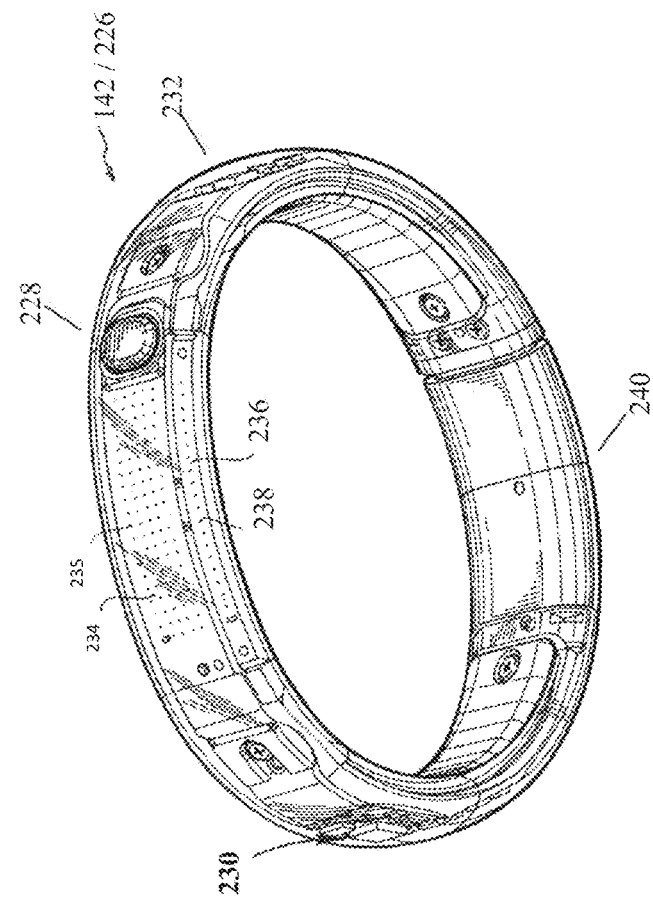
FIGS. 2A-B illustrate example embodiments of a sensor system in accordance with example embodiments.
Figure 2A:
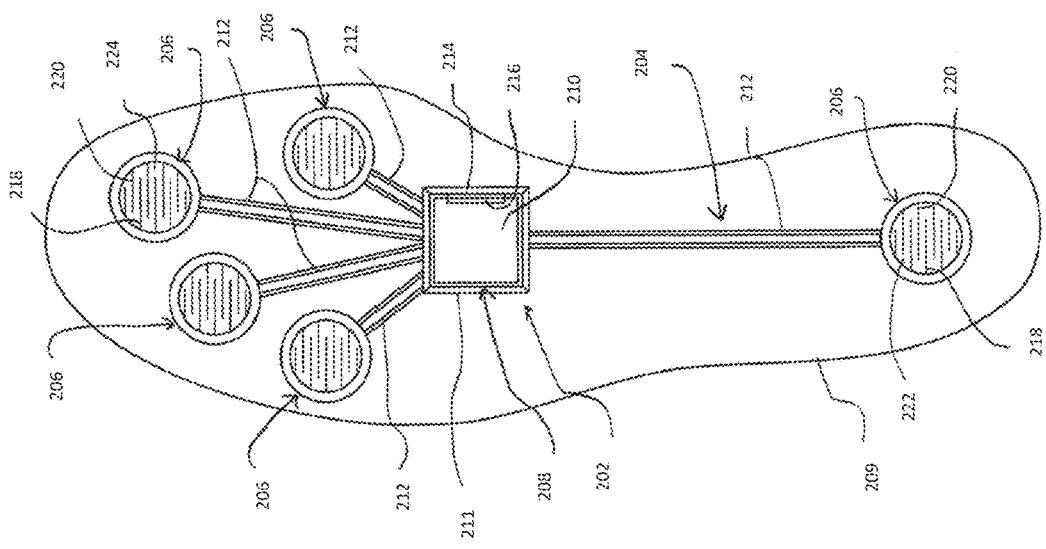

As shown in FIG. 2B, device 226 (which may resemble or be sensory device 142 shown in FIG. 1A) may be configured to be worn by user 124, such as around a wrist, arm, ankle or the like. Device 226 may monitor athletic movements of a user, including all-day activity of user 124. In this regard, device assembly 226 may detect athletic movement during user's 124 interactions with computer 102 and/or operate independently of computer 102. For example, in one embodiment, device 226 may be an-all day activity monitor that measures activity regardless of the user's proximity or interactions with computer 102. Device 226 may communicate directly with network 132 and/or other devices, such as devices 138 and/or 140. In other embodiments, athletic data obtained from device 226 may be utilized in determinations conducted by computer 102, such as determinations relating to which exercise programs are presented to user 124. In one embodiment, device 226 may also wirelessly interact with a mobile device, such as device 138 associated with user 124 or a remote website such as a site dedicated to fitness or health related subject matter. At some predetermined time, the user may wish to transfer data from the device 226 to another location.

As shown in FIG. 2B, device 226 may include an input mechanism, such as a depressible input button 228 assist in operation of the device 226. The input button 228 may be operably connected to a controller 230 and/or any other electronic components, such as one or more of the elements discussed in relation to computer 102 shown in FIG. 1B. Controller 230 may be embedded or otherwise part of housing 232. Housing 232 may be formed of one or more materials, including elastomeric components and comprise one or more displays, such as display 234. The display may be considered an illuminable portion of the device 226. The display 234 may include a series of individual lighting elements or light members such as LED lights 234 in an exemplary embodiment. The LED lights may be formed in an array and operably connected to the controller 230. Device 226 may include an indicator system 236, which may also be considered a portion or component of the overall display 234. It is understood that the indicator system 236 can operate and illuminate in conjunction with the display 234 (which may have pixel member 235) or completely separate from the display 234. The indicator system 236 may also include a plurality of additional lighting elements or light members 238, which may also take the form of LED lights in an exemplary embodiment. In certain embodiments, indicator system may provide a visual indication of goals, such as by illuminating a portion of lighting members 238 to represent accomplishment towards one or more goals.

A fastening mechanism 240 can be unlatched wherein the device 226 can be positioned around a wrist of the user 124 and the fastening mechanism 240 can be subsequently placed in a latched position. The user can wear the device 226 at all times if desired. In one embodiment, fastening mechanism 240 may comprise an interface, including but not limited to a USB port, for operative interaction with computer 102 and/or devices 138, 140.

In certain embodiments, device 226 may comprise a sensor assembly (not shown in FIG. 2B). The sensor assembly may comprise a plurality of different sensors. In an example embodiment, the sensor assembly may comprise or permit operative connection to an accelerometer (including in the form of a multi-axis accelerometer), heart rate sensor, location-determining sensor, such as a GPS sensor, and/or other sensors. Detected movements or parameters from device's 142 sensor(s), may include (or be used to form) a variety of different parameters, metrics or physiological characteristics including but not limited to speed, distance, steps taken, calories, heart rate, sweat detection, effort, oxygen consumed, and/or oxygen kinetics. Such parameters may also be expressed in terms of activity points or currency earned by the user based on the activity of the user.

Various examples may be implemented using electronic circuitry configured to perform one or more functions. For example, with some embodiments of the invention, a computing device such as a smart phone, mobile device, computer, server, or other computing equipment may be implemented using one or more application-specific integrated circuits (ASICs). More typically, however, components of various examples of the invention will be implemented using a programmable computing device executing firmware or software instructions, or by some combination of purpose-specific electronic circuitry and firmware or software instructions executing on a programmable computing device.

II. Monitoring System

Figure 3A:
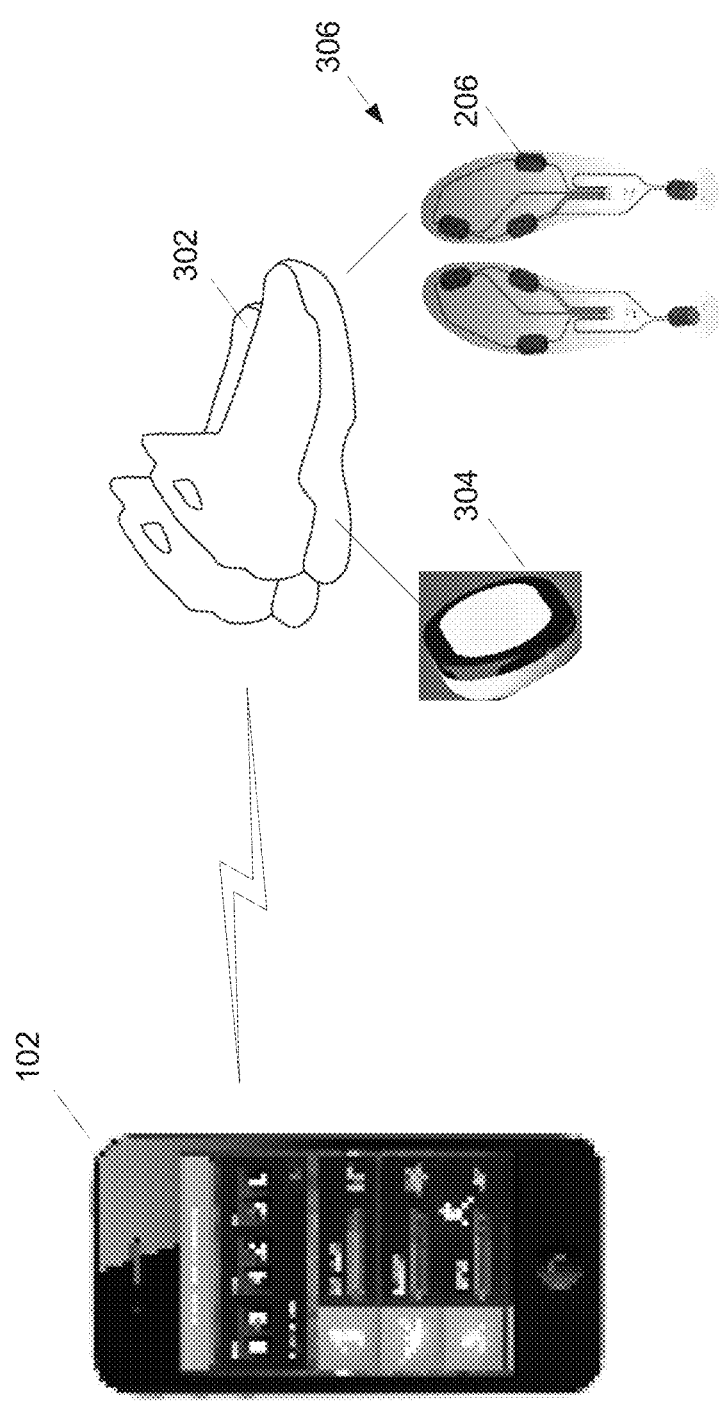
FIGS. 3A-B illustrate an example of a computer interacting with at least one sensor in accordance with example embodiments.
Figure 3B:
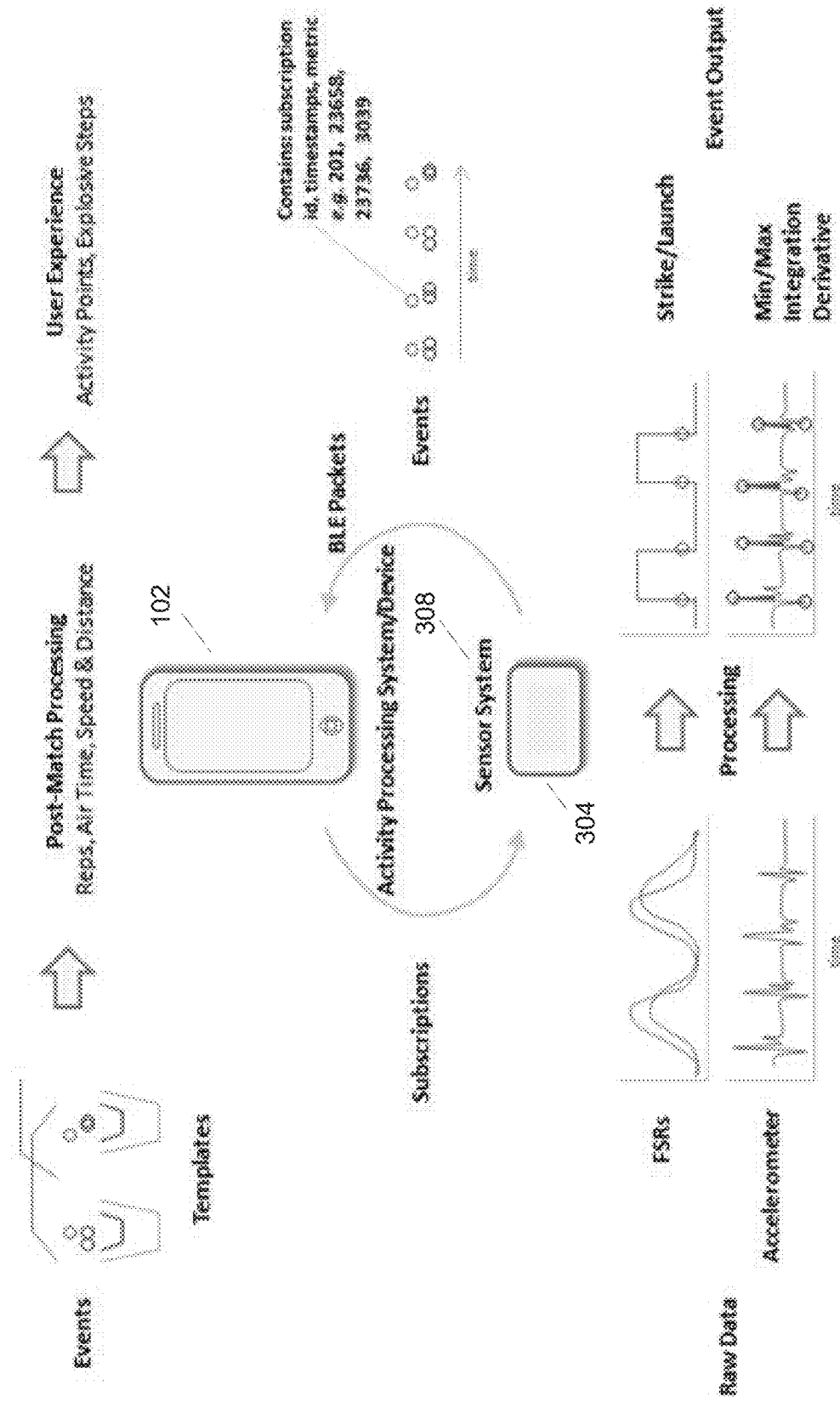

FIGS. 3A-B illustrate examples of a computer interacting with at least one sensor in accordance with example embodiments. In the depicted example, the computer 102 may be implemented as a smart phone that may be carried by the user. Example sensors may be worn on a user's body, be situated off-body, and may include any of the sensors discussed above including an accelerometer, a distributed sensor, a heart rate monitor, a temperature sensor, etc. In FIG. 3, a pod sensor 304 and a distributed sensor 306 (including, for example, sensor system 202 discussed above having one or more FSRs 206) is shown. The pod sensor 304 may include an accelerometer, a gyroscope, and/or other sensing technology. In some examples, pod sensor 304 may at least one sensor to monitor data that does not directly relate to user movement. For example, ambient sensors may be worn by the user or may be external to the user. Ambient sensors may include a temperature sensor, a compass, a barometer, a humidity sensor, or other type of sensor. Other types of sensors and combinations of sensors configured to measure user movement may also be used. Also, computer 102 may incorporate one or more sensors.

The pod sensor 304, the distributed sensor 206, as well as other types of sensors, may include a wireless transceiver to communicate with one another and the computer 102. For example, sensors 304 and 306 may communicate directly with the network 132, with other devices worn by the user (e.g., a watch, arm band device, etc.), with sensors or devices worn by a second user, an external device, etc. In an example, a sensor in a left shoe may communicate with a sensor in a right shoe. Also, one shoe may include multiple sensors that communicate with one another and/or with a processor of the shoe. Further, a pair of shoes may include a single processor that collects data from multiple sensors associated with the shoes, and a transceiver coupled to the single processor may communicate sensor data to at least one of computer 102, network 132, and server 134. In another example, one or more sensors of a shoe may communicate to a transceiver that communicates with at least one of computer 102, network 132, and server 134. Further, sensors associated with a first user may communicate with sensors associated with a second user. For example, sensors in the first user's shoes may communicate with sensors in a second user's shoes. Other topographies may also be used.

The computer 102 may exchange data with the sensors, and also may communicate data received from the sensors via the network 132 to the server 134 and/or to another computer 102. A user may wear head phones or ear buds to receive audio information from the computer 102, directly from one or more of the sensors, from the server 134, from the network 132, from other locations, and combinations thereof. The head phones may be wired or wireless. For example, a distributed sensor 306 may communicate data to head phones for audible output to the user.

In an example, a user may wear shoes that are each equipped with an accelerometer, a force sensor or the like, to allow the computer 102 and/or the server 134 to determine the individual movement and metrics of each foot or other body part (e.g., leg, hand, arm, individual fingers or toes, regions of a person's foot or leg, hips, chest, shoulders, head, eyes) alone or in combination with the systems described above with reference to FIGS. 1A-B and 2A-2B.

Processing of data may distributed in any way, or performed entirely at one shoe, at the computer 102, in the server 134, or combinations thereof. In the description below, computer 102 may be described as performing a function. Other devices, including server 134, a controller, another computer, a processor in a shoe or other article of clothing, or other device may performing the function instead of or in addition to computer 102. For example, one or more sensors of each shoe (or other peripheral sensor) could be mated with a respective, local controller that performs some or all processing of raw signal output by one or more sensors. The controller's processing, at any given time, may be subject to command and control of a higher tiered computing device (e.g., computer 102). That higher tiered device may receive and further process the processed sensor signals, from that one or plural controllers, e.g., via one or more transceivers. Comparisons and calculations may be made at one or more computing devices, including some or all of the above computing devices, with or without additional computing devices. Sensors may sense desired conditions and generate raw signals, the raw signals being processed so as to provide processed data. The processed data may then be used for determining current performance metrics (e.g., current speed of travel, etc.) and the determinations may change depending on user input (e.g., how high did I jump?) and/or programming (e.g., did the user do the indicated exercise and, if that is detected, how is it qualified/quantified in the user experience).

In an example, sensors 304 and 306 may process and store measurement data, and forward the processed data (e.g., average acceleration, highest speed, total distance, etc.) to the computer 102 and/or the server 134. The sensors 304 and 306 may also send raw data to the computer 102 and/or the server 134 for processing. Raw data, for example, may include an acceleration signal measured by an accelerometer over time, a pressure signal measured by a pressure sensor over time, etc. Examples of multi-sensor apparel and the use of multiple sensors in athletic activity monitoring are described in U.S. application Ser. No. 12/483,824, entitled "FOOTWEAR HAVING SENSOR SYSTEM," and published as U.S. Publication No. 2010/0063778 A1 and U.S. application Ser. No. 12/483,828, entitled "FOOTWEAR HAVING SENSOR SYSTEM," and published as U.S. Publication No. 2010/0063779 A1. The content of the above referenced applications are incorporated herein by reference in their entirety. In a particular example, an athlete may wear shoes 302 having one or more force sensing systems, e.g., that utilize force-sensitive resistor (FSR) sensors, as shown in FIG. 2A and described in the above noted patent publications. The shoe 302 may have multiple FSR sensors 206 that detect forces at different regions of the user's foot (e.g., a heel, mid-sole, toes, etc.). Computer 102 may process data from FSR sensors 206 to determine balance of a user's foot and/or between a user's two feet. For example, computer 102 may compare a force measurement by a FSR 206 from a left shoe relative to a force measurement by a FSR 206 from a right shoe to determine balance and/or weight distribution.

FIG. 3B is another example data flow diagram in which computer 102 interacts with at least one sensor processing system 308 to detect user actions. Sensor processing system 308 may be physically separate and distinct from computer 102 and may communicate with computer 102 through wired or wireless communication. Sensor processing system 308 may include sensor 304, as shown, as well as other sensors (e.g., sensor 306) instead of or in addition to sensor 304. In the depicted example, sensor system 308 may receive and process data from sensor 304 and FSR sensor 206. Computer 102 may receive input from a user about a type of activity session (e.g., cross training, basketball, running, etc.) the user desires to perform. Instead or additionally, computer 102 may detect a type of activity the user is performing or receive information from another source about the type of activity being performed.

Based on activity type, computer 102 may identify one or more predefined action templates and communicate a subscription to sensor system 308. Action templates may be used to identify motions or actions that a user may perform while performing the determined type of activity. For example, an action may correspond to a group of one or more events, such as detecting that a user has taken a step to the right followed by a step to the left or detecting that a user has jumped while flicking his or her wrist. Accordingly, different sets of one or more action templates may be defined for different types of activities. For example, a first set of action templates defined for basketball may include dribbling, shooting a basketball, boxing out, performing a slam dunk, sprinting and the like. A second set of action templates defined for soccer may include kicking a ball to make a shot, dribbling, stealing, heading the ball and the like. Action templates may correspond to any desired level of granularity. In some examples, a particular type of activity may include 50-60 templates. In other examples, a type of activity may correspond to 20-30 templates. Any number of templates may be defined as needed for a type of activity. In still other examples, the templates may be manually selected by a user rather than being selected by the system.

Sensor subscriptions may allow sensor system 308 to select the sensors from which data is to be received. The sensor processing system 308 may manage subscriptions that are used at any particular time. Types of subscriptions may include force sensitive resistance data from one or more force sensitive resistors, acceleration data from one or more accelerometers, summation information over multiple sensors (e.g., summation of acceleration data, summation of force resistance data over one or more sensors, etc.), pressure maps, mean centered data, gravity adjusted sensor data, force sensitive resistance derivatives, acceleration derivatives, and the like and/or combinations thereof. In some examples, a single subscription may correspond to a summation of data from multiple sensors. For example, if a template calls for a shift in force to the forefoot region of a user's foot, a single subscription may correspond to a summation of forces of all sensors in the forefoot region. Alternatively or additionally, force data for each of the forefoot force sensors may correspond to a distinct subscription.

For example, if sensor system 308 includes 4 force sensitive resistive sensors and an accelerometer, the subscriptions may specify which of those 5 sensors are monitored for sensor data. In another example, subscriptions may specify receiving/monitoring sensor data from a right shoe accelerometer but not a left shoe accelerometer. In yet another example, a subscription may include monitoring data from a wrist-worn sensor but not a heart rate sensor. Subscriptions may also specify sensor thresholds to adjust the sensitivity of a sensor system's event detection process. Thus, in some activities, sensor system 308 may be instructed to detect all force peaks above a first specified threshold. For other activities, sensor system 308 may be instructed to detect all force peaks above a second specified threshold. Use of different sensor subscriptions may help a sensor system to conserve power if some sensor readings are not needed for a particular activity. Accordingly, different activities and activity types may use different sensor subscriptions.

Sensor processing system 308 may be configured to perform initial processing of raw sensor data to detect various granular events. Examples of events may include a foot strike or launch when jumping, a maximum acceleration during a time period, etc. Sensor system 308 may then pass events to computer 102 for comparison to various templates to determine whether an action has been performed. For example, sensor system 308 may identify one or more events and wirelessly communicate BLUETOOTH® Low Energy (BLE) packets, or other types of data, to computer 102. In another example, sensor system 308 may instead or additionally send raw sensor data.

Subsequent to receipt of the events and/or the raw sensor data, computer 102 may perform post-match processing including determining various activity metrics such as repetitions, air-time, speed, distance and the like. Activity classification may be performed by identifying various events and actions represented within data received from any number and type of sensors. Accordingly, activity tracking and monitoring may include determining whether one or more expected or known actions within an activity type has been performed and metrics associated with those actions. In one example, actions may correspond to a series of one or more low-level or granular events and may be detected using predefined action templates.

For example, using action templates, computer 102 may automatically detect when a user has performed a particular activity or a particular motion expected during that activity. If a user is playing basketball, for instance, detecting that the user has jumped while flicking his or her wrist may indicate that the user has taken a shot. In another example, detecting that a user has moved both feet outward while jumping followed by moving both feet inward while jumping may register as a user performing one repetition of a jumping jack exercise. A variety of other templates may be defined as desired to identify particular types of activities, actions or movements within types of activities.

FIGS. 4A-B illustrate examples of pod sensors 304 that may be embedded and removed from a shoe in accordance with example embodiments. The pod sensor 304 may include a rechargeable battery that may be recharged when inserted into a wall adapter 402. Wired or wireless charging of the pod sensor 304 may be used. For example, the pod sensor 304 may be inductively charged. In some examples, a pod sensor 304-1 may be configured with an interface (e.g., Universal Serial Bus) permitting insertion into a computer or other device for downloading and/or receiving data. An interface of the pod sensor may provide for wired or wireless communication. For instance, software updates may be loaded onto the pod sensor when connected to a computer. Also, the pod sensor may wirelessly receive software updates. When physically coupled to a computer 102 (or other device having a port), the pod sensor may charge and communicate with the computer 102.

Figure 5:
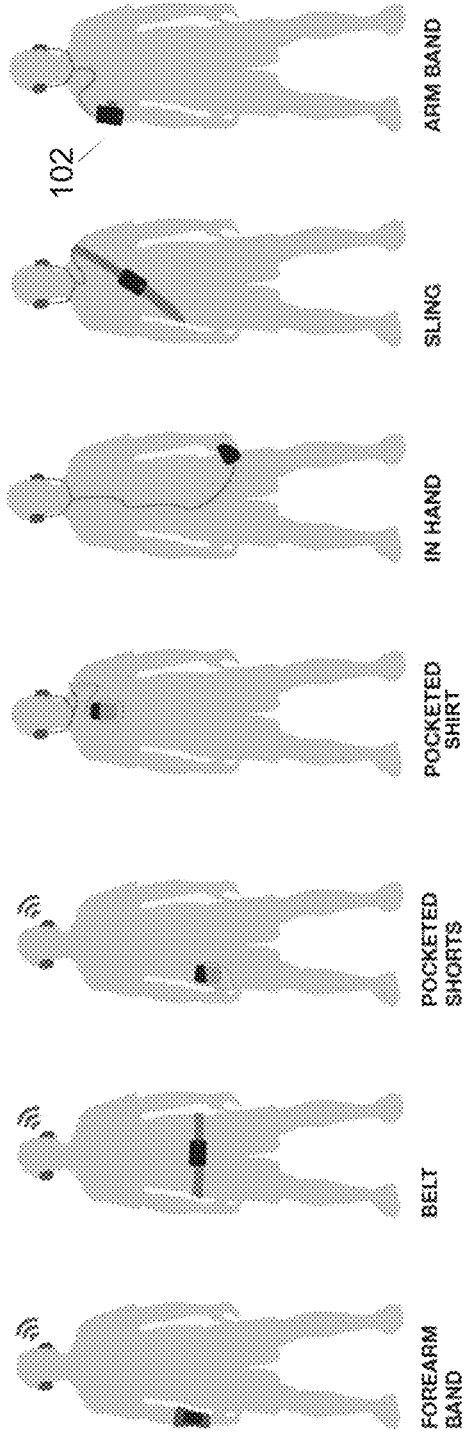
FIG. 5 illustrates example on-body configurations for a computer in accordance with example embodiments.

FIG. 5 illustrates example on-body configurations for the computer 102 in accordance with example embodiments. Computer 102 may be configured to be worn at desired locations on a user's body, such as, for example, a user's arm, leg, or chest, or otherwise integrated in clothing. For example, each article of clothing may have its own integrated computer. The computer may be a thin client, driven by the context, of what the user is doing and otherwise equipped/networked. Computer 102 may also be located apart from the user's body, as shown in FIGS. 6-7.

Figure 7:
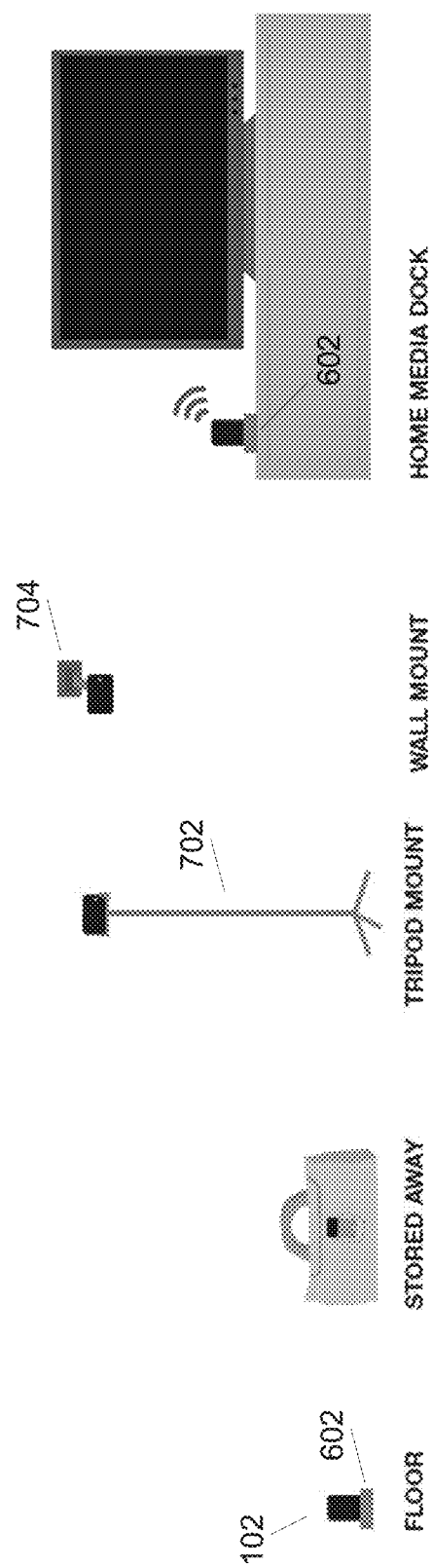

FIGS. 6-7 illustrates example various off-body configurations for the computer 102 in accordance with example embodiments. Computer 102 may be placed in a docking station 602 to permit display of the GUI on a larger screen and output of audio through a stereo system. As in other examples, computer 102 may respond to voice commands, via direct user input (e.g., using a keyboard), via input from a remote control, or other manners to receive user commands. Other off-body configurations may include placing the computer 102 on a floor or table nearby where a user is exercising, storing the computer 102 in a workout bag or other storage container, placing the computer 102 on a tripod mount 702, and placing the computer 102 on a wall mount 704. Other off-body configurations may also be used. When worn off-body, a user may wear head-phone, ear buds, a wrist-worn device, etc. that may provide the user with real-time updates. The pod sensor 304 and/or the distributed sensor 306 may wirelessly communicate with the computer 102 at the off-body locations when in range, at periodic time intervals, when triggered by the user, and/or may store data and upload the data to the computer 102 when in range or when instructed by the user at a later time.

Figure 8:
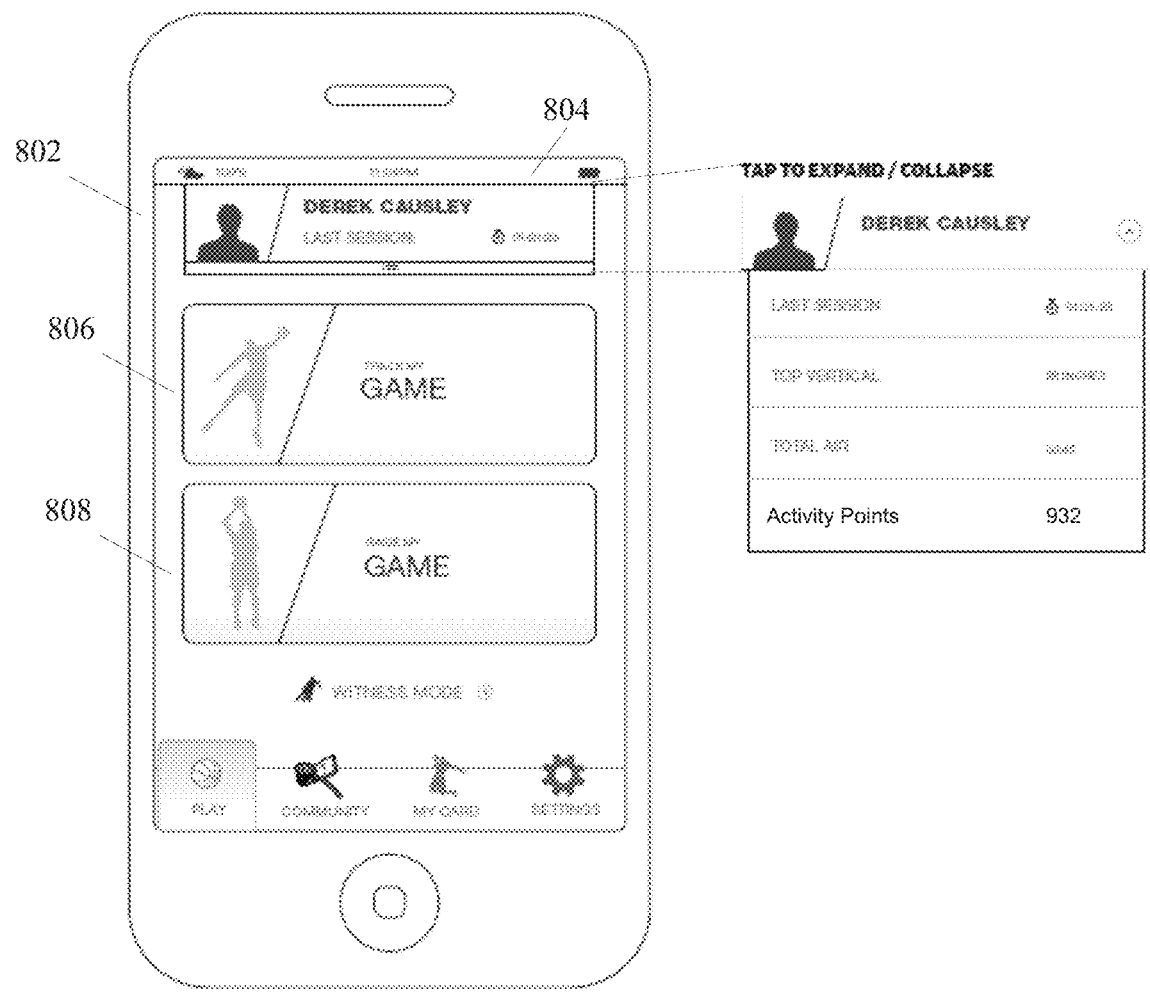
FIG. 8 illustrates an example display of a graphical user interface (GUI) presented by a display screen of a computer in accordance with example embodiments.

In an example, the user may interact with a graphical user interface (GUI) of the computer 102. FIG. 8 illustrates an example display of a GUI presented by a display screen of the computer 102 in accordance with example embodiments. Home page display 802 of the GUI may present a home page to provide the user with general information, to prompt the user to select what type of physical activity session the user is interested in performing, and to permit the user to retrieve information about previously completed sessions (e.g., basketball games, workouts, etc.). The display screen of the computer 102 may be touch sensitive and/or may receive user input through a keyboard or other input means. For instance, the user may tap a display screen or provide other input to cause the computer 102 to perform operations.

To obtain information about a previous session, the user may tap or otherwise select on a field 804 including the last session to cause the computer 102 to update the home page display 802 to display performance metrics (e.g., vertical leap, total air, activity points, etc.) from at least one previous session. For example, the selected field 804 may expand, as seen in FIG. 8, to display information about duration of the last session, the user's top vertical leap, a total amount of time a user was in the air during the last session, and incentive points (e.g., activity points) earned in the previous session. The computer 102 may determine performance metrics (e.g., speed, vertical leap, etc.) by processing data sensed by the sensors 304 and 306 or other sensing devices.

Home page display 802 may prompt a user to select whether they wish to have the computer 102 track one or more user performance metrics during a workout or athletic activity session (e.g., track my game) by selecting field 806 or assist the user in improving their athletic skills (e.g., raise my game) by selecting field 808. FIGS. 9-21 discuss the former and FIGS. 22-31 discuss the latter.

FIG. 9 illustrates example performance metrics for user selection in accordance with example embodiments. In an example, a user may be interested in monitoring their total play time, vertical leap, distance, and calories burned and/or other metrics, and may use the home page display 802 to select from the desired metrics shown in FIG. 9. The metrics may also vary based on type of athletic activity performed in a session. For example, home page display 802 may present certain default performance metric selections, depending on the activity of the session. The user may provide input to change the default performance metric selections.

Other performance metrics than the ones shown in FIG. 9 may include a total number of jumps, a number of vertical jumps above a certain height (e.g., above 3 inches), a number of sprints (e.g., speed above a certain rate, either user selected or specified by computer 102), a number of fakes (e.g., quick changes in direction), a jump recovery (e.g., a fastest time between two jumps), a work rate (e.g., may be a function of average power multiplied by time length of workout session), a work rate level (e.g., low, medium, high), total steps, steps per unit time (e.g., per minute), number of bursts (e.g., number of times a user exceeds a speed threshold), balance, weight distribution (e.g., compare weight measured by a FSR 206 in a user's left shoe to weight measured by a FSR 206 in a user's right shoe, as well as amount FRSs 206 in one shoe), average time duration of sessions, total session time, average number of repetitions per exercise, average number of points earned per session, total number of points, number of calories burned, or other performance metrics. Additional performance metrics may also be used.

In an example, computer 102 may prompt the use to indicate which metrics to monitor for each type of session (e.g., baseball, soccer, basketball, etc.) and store the identified metrics in a user profile. Computer 102 may also prompt the user for desired metrics at the beginning of each session. Further, computer 102 may track all of the performance metrics, but may only display the selected metrics to the user in the GUI. For example, computer 102 may only monitor certain base metrics (e.g., based on battery life may be extended, to vary responsiveness, to avoid data overload, etc.). If the user desires to review metrics other than the ones currently displayed by the GUI, the user may input the desired metrics and the computer 102 may update the GUI accordingly. The metrics being displayed may be changed at any time. The default metrics may be presented once the session resumes or another session begins.

If computer 102 monitors more metrics than can be displayed, computer 102 may later go into a lower level of monitoring (e.g., as resources are consumed together with warnings to user), down to and through base and ultimately to one or no metrics being monitored. In an example, computer 102 may only display base metrics for a user, unless/until configured otherwise by user. Based on resources, computer 102 may reduce what is being displayed to only present the base performance metrics or fewer metrics. Sensors may continue to monitor the other performance metrics, and data from these sensors may be later available (e.g., via web experience, etc.).

At the beginning of a session, computer 102 may calibrate the sensors of the shoes. FIGS. 10A-C and 11A-B illustrate an example of calibrating sensors in accordance with example embodiments. Calibration may involve computer 102 confirming ability to communicate directly or indirectly with the sensors (e.g., sensors 304 and 306), that the sensors are functioning properly, that the sensors have adequate battery life, and to establish baseline data. For example, computer 102 may communicate with (e.g., send a wireless signal) pod sensor 304 and distributed sensor 306 contained with a user's shoes. The pod sensor and the distributed sensor may reply with the requested data. Calibration may also occur at other time instances (e.g., mid-session, at the end of a session, etc.).

Figure 11D:
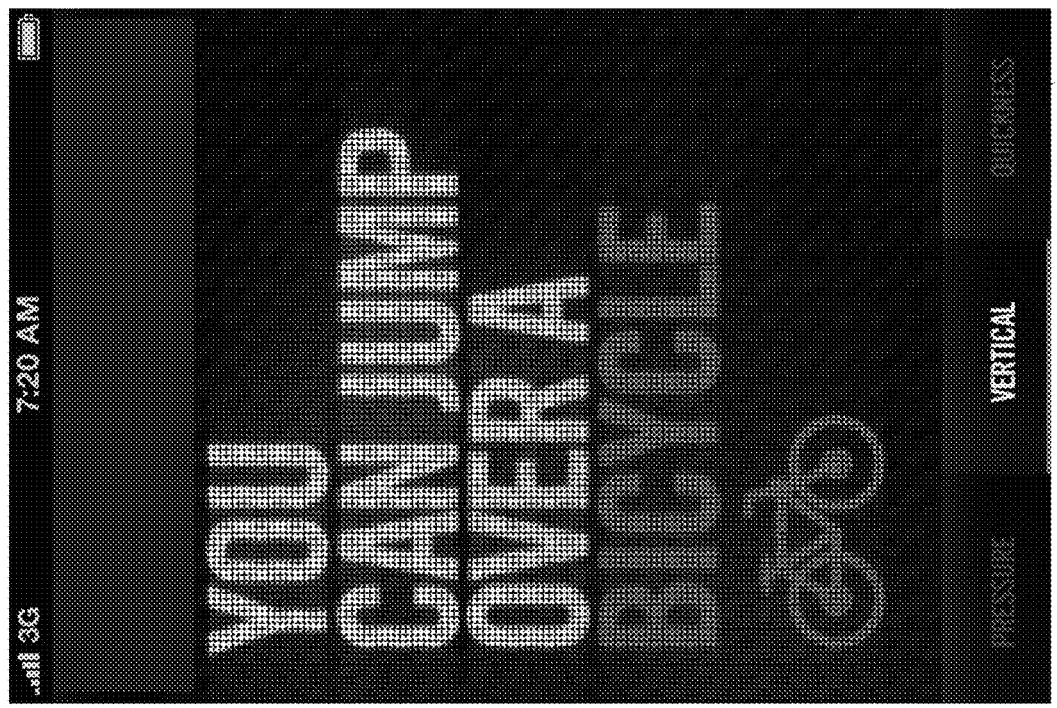
FIGS. 11C-D illustrate example displays of a GUI presenting information relating to an example calibration of sensors in accordance with example embodiments.
Figure 11C:
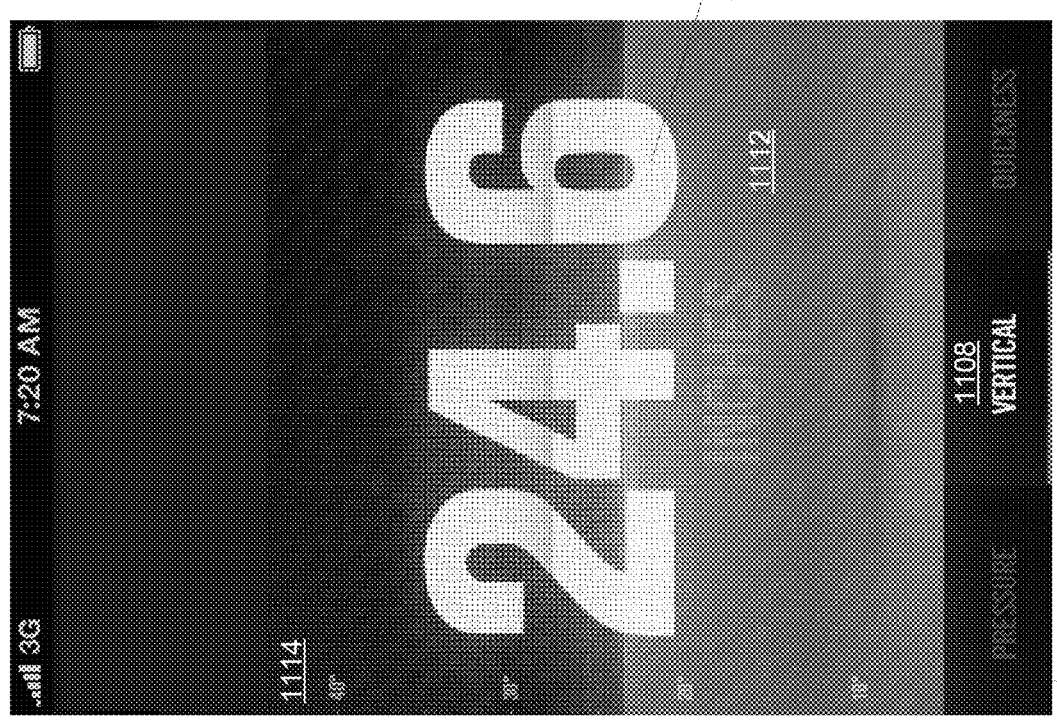
Figure 12A:
FIGS. 12A-D illustrate example displays of a GUI presenting information relative to a session in accordance with example embodiments.
Figure 12B:
Figure 12C:
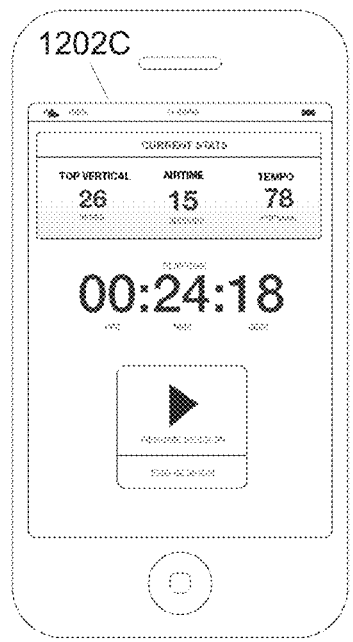
Figure 12D:

During calibration, the GUI may prompt the user to stand still to take baseline data measurements with pod sensor 304 and distributed sensor 306 (e.g., acceleration, weight distribution, total weight, etc.), as seen in displays 1002A-B. Calibration may also prompt the user to individually lift their feet to permit computer 102 to determine which foot is associated with which sensor data. Distributed sensor 306 may also be encoded with footwear information, such as, for example, shoe type, color, size, which foot (e.g., left or right), etc., that the computer 102 obtains during calibration. The computer 102 (or server 134) may process the reply from the sensors 304 and 306, and update the GUI to inform the user of any issues and how to address those issues (e.g., change battery, etc.) or if the calibration was successful, as seen in display 1002C. In FIG. 11A, for instance, field 1104 shown to the left of display 1102A includes example displays of battery life as well as connectivity status (e.g., connected, not connected). Calibration may also occur at certain events, such as detecting removal of a pod 304. Based on the calibration, the display 1102B, as shown in FIG. 11B, presents a weight distribution for the user and a gauge 1106 representing remaining battery life. Either as part of calibrating one or more sensors and/or as a separate feature or function, a GUI may be configured to display performance data in substantially real-time (e.g., as fast as may be permitted to capture (and/or process) and transmit the data for display). FIGS. 11C-D show example GUIs that may be implemented in accordance with one embodiment. As seen in FIG. 11C, display 1102C may provide one or more selectable activity parameters for displaying captured values relating to that selectable parameter. For example, a user desiring to view values relating to their vertical height during a jump may select the "vertical" icon (see icon 1108); yet other icons may include, but are not limited to: quickness (which may display values relating to steps per second and/or distance per second), pressure, and/or any other detectable parameter. In other embodiments, a plurality of different parameters may be selected for simultaneous display. Yet in further embodiments, the parameters are not required to be selected. Default parameters may be displayed absent a user input. Data relating to the parameter(s) may be provided on display 1102C in real-time. For example, output 1110 indicates that the user has jumped "24.6 INCHES". Values may be provided graphically, such as for example represented by graph 112 indicating the value is 24.6 inches. In certain embodiments, outputting of values, such as through outputs 1110 and/or 1112, may show the real-time data, in yet other embodiments, at least one of the outputs 1110/1112 may show other values, such as historical values, desired goal values, and/or a maximum or minimum value. For example, graph 1112 may fluctuate depending on the user's current (e.g., real-time) height; however, output 1110 may display the user's highest recorded jump during that session or an all-time best. Outputting of values or results may be correlated to physical objects and/or actions. For example, upon a user jumping a vertical height within a first range, such as between 24 inches to 30 inches, they may receive an indication that they could jump over a bicycle (see, e.g., display 1102D of FIG. 11D). As another example, values relating to a user's quantity of steps per second may be correlated to those of actual animals and displayed. Those skilled in the art will appreciate that other physical objects may be utilized in accordance with different embodiments.

Computer 102 may prompt the user to start a session. FIGS. 12A-D illustrate example displays of the GUI presenting information relative to a session in accordance with example embodiments. Display 1202A may initially prompt the user to check in to a court and to start a session. The user may also input a type of the session (e.g., practice, pickup game, league, half-court game, full court game, 3 on 3, 5 on 5, etc.). Display 1202B may inform the user of a duration of the session as well as prompting the user to pause and/or end their session. Display 1202C may present current performance metrics of the user (e.g., top vertical, air time, tempo, etc.). For viewing purposes, display 1202 may present default or user-selected statistics, but a swipe or other gesture may trigger a scroll, sequencing groups of predetermined number of performance metrics (e.g., 3 or other number, based on the performance metrics that can be shown on the screen in portrait versus landscape orientation) or otherwise brings up other performance metrics.

Computer 102 may also update display 1202 when a particular event is identified. For example, if a new record (e.g., personal best) is identified (e.g., new vertical max leap), computer 1202 may at least one of update the display (e.g., color, information presented, etc.), vibrate, sound a noise indicative of the specific record (e.g., based on color change placement on shoe corresponding to a specific metric), or prompt the user that some record (e.g., any metric) has been reached. Display 1202 may also present a button for the user to select signifying that a record has been achieved. Display 1202B may prompt the user to check their performance metrics (e.g., check my stats), as further described in FIG. 13.

Figure 13:
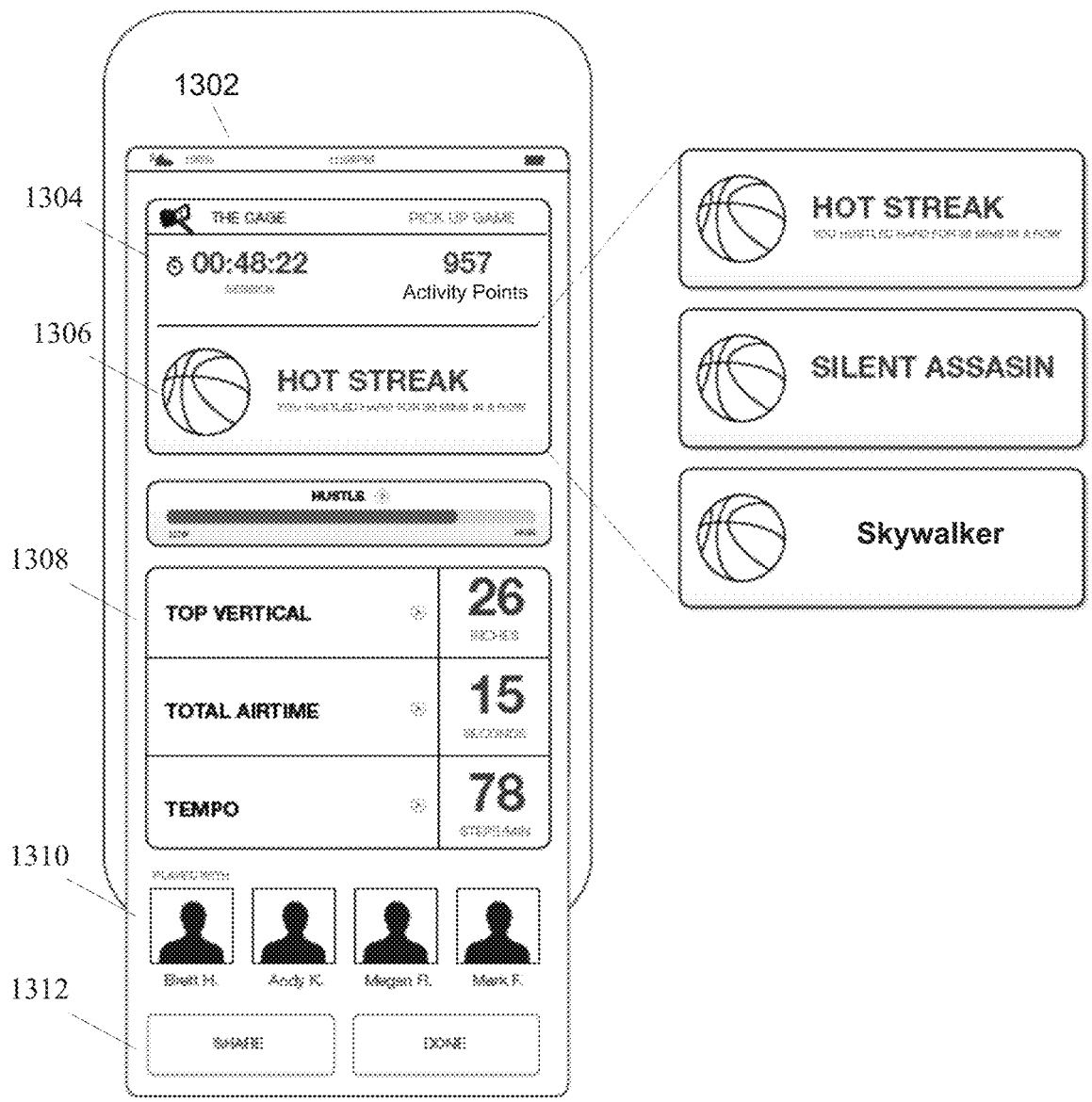
FIG. 13 illustrates an example display of a GUI providing a user with information about their performance metrics during a session in accordance with example embodiments.

FIG. 13 illustrates an example display of a GUI providing a user with information about their performance metrics during a session in accordance with example embodiments. Display 1302 may present information about a length of a current or previous session in field 1304, various performance metrics (e.g., top vertical, total airtime, tempo, etc.) for the user in field 1308, as well as who the user played with during the session in field 1310. For example, computer 102, sensor 304 or 306, or other device associated with a first user may exchange a first user identifier with a computer 102, sensor 304 or 306, or other device associated with a second user to that each computer may be aware of who participated in a session.

The computer 102 may also process the performance metrics to assign a playing style to the user as indicated in field 1306. Field 1306 may indicate that the user is a "hot streak" in response to determining that the user hustled hard for thirty minutes in a row. The box to the right of field 1306 may indicate alternative playing styles. The computer 102 may identify other types of playing styles. For example, the computer 102 may assign a 'silent assassin' playing style when identifying periods of inactivity followed by explosive bursts, a 'vortex' playing style when a user exhibits little movement or jumping during the session, a 'cobra' playing style when a user exhibits perpetual easy movement with huge bursts and jumps, a 'track star' playing style when a user is fast, has good stamina, and has a high peak speed, and a 'skywalker' playing style when a user has a big vertical leap and a long hang time. In some examples, more than one style may be assigned to the user, with a different style associated with one individual session as compared with another session. Plural styles may be assigned and displayed for a single session.

The computer 102 may assign a particular playing style based on receiving user data from at least one of pod sensor 304 (e.g., accelerometer data), distributed sensor 306 (e.g., force data), or other sensors. The computer 102 may compare the user data with playing style data for a plurality of different playing styles to determine which of the playing styles most closely matches the data. For example, the computer 102 may set performance metric thresholds for each of the playing styles. Some playing styles may require that, at least once during the session, the user jumped a certain height, ran at a certain speed, played for a certain amount of time, and/or performed other tasks. Other playing styles may require that the user data indicate that the user performed certain sequences of events (e.g., little movement followed by quick acceleration to at least a certain top speed). Some playing styles may require that the user data indicate that the user maintained thresholds for a certain amount of time (e.g., maintained average speed over a threshold throughout a game).

In an example, a playing style may be assigned based on a data set obtained from a set of sensors including sensors worn at various locations on a user's body (e.g., accelerometers at the gluteus and or upper body to identify a "BANGER" playing style). Also, other, non-activity data may come into determining a playing style, such as user profile data (e.g., user age, height, gender, etc.). For example, some playing styles may be gender specific or based on ambient conditions (e.g., a "POSTMAN" style because use plays in rain, sleet, snow, etc.).

A user or user group may define their own playing styles, based on a combination of metrics and analytics. The users or user groups may change a name of the playing style, without changing the associated metrics and analytics. Playing styles may be updated automatically. For example, personal training system 100 may periodically update a playing style specified by system 100. In another example, system 100 may automatically update a playing style when the name of the playing style is associated with a particular location (e.g., state, city, court), and that playing style is referred to by a different name at another location (e.g., keep the designation consistent with local lingo).

In FIG. 13, display 1302 permits the user to share their performance metrics with other users and/or to post to a social networking website by selecting field 1312. The user may also input a message (e.g., "check out my vertical leap") to accompany the performance metrics being sent. The computer 102 may distribute performance metric data of a current and/or previous session and the message to the server 134 in response to a user request to share. The server 134 may incorporate the data and/or message in the social networking website and/or may distribute the data/message to other desired or all users.

Figure 14C:
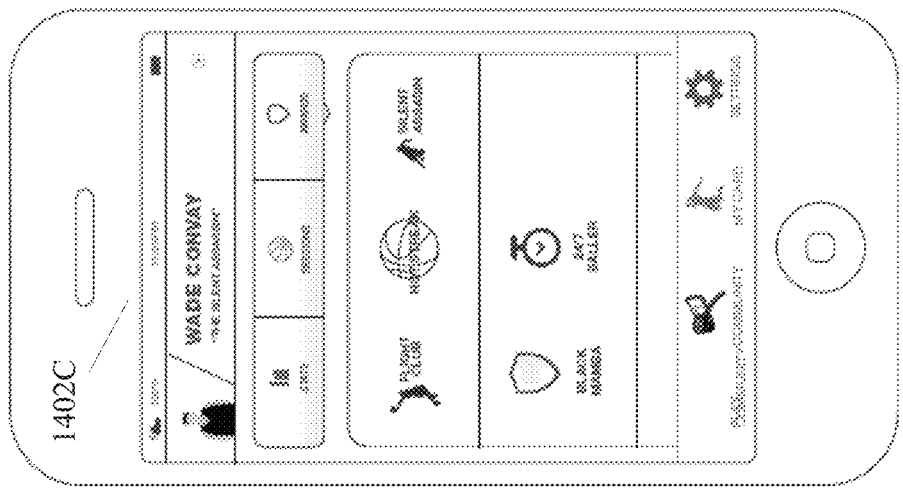
FIGS. 14A-C illustrate example displays of a GUI presenting information about a user's virtual card (vcard) in accordance with example embodiments.
Figure 14B:
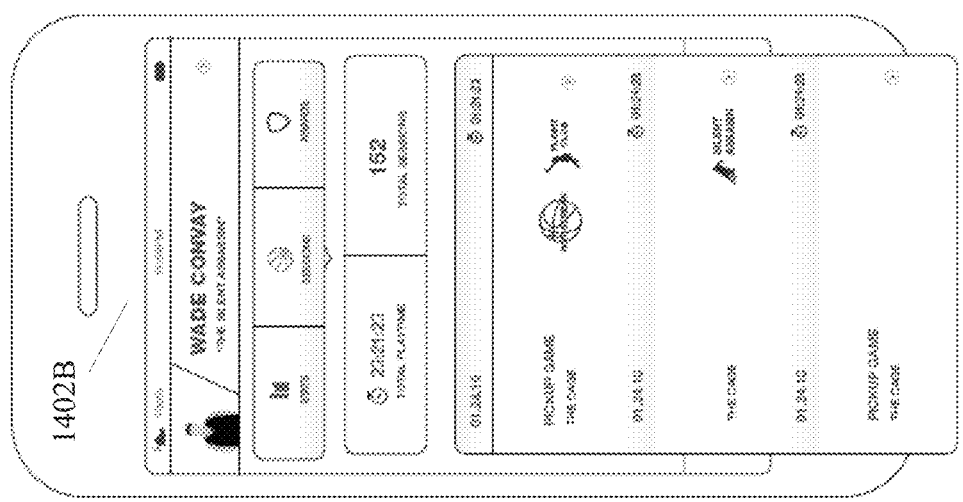
Figure 14A:
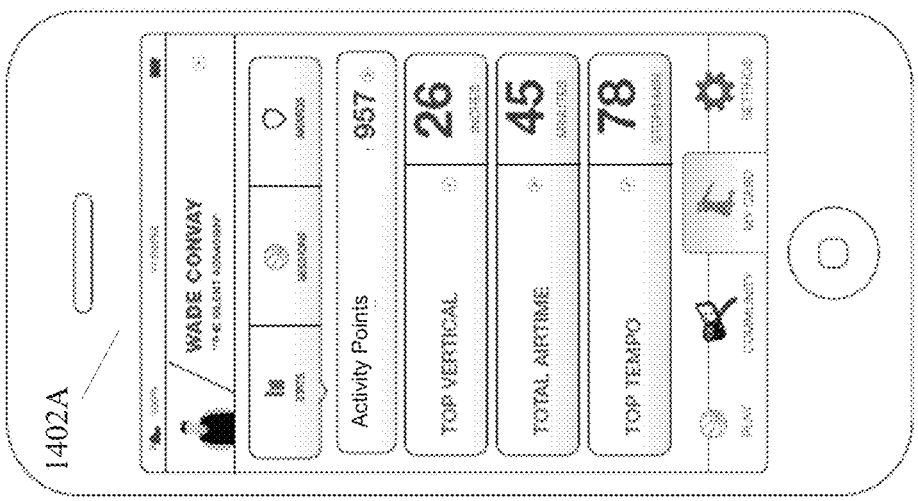

FIG. 14A-C illustrates example displays of the GUI presenting information about a user's virtual card (vcard) in accordance with example embodiments. The vcard may include information about a user's athletic history. The vcard may include data on a user's performance metrics, sessions, and awards at individual sessions as well as averages of the performance metrics. The vcard statistics display 1402A may indicate a number of points a user has acquired (e.g., activity points or metrics), as well as running totals and/or top performances by the user. The activity points may a statistic indicating physical activity performed by a user. The server 134 and/or computer 102 may award activity points to the user upon achieving certain athletic milestones. The vcard sessions display 1402B may indicate a total amount of playtime and number of sessions a user has completed, as well as providing historical information about completed sessions. The vcard sessions display 1402B may also indicate a playing style the user exhibited for each session as well as a session length and date of the session. The vcard awards display 1402C may indicate awards the user has accrued over time. For example, the server 134 and/or computer 102 may award the user a flight club award after accruing a total amount of loft time during the sessions.

Other example awards may be a "king of the court" award for a user who has one or more top metrics at a specific court, a "flier mile" award earned with one mile of flight time (or for other quanta of time and distance), a "worldwide wes" award when a player participates in sessions in multiple countries, an "ankle-breaker" award to those having at least a certain top speed or quickest first step, a "jump king" award for a user having at least a certain vertical leap, a "24/7 baller" award for a user who plays a certain number of days in a row or at a certain number of different courts, an "ice man" award if a certain number of rivals follow a user, a "black mamba" award if an even greater number of rivals follow a user (compared to an ice-man), a "prodigy" award for a young player achieving certain performance metric levels, and an "old school" award for older players achieving certain performance metric levels. Other types of awards may also be awarded.

Figure 15:
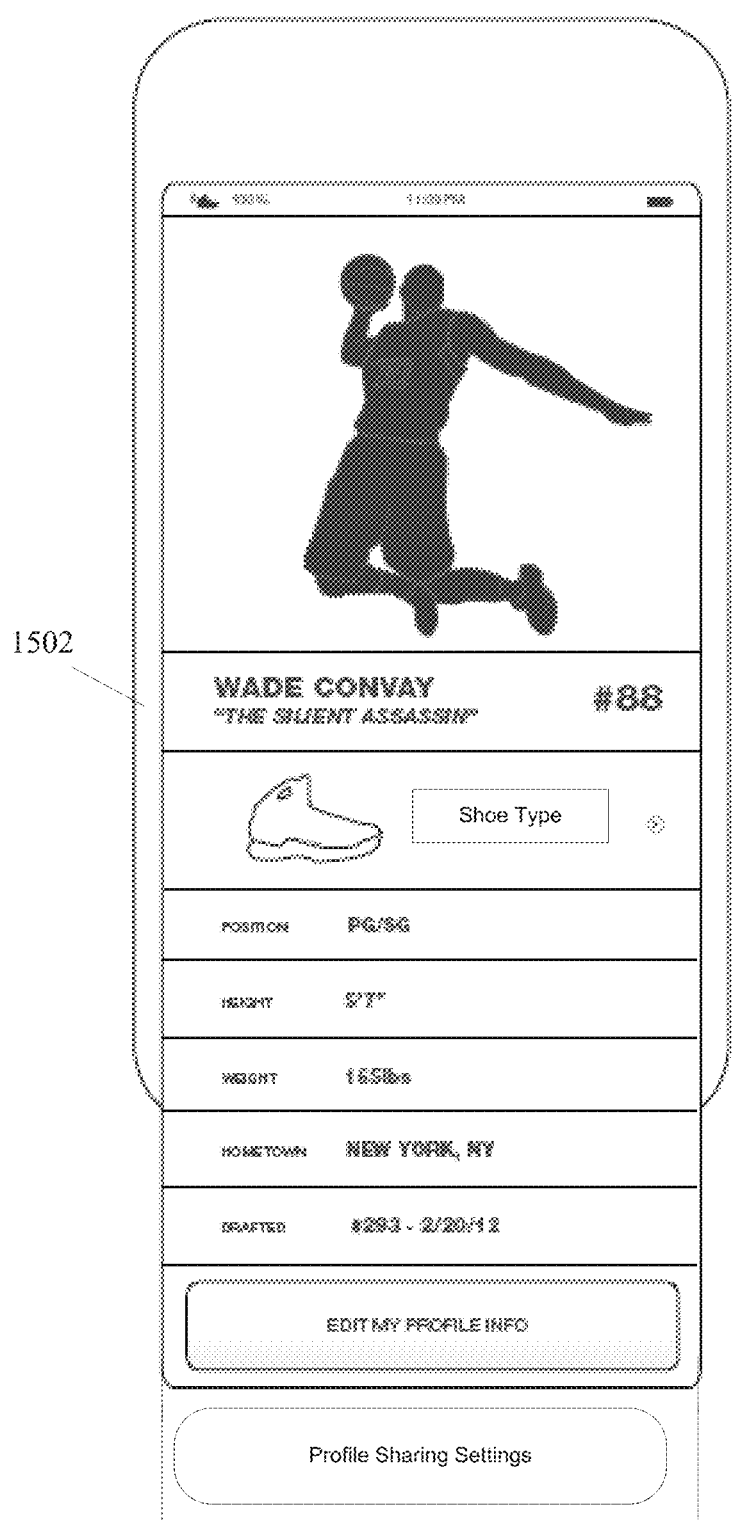
FIG. 15 illustrates an example user profile display of a GUI presenting a user profile in accordance with example embodiments.
Figure 16:
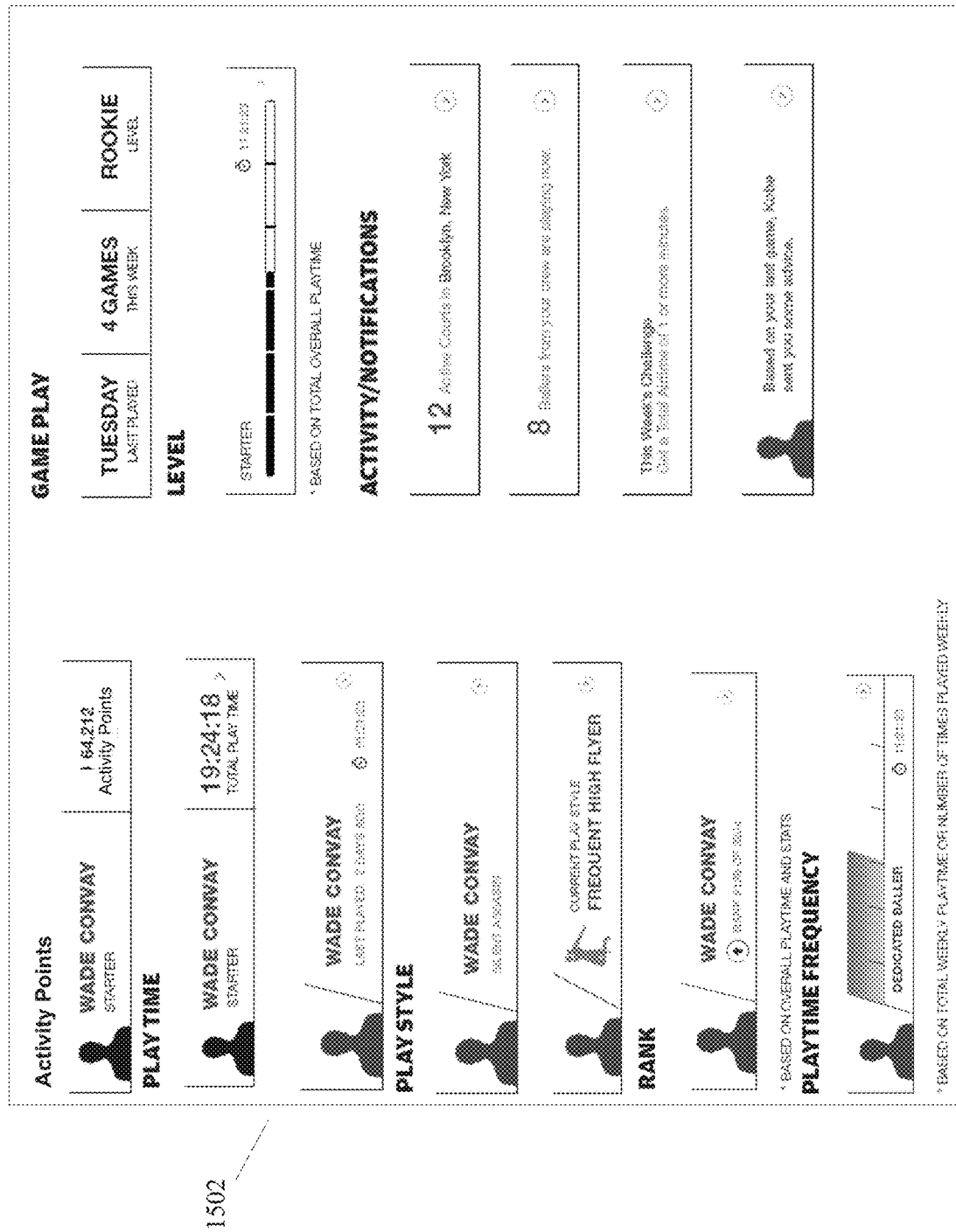
FIG. 16 illustrates a further example of user profile display presenting additional information about the user in accordance with example embodiments.

FIG. 15 illustrates an example user profile display of the GUI presenting a user profile in accordance with example embodiments. The user profile display 1502 may present information about the user, such as height, weight, and position, playing style (e.g., "The Silent Assassin"), as well as other information. The user profile display 1502 may also indicate one or more types of shoe worn by the user. The user profile display 1502 may present information about the user's activity, and may permit the user to control sharing this information with other users. For example, the user may specify which other users can view user profile information, or may make all of the user's information accessible to any other user. FIG. 16 illustrates further examples of information about the user that may be presented in user profile display 1502 in accordance with example embodiments.

FIGS. 17A-D, 18A-C, 19A-D and 20A-B illustrate further example displays of a GUI for displaying performance metrics to a user in accordance with example embodiments. During, at the end of a session, or both, the computer 102 may communicate with at least one of pod sensor 304, distributed sensor 306, or other sensor, to obtain data to generate the performance metrics. Example displays of the GUI while capturing data are shown in FIGS. 17A-D, such as top vertical in display 1702A, total airtime in display 1702B, tempo statistics in display 1702C, and points in display 1702D. Scroll bar 1704 represents the progress in transferring data from the sensors to computer 102.

Figure 18B:
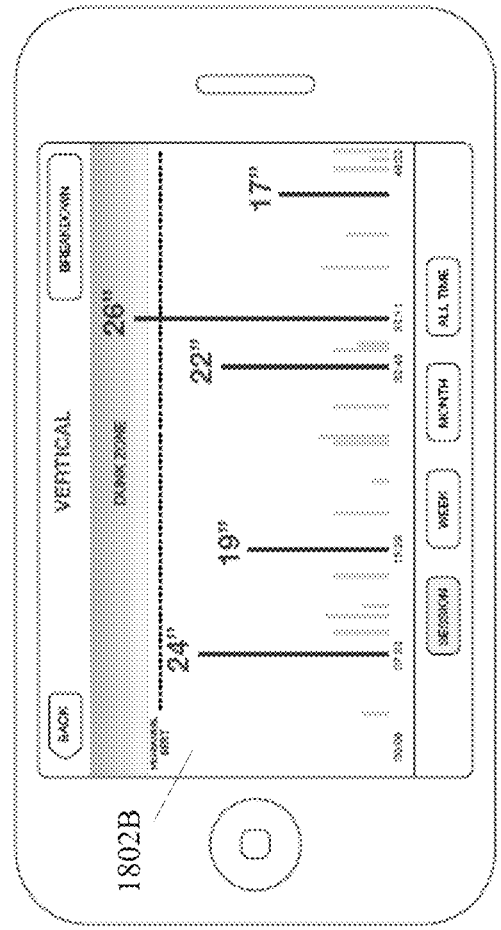
FIGS. 18A-C illustrate further example displays of a GUI for displaying performance metrics to a user in accordance with example embodiments
Figure 18A:
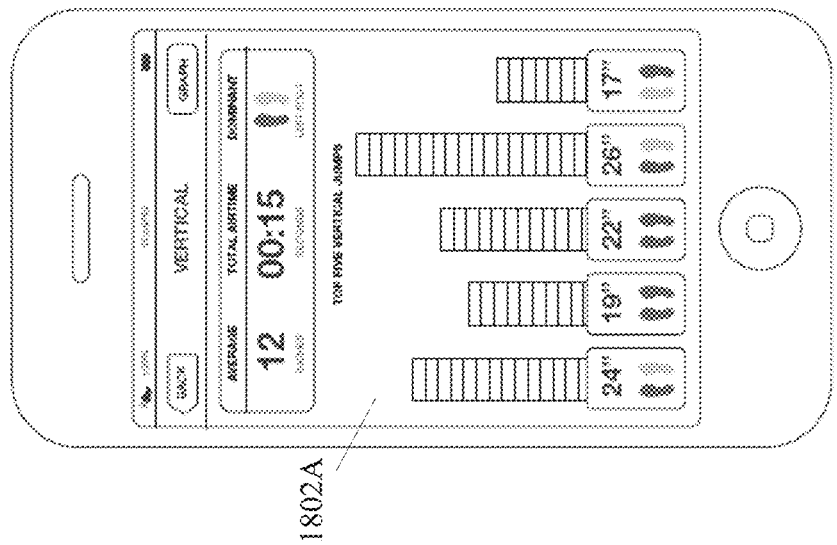

FIGS. 18A-B illustrate example leap displays relating to a user's vertical leap in accordance with example embodiments. The computer 102 may track information on the user's vertical leap during an exercise session as well as at what times during the session the leaps occurred. The computer 102 may determine a user's vertical leap based on an amount of loft time between when both feet of a user leave the ground and when a first of the user's feet next contacts the ground. The computer 102 may process accelerometer data from pod sensor 304 and/or force data from distributed sensor 306 to determine a moment when both of the user's feet are off the ground and when a first of the feet next contacts the ground. The computer 102 may also compare user data from pod sensor 304 and distributed sensor 306 with jump data to confirm that the user actually jumped and landed, rather than merely lifted their feet off of the ground or hung on a basketball rim (or other object) for a predetermined time. The jump data may be data generated to indicate what a force profile and/or acceleration profile should look like for someone who actually jumped. The computer 102 may use a similarity metric when comparing the user data to the jump data. If the user data is not sufficiently similar to the jump data, the computer 102 may determine that the user data is not a jump and may not include the user data when determining a user's performance metrics (e.g., top or average vertical leap).

Provided that the computer 102 determines that the user data is for a jump, the computer 102 may process the user data to determine a vertical leap, a time of the vertical leap, a user's average vertical leap height, maintain a running total of loft time for jumps, and/or determine which foot is dominant, as well as other metrics. The computer 102 may identify a dominant foot based on the force data and/or accelerometer data associated with each shoe. The force data and/or accelerometer data may include timing information so that the computer 102 can compare events in each shoe. The computer 102 may process the force data and/or accelerometer data as well as the timing information to determine which foot was last on the ground prior to a jump. The computer 102 may identify a dominant foot based on the one that is last on the ground when a user jumps and/or the one associated with a user's largest vertical leap. The computer 102 may also present leap display 1802A including a user's top five vertical leaps and depict which foot, or both feet, was last on the ground immediately preceding the jump. Leap display 1802A may display any desired number of top leaps, which may be specified by the user or set by system 100. The number of top leaps may be based on an amount of time. For example, leap display 1802A may present the top five leaps over the full time of a session, top five in the most recent predetermined number of minutes or percentage of total session time, or based on the type of session (e.g., pick-up basketball game as compared to an organized game). The leap display 1802A or 1802B may also display vertical leaps over durations other than by session, and may include, for example, month, week, all time, or other time ranges. Leap display 1802A or 1802B may also present a total number of jumps, a cumulative amount of hang time, an average hang time, hang time corresponding to a highest vertical leap, or other information relating to jumping. Orientation of computer 102 may control which of leap display 1802A and leap display 1802B is currently being presented. For example, a user may rotate computer 102 (e.g., 90 degrees) to change from presenting leap display 1802A (e.g., a portrait orientation) to presenting leap display 1802B (e.g., a landscape orientation). A user may rotate computer 102 in the opposite direction to change from presenting leap display 1802B to presenting leap display 1802A. Similarly, rotation of computer 102 may be used to alternate between displays in other examples described herein.

In another example, leap display 1802B may display a user's jumps chronologically over a session and may indicate a time when each jump occurred as well as vertical height for each jump during the session. The leap display 1802B may also display a user's personal best vertical leap from a previous session or previously set during the session. In an example, a personal best line can be changed during a session, either via a step function, or by adding a new line of the new best to supplement the existing line (e.g., "new best" color) and showing lines for the session in which the new best occurs. Computer 102 may also update leap display 1802B by replacing the previous personal best line (e.g., in one color) with a new line (e.g., in a new personal best color, which may only be used during the session in which the personal best occurred). Further, the color may change as the user's personal best improves to indicate ability compared to other users (e.g., you jumped higher than 85% of other users).

The leap display 1802B may include a performance zone (e.g., dunk zone) indicating when a user may be able to perform an act (e.g., dunk a basketball). The computer 102 may tailor the performance zone to the user based on the user's physical attributes (e.g., height, arm length, leg length, torso length, body length, etc.). For example, a dunk zone may require a higher vertical leap for a shorter user than a taller user.

A performance zone may correspond to a range of values, a minimum value, or a maximum value. The one or more values may correlate to when a user's athletic performance is expected that a user could perform a particular act. For example, a performance zone may be a minimum vertical leap that would permit a user to dunk a basketball. The user need not actually perform the act (e.g., dunking), but instead the performance zone may indicate when the computer 102 calculates that the user could perform the act.

Based on sensor data obtained from one or more sessions, computer 102 may provide a recommendation to help the user achieve the performance zone. For example, computer 102 analysis of sensor data associated with leaps by the user may enable more feedback to the user to enhance ability to get into the dunk zone or to improve personal bests in rare air. For instance, computer 102 may process sensor data and recommend that the user adjust certain body parts to increase the user's leaping ability. In another example, computer 102 may suggest that the user obtain greater acceleration of leading foot or more pressure on trailing foot by increasing upper body acceleration.

A performance zone may be established for any desired athletic movement. Example performance zones may correspond to a minimum amount of pressure measured by distributed sensor 306, a maximum amount of pressure, pressure falling within a particular range or pressures. Other example performance zones may correspond to a minimum amount of acceleration measured by the sensor 306, a maximum amount of pressure, pressure falling within a particular range or pressures. Also, a performance zone may be based on a combination of different measurements or a sequence of measurements. For example, a performance zone may specify at least a certain amount of acceleration, followed by at least a certain amount of loft time, followed by at least a certain amount of measured pressure.

In gymnastics, for example, acceleration and body rotation may be monitored. For instance, it may be desirable for a gymnast to have a specific amount of body rotation during a dismount from the uneven bars. If the gymnast rotates too quickly or slowly, he or she may not orient their body in a proper position when landing. The performance zone may be a "spin zone" specifying minimum and maximum rotational accelerations, and computer 102 may monitor for over and under rotation to provide the gymnast with feedback on whether they are within a performance zone during a dismount. Computer 102 may provide a recommendation to adjust certain body parts to adjust an amount of acceleration when dismounting to increase or decrease rotation by the user. A performance zone may be established for other sports (e.g., track and field, golf, etc.).

Computer 102 may tailor the performance zone based on feedback received form the user. In an example, computer 102 may receive input from a user indicating for which vertical leaps the user was able to perform the act (e.g., dunk a basketball), and the computer 102 may adjust a minimum required vertical leap for the user to be in the performance zone based on the user's feedback. Computer 102 may award one or more activity points to a user for being in the performance zone as well as for the amount of time the user maintained their performance within the performance zone. Computer 102 may also determine an amount of calories burned by the user while in the performance zone.

Figure 18C:
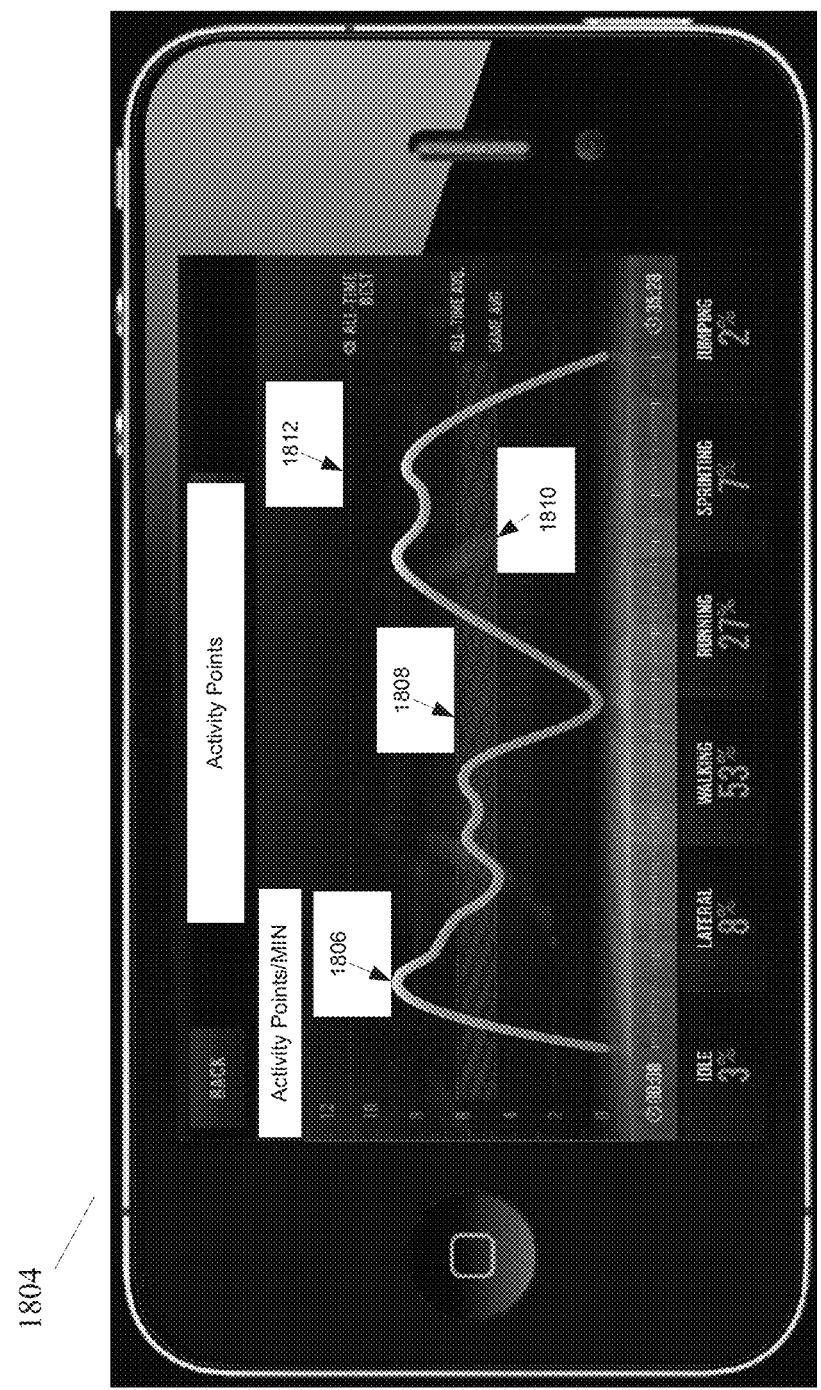
Figure 19B:
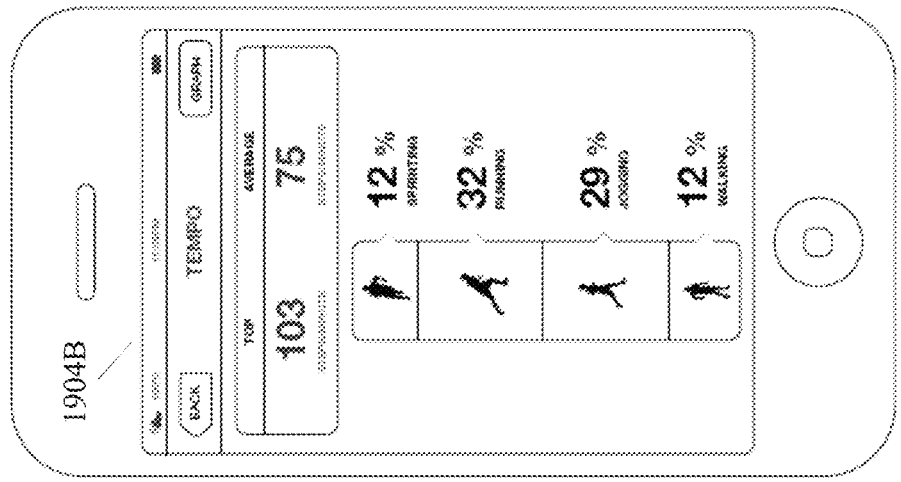
FIGS. 19A-D illustrate further example displays of a GUI for displaying performance metrics to a user in accordance with example embodiments
Figure 19A:
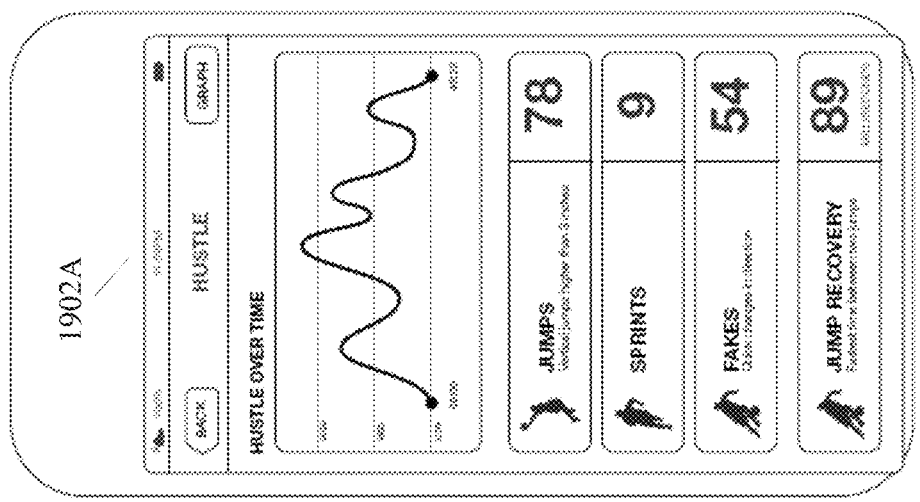
Figure 19C:
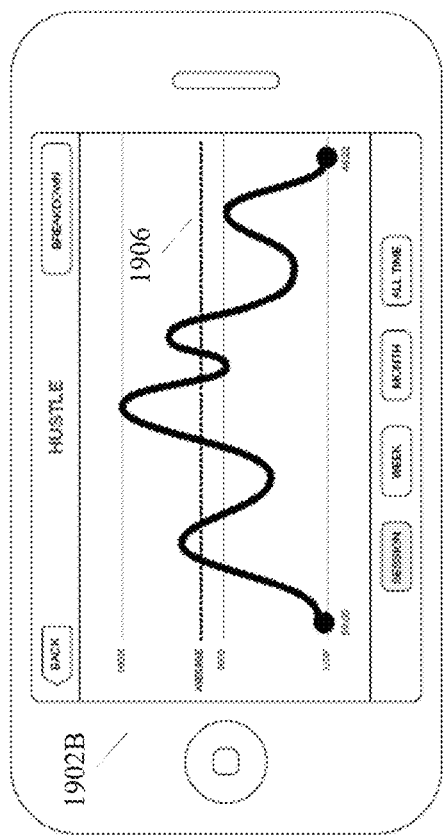
Figure 19D:
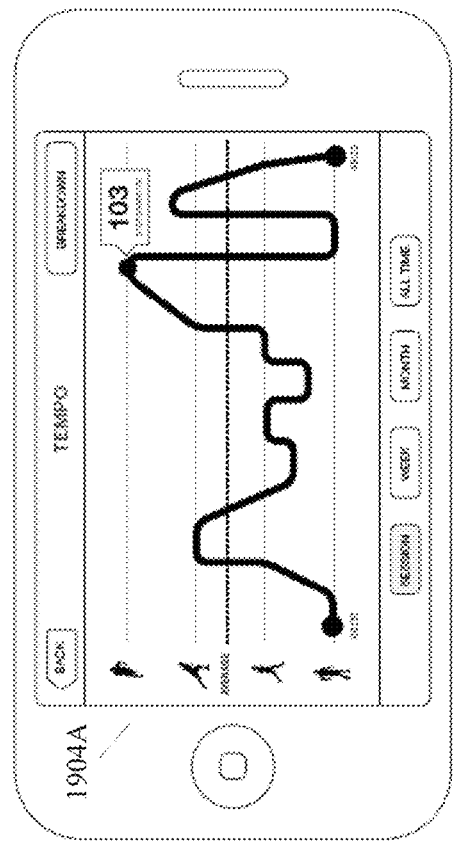

Computer 102 may present information indicating a rate of activity points earned by a user over the duration of an exercise session. FIG. 18C illustrates an example activity points display 1804 in accordance with example embodiments. Computer 102 may determine and award activity points to a user during the exercise session. To do so, computer 102 may compare measured user performance to any number of metrics to award activity points. For example, computer 102 may award a predetermined number of activity point for running a predetermined distance. As may be seen in FIG. 18C, line 1806 of activity points display 1804 may represent the rate at which a user earned activity points at various times during the exercise session, line 1806 may represent an all-time average rate at which a user has accrued activity points, line 1808 may represent the average rate at which the user accrued activity points during this particular session, and line 1812 may represent an all-time best rate for accruing activity points. In an example, line 1806 may represent how may activity points a user accrues per minute, or other interval of time (e.g., per millisecond, per second, per ten seconds, per thirty seconds, etc.). Activity points display 1804 may also present indicia, such as lines, indicating other matrices, such as averages, including but not limited to an average rate of accrued activity points for a predetermined number of previous session (e.g., last three sessions). Further, the lines may be of different colors. If a new all-time best is established, activity points display 1804 may flash or otherwise present an indication signifying the accomplishment.

Computer 102 may categorize activities performed by the user as well as a percentage of time during an exercise session a user was in a particular category, and present this information to the user in the activity points display 1804. For example, activity points display 1804 may indicate a percentage of time during a session that a user was idle, percentage of time that the user moved laterally, percentage of time that the user was walking, percentage of time that the user was running, percentage of time that the user was sprinting, and percentage of time that the user was jumping, etc. Other categories instead of or in addition to the ones shown in activity points display 1804 may also be presented. Further, activity points display 1804 may display a cumulative amount of time, rather than percentage of time, for each of these statistics. Computer 102 may determine that amount of activity points a user earned while in each category, as well as a total amount of activity points earned during an exercise session, and present such information via activity points display 1804. In an example, computer 102 may determine that a user earned 25 activity points while walking, 75 activity points while walking, and 150 activity points while sprinting, for a total of 250 activity points. Computer 102 may also determine a caloric burn rate for each of the categories instead of or in addition to determining activity points.

The computer 102 may also display performance metric data based on measurements of a user's hustle and tempo. FIGS. 19A-D illustrate example hustle displays 1902A-B and tempo displays 1904A-B in accordance with example embodiments. Hustle display 1902A may present a user's hustle over time during a session, as well as other performance metrics. For example, computer 102 may track various performance metrics including a running total of jumps, sprints, fakes, and jump recovery (e.g., a shortest amount of time between consecutive jumps) during a session, and hustle may be a function of these metrics. With reference to hustle display 1902B, computer 102 may divide hustle into three categories: low, medium and high. More or fewer categories of hustle may be defined. Hustle display 1902B may also present line 1906 indicating an average hustle level over a session.

With reference to tempo display 1904A, computer 102 may present information on a user's tempo during a session. Tempo may be based on a rate of steps taken by a user per interval of time (e.g., steps per minute). The categories may be defined by ranges of step rates. For example, walking may be defined as one to 30 steps per minute, jogging may be 31-50 steps per minute, running may be defined as 51-70 steps per minute, and sprinting may be defined as 71 or more steps per minute. With reference to tempo display 1904B, computer 102 may indicate how often a user was in each category during a session. For example, tempo display 1904B may indicate what percentage of the time a user was in each category (e.g., 12% sprinting). Tempo display 1904 may also indicate a user's quickest number of steps per second (e.g., 4.1 steps/second) or any other time interval, a total number of steps, a total number of sprints, etc.

Figure 20B:
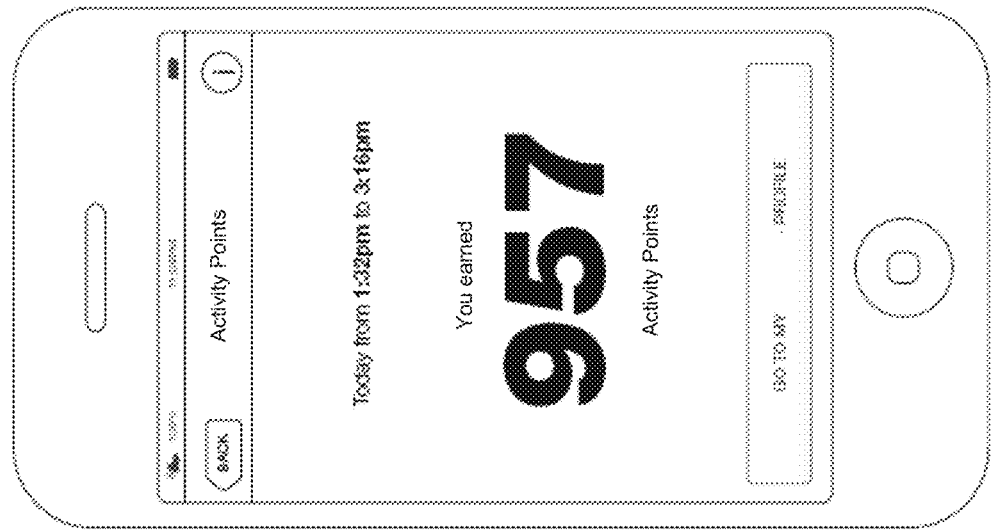
FIGS. 20A-B illustrate further example displays of a GUI for displaying performance metrics to a user in accordance with example embodiments.
Figure 20A:
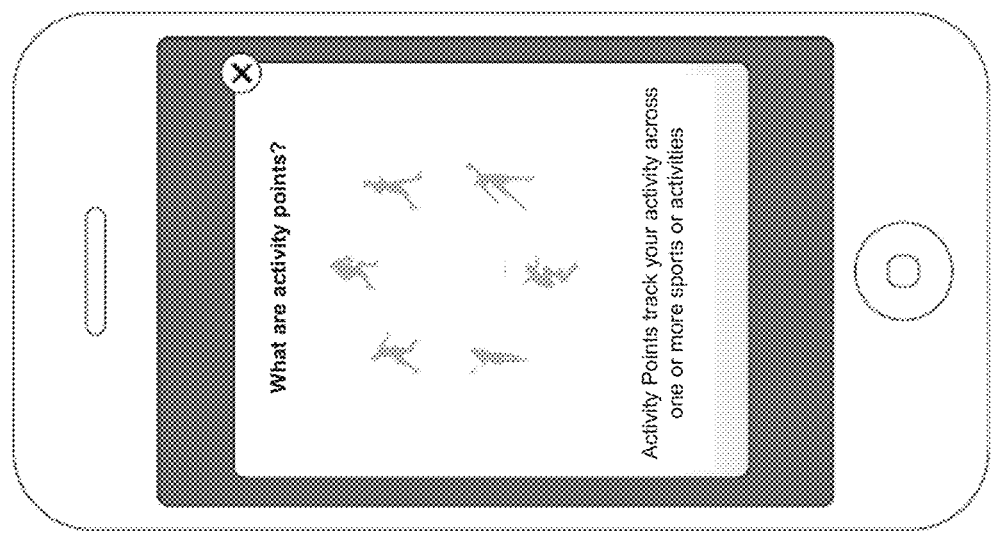

The computer 102 may also inform the user of activity points earned during the workout as well as total activity points accrued. FIGS. 20A-B illustrate example activity points displays of a GUI informing a user of points earned during a session in accordance with example embodiments. The computer 102 may process data taken during a workout session to award points to a user. The points may track a user's activity across different sports and workout sessions. The points display 2002A-B may permit the user to determine points earned by date range, workout session, or other ranges.

Figure 21C:
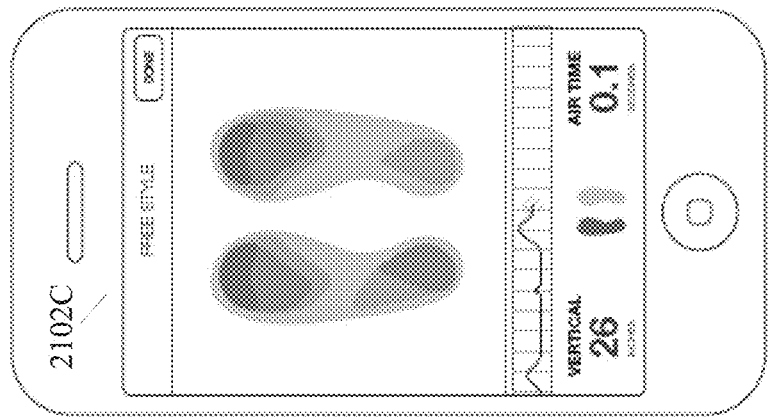
FIGS. 21A-C illustrate example freestyle displays of a GUI providing information on freestyle user movement in accordance with example embodiments.
Figure 21B:
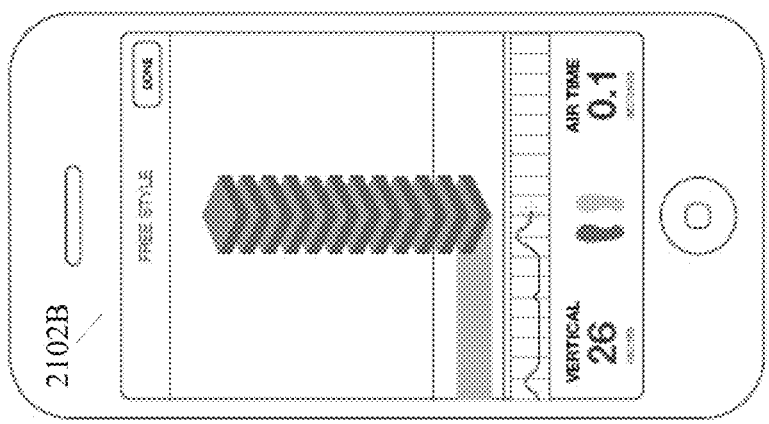
Figure 21A:
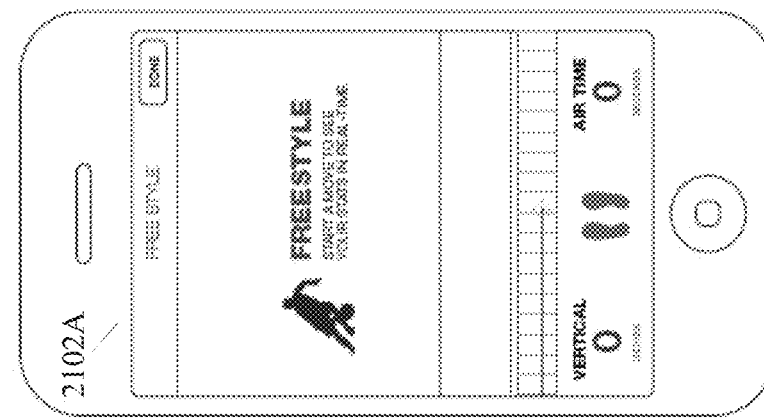

The computer 102 may also track user defined movement. FIGS. 21A-C illustrate example freestyle displays of a GUI providing information on freestyle user movement in accordance with example embodiments. In freestyle display 2102A, computer 102 may prompt the user to start a movement for tracking. The user may perform any desired type of movement, denoted hereafter as "freestyle" movement. In freestyle display 2102B, computer 102 may display a user's vertical leap, airtime, and foot used for a jump during the freestyle movement. Freestyle display 2102B may display performance metrics deemed relevant by the system 100, by the user, or both. For example, performance metrics could be the vertical leap, airtime, foot, as shown in display 2102B, could be the weight distribution shown in display 2102C, or both with the user cycling through. In freestyle display 2102C, computer 102 may display a weight distribution measured by distributed sensor 306. The user may also review weight distributions over time to determine how the user's weight distribution may have affected a user's availability to move or leap. A user may, for example, slide their finger across display to move between displays 2102A-C.

In addition to monitoring a user's performance during a session, computer 102 may assist a user in improving their athletic skills. FIGS. 22A-B illustrate example training displays 2202A-B presenting user-selectable training sessions in accordance with example embodiments. The training sessions may guide the user through a set of movements designed to improve a user's athletic ability. Example training sessions may include a shooting practice, an all around the world game, a buzzer beater game, a pro-player game, a basic game, an air time game, a continuous crossover game, a free throw balance game, a signature moves game, a pro battles game, and a horse game. These training sessions are further described in FIGS. 23-26. For example, computer 102 may have a touchscreen permitting a user to scroll between and select the training sessions shown in FIGS. 23-26.

Figure 27:
FIG. 27 illustrates a display screen for GUIs for a basketball shooting training session in accordance with example embodiments.
Figures 28A, 28B, 28C:
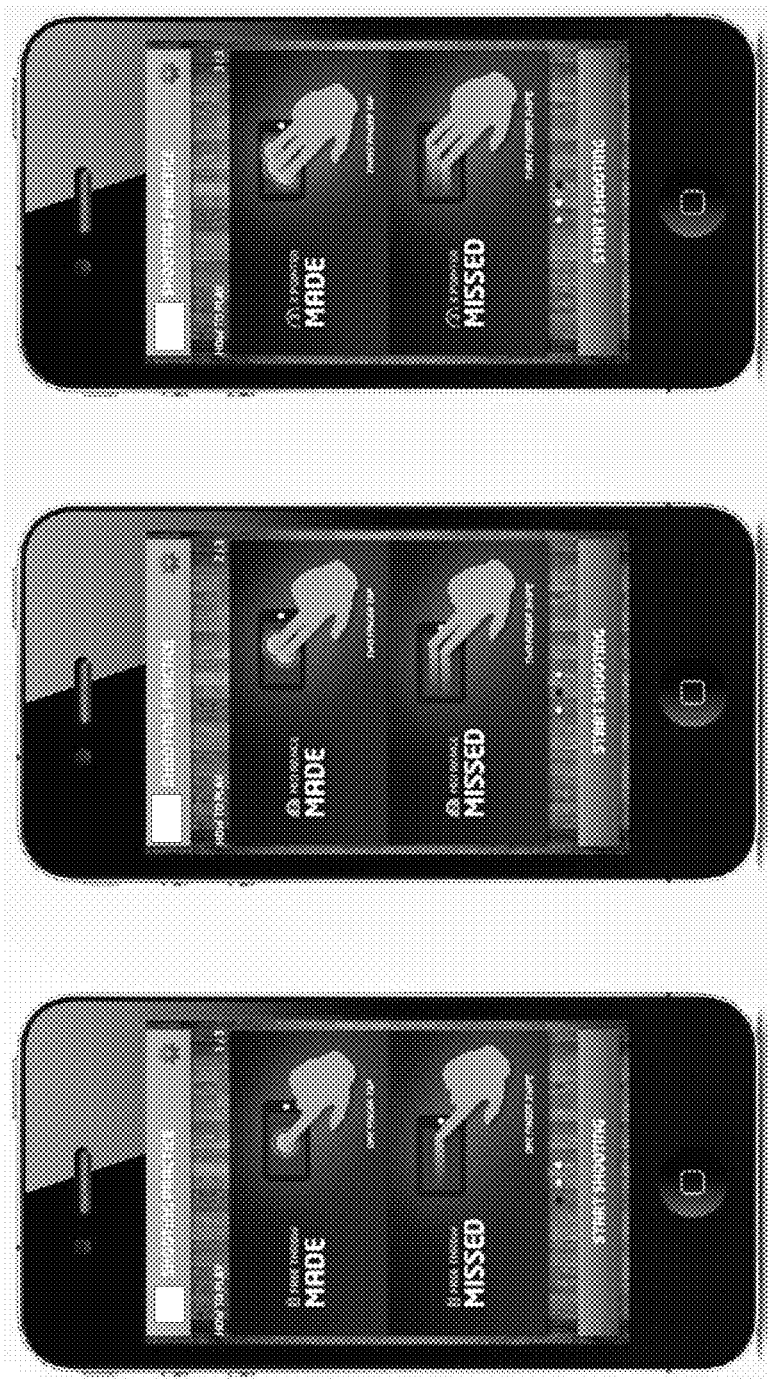
FIGS. 28A-C illustrate display screen for GUIs for a basketball shooting training session in accordance with example embodiments.

FIGS. 27, 28A-C, 29A-B, and 30A-C illustrate display screens for GUIs for a basketball shooting training session in accordance with example embodiments. In FIG. 27, training display 2702 may present the user with information on their last session (e.g., shooting percentage for free throws, three pointers, and jump shots) and prompt the user to begin a new session. The computer 102 may monitor touches on a pressure sensitive display screen to track makes and misses. To do so, the computer 102 may monitor how many fingers were used to distinguish between basketball shots. For example, three fingers may be used to indicate a three point shot in basketball, two fingers may be used to indicate a two point shot, and a single finger may be used to indicate a free throw, as seen in FIGS. 28A-C. A tap of one or more fingers on the display screen may indicate a made shot, and a swipe of one or more fingers across a portion of the display screen may indicate a miss. In other examples, a down swipe across a display screen of computer 102 with one or more fingers may indicate a make and an up swipe with one or more fingers may indicate a miss.

Figure 29B:
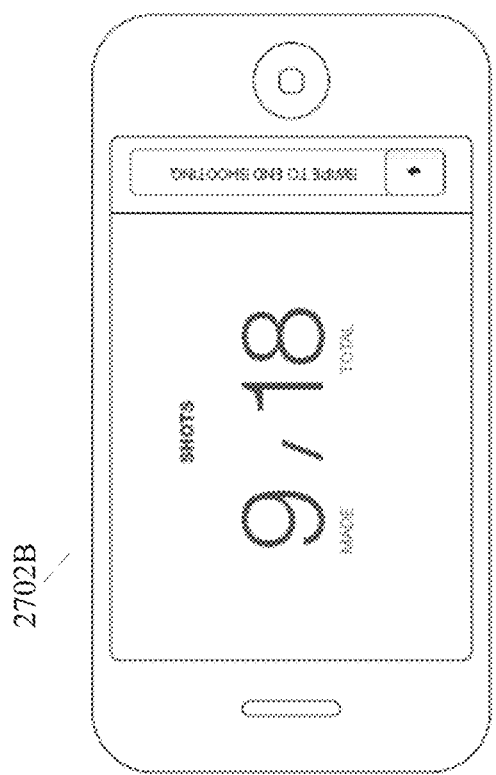
FIGS. 29A-B illustrate display screen for GUIs for a basketball shooting training session in accordance with example embodiments.
Figure 29A:
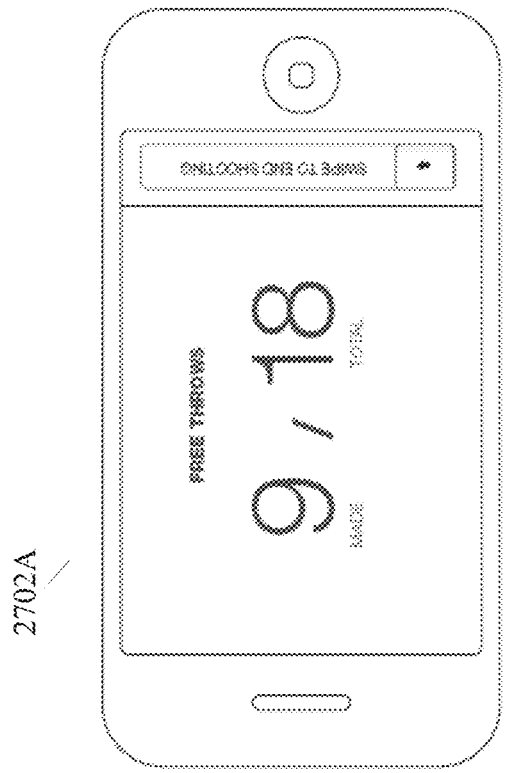

The computer 102 may process the user input to determine a number of fingers used as well as between a tap and a swipe. The computer 102 may determine an amount of area of the display screen covered by the fingers when tapping and/or swiping the display screen to distinguish between one, two, or three fingers. The computer 102 may also determine duration of the touch and if a region of the display screen initially contacted by the user differs from a region of the display screen at the end of the touch to distinguish between a tap and a swipe. At the end of a session, the training display 2702 may display information on makes and misses to the user, as seen in FIGS. 29A-B. The training display 2702 may display makes/misses by shot type as well as totals for all shot types. For example, training display 2702A may display makes and misses for free throws, and training display 2702B may display makes and misses for jump shots. Training display 2702B may aggregate 2 and 3 point basketball shots and may display makes and misses together, or separate displays may present makes and misses for each type of shot.

Figure 30C:
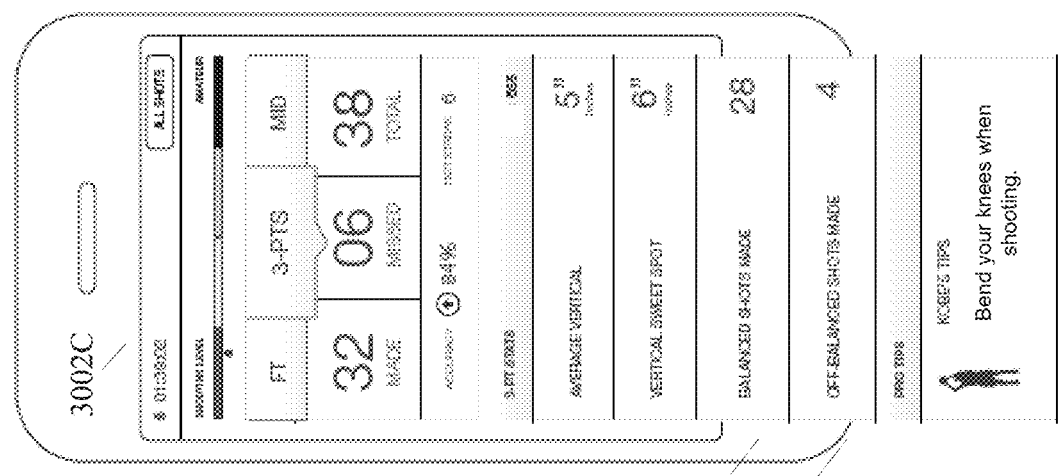
FIGS. 30A-C illustrate display screen for GUIs for a basketball shooting training session in accordance with example embodiments.
Figure 30B:
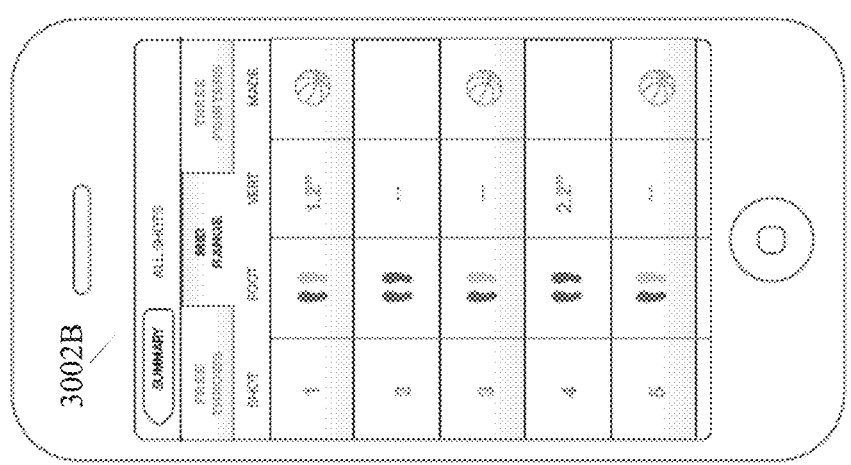
Figure 30A:
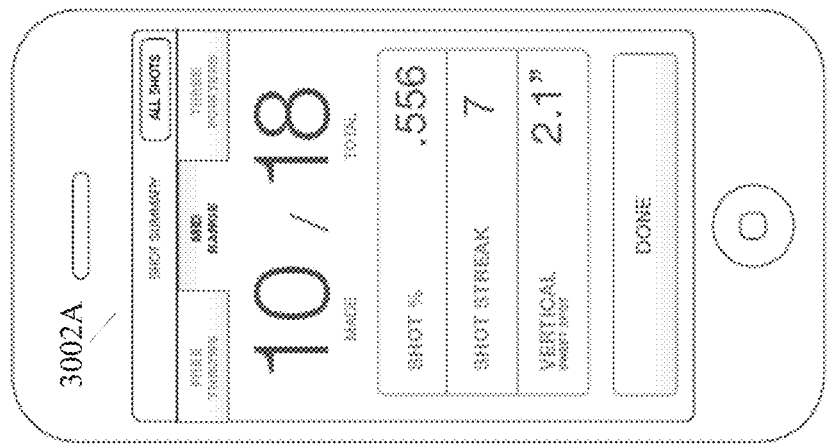

FIGS. 30A-C illustrate example displays for a GUI providing the user with information on a shooting practice session in accordance with example embodiments. Shot summary display 3002A may permit the user to select all shots or a particular shot type to receive information on percentage of shots made (e.g., 55.6%), a streak of how many shots were made consecutively, and the user's vertical leap "sweet spot" for the makes. The sweet spot may indicate a vertical leap where a user's shooting percentage (e.g., percentage of made shots) exceeds a predetermined amount (e.g., 50%). The computer 102 may process data from the pod sensor 304 and/or from distributed sensor 306 to provide the user information about their makes and misses via the GUI. This information may include on average vertical leap for makes and misses to inform the user about how jump height affects their shooting performance. Shot summary display 3002B may inform the user which foot was used when jumping as part of a shot along with a height of a vertical leap, and whether a shot was made or missed. Shot summary display 3002C may provide the user with information about three point shots made and missed.

The shot summary display 3002 may provide the user with statistic information as to how their balance affects their shots by indicating how many balanced shots were made and how many off-balanced shots were made. The computer 102 may determine balance based on weight distribution measured by distributed sensor 306 while a user took a shot. If weight is relatively evenly distributed between a user's two feet (i.e., within a certain threshold), the computer 102 may identify a shot as being balanced. When weight is not relatively evenly distributed between a user's two feet (i.e., outside of a certain threshold), the computer 102 may identify a shot as being unbalanced. The shot summary display 3002C may also provide a user with feedback about their balance and tips to correct any issues with unbalanced weight distribution. For example, field 3004 may indicate how many shots were made when a user's weight was balanced and field 3006 may indicate how many shots were made when a user's weight was off-balance.

In an example, computer 102 may receive and process data generated by a force sensor to determine a weight distribution during a performance of an exercise task (e.g., shooting a jump shot in basketball). Computer 102 may process user input indicating successful completion of an exercise task (e.g., a make). Computer 102 may associate a detected weight distribution at a time preceding the user input indicating successful completion of the exercise task. For example, computer 102 may process sensor data to identify movement consistent with a basketball shot, and determine a weight distribution starting with detecting lift-off when a user jumps during a jump shot, a period of time prior to lift-off, landing, and a period of time after landing. Computer 102 may monitor weight distribution for these periods of time. At a subsequent time (e.g., second or subsequent jump shot), computer 102 may process additional user input indicating unsuccessful completion of the exercise task (e.g., a miss). Computer 102 may associate a detected weight distribution at a time preceding the user input with the unsuccessful completion of the exercise task. After or during the exercise session, computer 102 may present to the user information about their weight distribution and about how the distribution has affected the user's ability to complete the exercise task.

Figure 31:
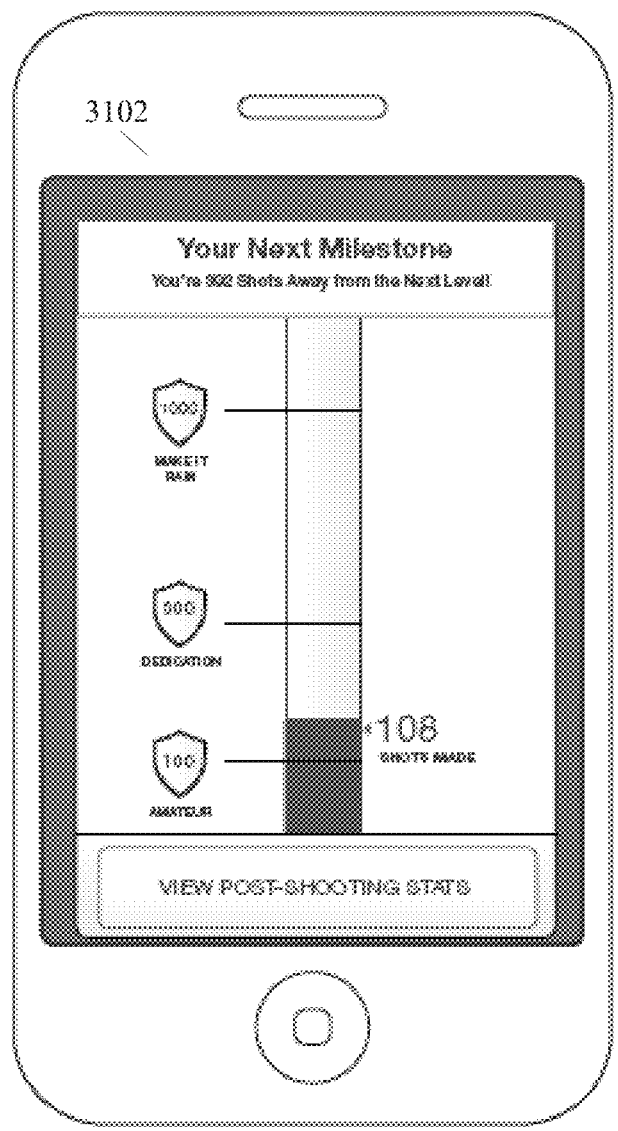
FIG. 31 illustrates an example display of a GUI informing the user of shooting milestones in accordance with example embodiments.

The GUI may also provide the user with incentives to working on their basketball shot. FIG. 31 illustrates an example display of a GUI informing the user of shooting milestones in accordance with example embodiments. Milestone display 3102 may inform the user of one or more shot thresholds and how many shots a user has made. For example, milestone display 3102 may indicate that a user has made 108 shots, such that the user has reached amateur status, and needs to make an additional 392 shots to achieve the next status level.

Figure 32C:
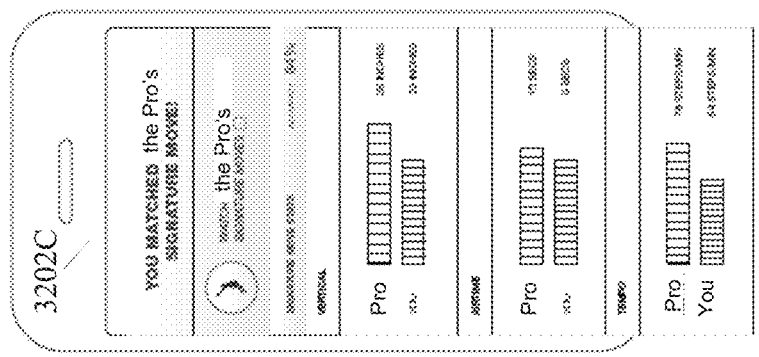
FIGS. 32A-C illustrate example signature moves displays for a GUI prompting a user to perform a drill to imitate a professional athlete's signature move in accordance with example embodiments.
Figure 32B:
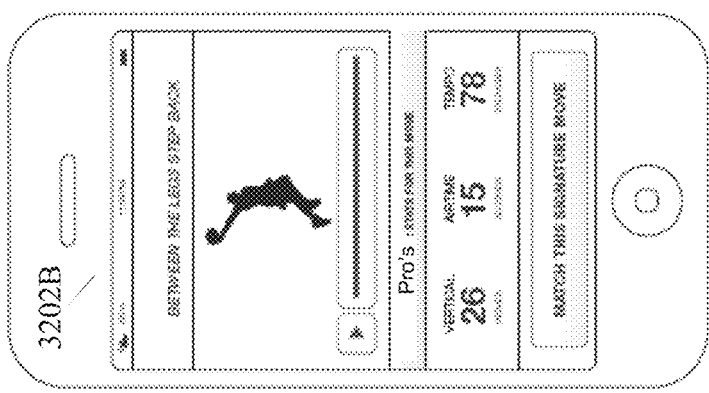
Figure 32A:
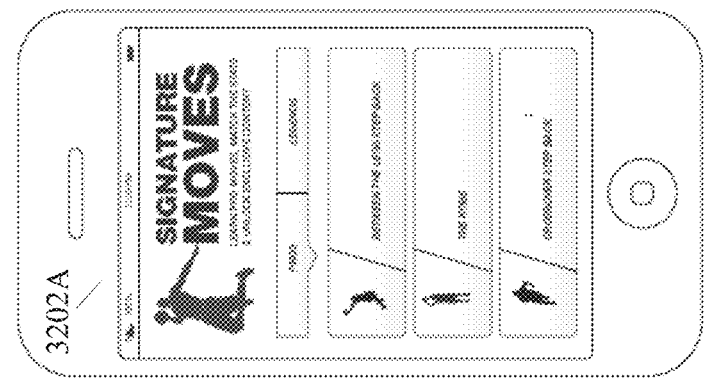

As a part of drills for enhancing a user's skills, computer 102 may prompt the user to perform moves similar to the ones used by professional athletes. FIGS. 32A-C illustrate example signature moves displays for a GUI prompting a user to perform a drill to imitate a professional athlete's signature move in accordance with example embodiments. In addition to professional athlete signature moves, users may create and share signatures moves with other users.

In an example, a user may input a search query into signature moves display 3202A to initiate a search for a desired professional athlete. The computer 102 may forward the search query to the server 134, which may reply with query results. The server 134 may also provide the computer 102 with suggested signature moves for display prior to a user inputting a search query. As seen in signature moves display 3202A, computer 102 may display different signature moves for user selection. Upon selection of a particular move, signature moves display 3202B may present video of the signature move and provide the professional's performance metrics for the move. The computer 102 may, for instance, query the server 134 for signature move data in response to the user's selection to generate signature moves display 3202B. The signature move data may include data from pod sensor 304 and distributed sensor 306 of a professional athlete performing a signature move. The user may attempt to imitate the signature move and the computer 102 may process the user data to indicate the accuracy of the imitation.

After completion of an attempt of the signature move, the computer 102 may inform the user how well they successfully imitated the move. To identify a match, the computer 102 may compare data obtained from pod sensor 304 and/or distributed sensor 306 with the signature move data to determine if the two are similar. The computer 102 may monitor how long a user took to complete the signature move, a vertical leap of the user, airtime of the user, tempo of the user, or other information and compare this data to corresponding data from the professional athlete. The computer 102 may also indicate how accurately the user imitated the signature move of the professional athlete, as shown in signature moves display 3202C. Accuracy may be based on a combination of how similar each of the performance metrics is to the professional's. The computer 102 may weight certain metrics more highly than others, or may weight each metric equally. For example, the signature move data may provide information on three different metrics, and may compare the user's data to each of the three metrics. The computer 102 may determine a ratio of the user's performance metric to the professional's metric and may identify a match if the ratio is above a threshold (e.g., more than 80%). Accuracy also may be determined in other manners.

In an example, computer 102 may receive signature move data corresponding to acceleration and force measurement data measured by a first user (e.g., a professional athlete) performing a sequence of exercise tasks (e.g., cuts in basketball followed by a dunk). Computer 102 may receive and process user data generated by at least one of sensors 304 and 306 by monitoring a second user attempting to perform the same sequence of exercise tasks. Computer 102 may then generate a similarity metric indicating how similar the user data is to the signature move data.

Figure 33C:
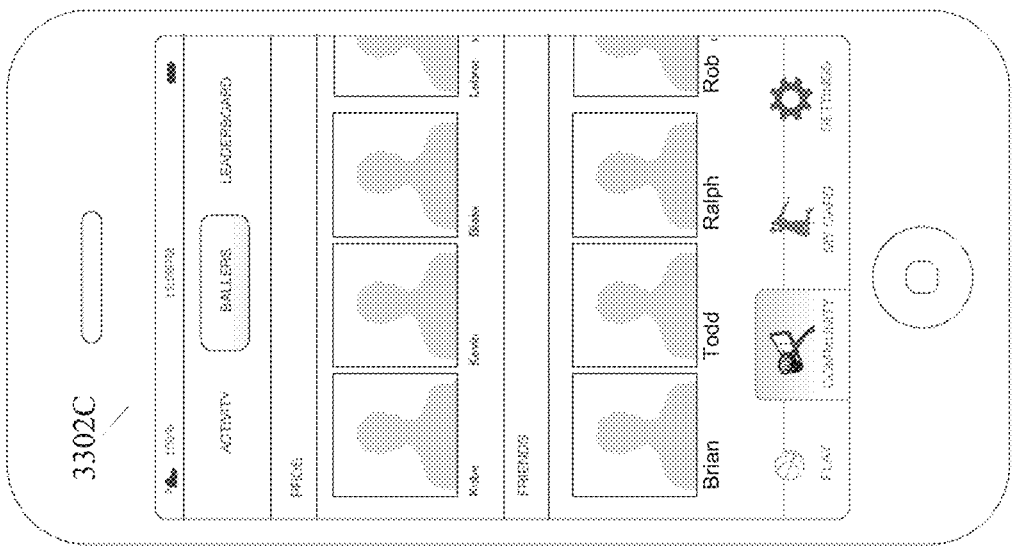
FIGS. 33A-C illustrate example displays of a GUI for searching for other users and/or professional athletes for comparison of performance metrics in accordance with example embodiments.
Figure 33B:
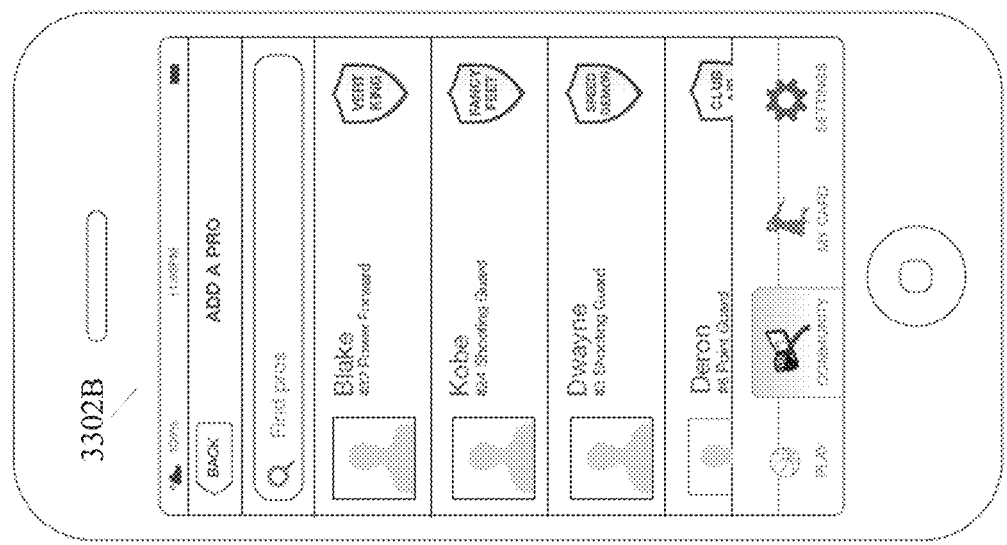
Figure 33A:
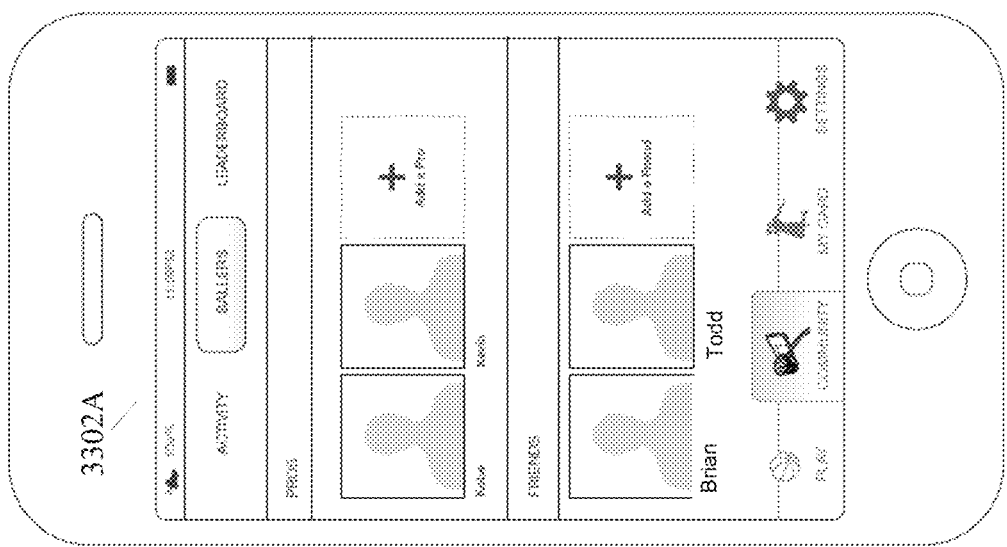

Computer 102 may also provide the user with data on performance metrics from other users and/or professional athletes for comparison as part of a social network. FIGS. 33A-C illustrates example displays of a GUI for searching for other users and/or professional athletes for comparison of performance metrics in accordance with example embodiments. Computer 102 may communicate with the server 134 to identify professional athletes or friends of the user, as seen in display 3302A. Each individual may be associated with a unique identifier. For example, the user may select to add a friend or a professional, as seen in the GUI display on the left. When a user elects to add a friend/professional, the user may input a search query into the computer 102 for communication to the server 134, which may respond with people and/or professional athletes matching the search query, as seen in display 3302B. The user may establish a user profile to identify their friends and/or favorite professional athletes so that the computer 102 may automatically load these individuals, as seen in display 3302C.

Figure 34A:
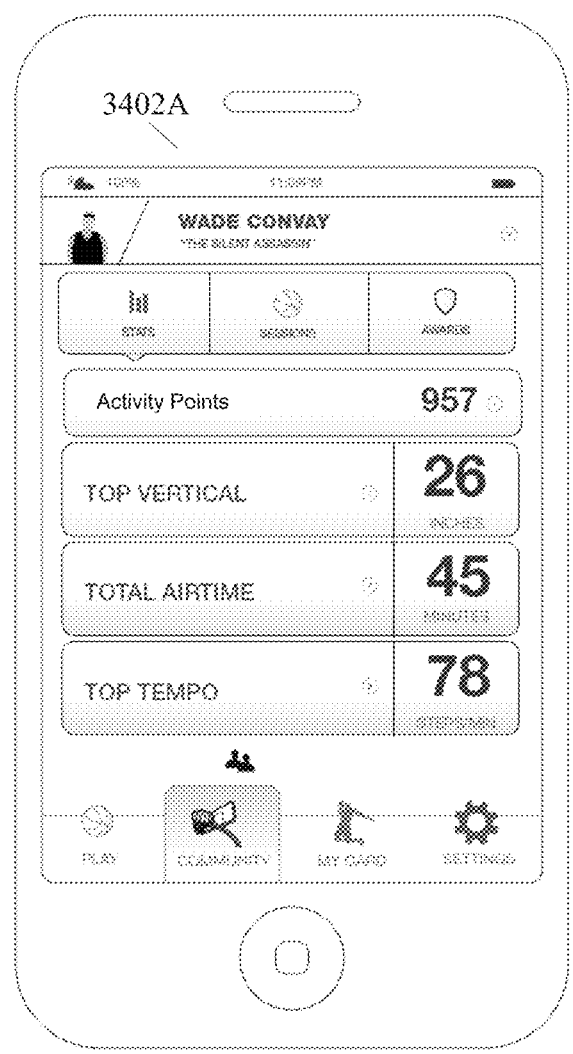
FIGS. 34A-B illustrate example displays for comparing a user's performance metrics to other individuals in accordance with example embodiments.
Figure 34B:
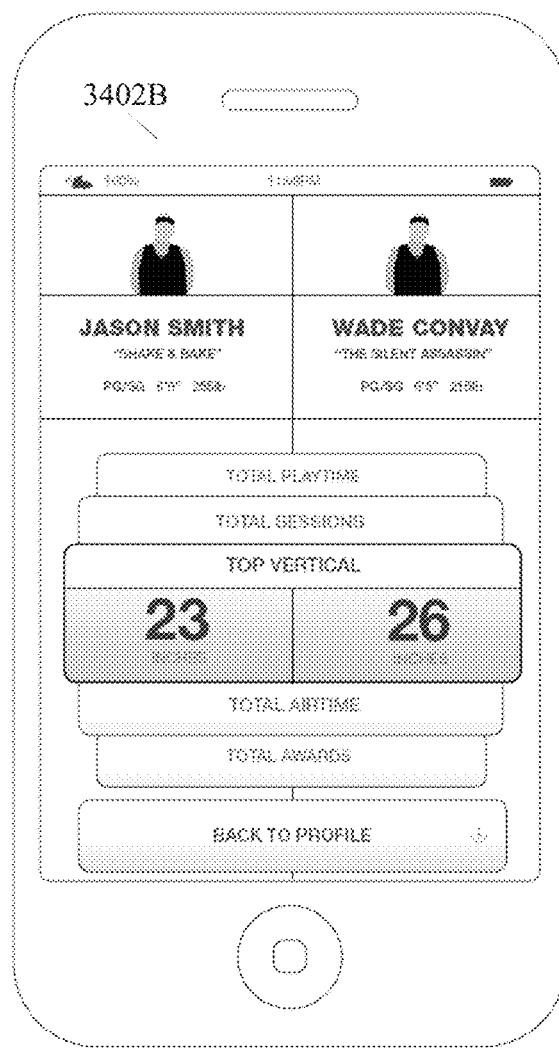

Computer 102 may present data for sharing with friends and/or posted to a social networking website. In FIG. 34A, for example, display 3402A provides information for sharing, including points, top vertical, total airtime, and top tempo. As shown in FIG. 34B, display 3402B, for instance, provides a side by side comparison of performance metrics of a user and an identified friend. In an example, the server 134 may store performance metric data on each user and may communicate the data with computer 102 of the other user upon request.

FIGS. 35A-B illustrate example displays for comparing a user's performance metrics to other individuals in accordance with example embodiments. For example, display 3502A may provide a leader board for comparison of a user's performance metric to friends, selected professional athletes, or all other users including professional athletes. Example leader boards may be for a top vertical, a top tempo, a total airtime, total games played, total awards won, or for other performance metrics. Display 3502B permits a user to view individuals whose performance metrics indicate they are in and are not in a performance zone (e.g., dunk zone). Computer 102 may also permit the user to compare their performance metrics to a particular group (e.g., friends) or to all users.

The foregoing discussion was provided primarily in relation to basketball, but the above examples may be applied to other team sports as well as individual sports.

Figure 36:
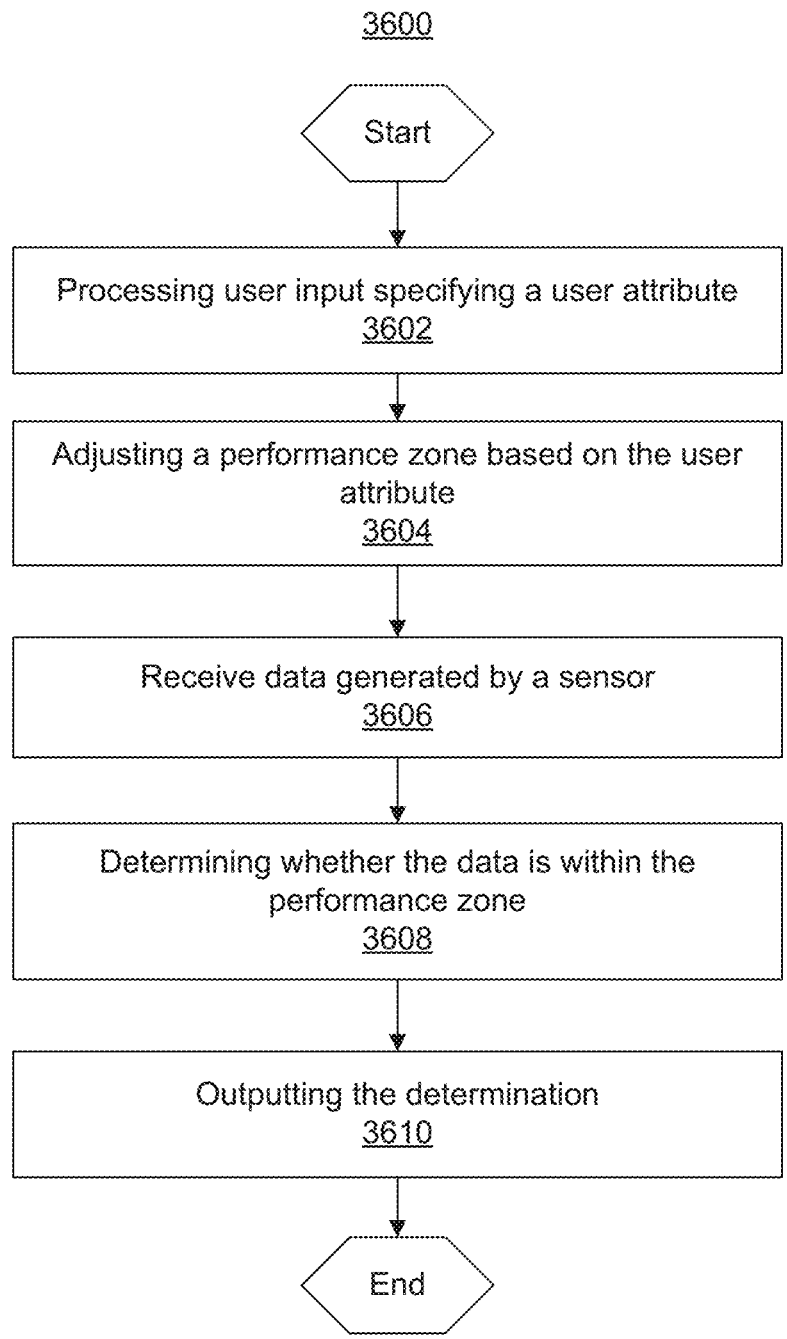
FIG. 36 illustrates a flow diagram of an example method for determining whether physical data obtained monitoring a user performing a physical activity is within a performance zone in accordance with example embodiments.

FIG. 36 illustrates a flow diagram of an example method for determining whether physical data obtained monitoring a user performing a physical activity is within a performance zone in accordance with example embodiments. The method of FIG. 36 may be implemented by a computer, such as, for example, the computer 102, server 134, a distributed computing system, a cloud computer, other apparatus, and combinations thereof. The order of the steps shown in FIG. 36 may also be rearranged, additional steps may be included, some steps may be removed, and some steps may be repeated one or more times. The method may begin at block 3602.

In block 3602, the method may include processing input specifying a user attribute. In an example, computer 102 may prompt the user to input on one or more user attributes. Example user attributes may include height, weight, arm length, torso length, leg length, wing span, etc. In an example, user may specify their body length. Body length may be a measurement of how high a user can reach one of their hands while keeping the opposite foot on the floor.

In block 3604, the method may include adjusting a performance zone based on the user attribute. In an example, computer 102 may adjust a performance zone relating to how high a user must jump to dunk a basketball based on one or more of user height, arm length, torso length, and leg length. For taller users, the performance zone may specify a lower minimum jump height to dunk a basketball as compared with a minimum jump height required for a smaller user to dunk or reach a basketball rim.

In block 3606, the method may include receiving data generated by a sensor. In an example, computer 102 may receive data from at least one of sensor 304 and 306 during an exercise session in which the user performs one or more jumps. As discussed above, the data may be raw signals or may be data processed by the sensors prior to sending to computer 102.

In block 3608, the method may include determining whether the data is within the performance zone. In an example, computer 102 may process data received from at least one of sensor 206 and 304 to determine if any jump performed by the user met or exceeded the minimum jump height of the performance zone tailored to the user's attributes. For example, computer 102 may determine that a minimum vertical leap of 30 inches would be required for a user to dunk a basketball, based on the user attributes. Computer 102 may process data received from at least one of sensor 304 and 306 to determine whether any jump performed by the user met or exceeded 30 inches. To determine a height of the vertical leap, computer 102 may process data generated by at least one of an accelerometer and a force sensor, and comparing the data to jump data to determine that the data is consistent with a jump (e.g., that a user sitting on a chair didn't merely lift their feet off of the ground for a predetermined amount of time). Computer 102 may, in response to the comparing, process data generated by at least one of an accelerometer and a force sensor to determine a lift off time, a landing time, and a loft time. Computer 102 may calculate vertical leap based on the loft time.

In block 3610, the method may include outputting the determination. In an example, computer 102 may output the determination of whether the user was within the performance zone. The output may be at least one of audible and visual. Computer 102 may provide the output immediately upon detecting the user is within the performance zone, or may output the determination at some later time (e.g., post workout). The method may then end, or may return to any of the preceding steps.

Further aspects relate to correlating image data with data relating to physical activity, such as including, but not limited to, any of the raw and/or processed data disclosed in any of the above embodiments. Data relating to physical activity (either raw or processed) may be obtained, directly or indirectly, and/or derived from one or more sensors, including those disclosed herein. In accordance with certain embodiments, physical activity data may be overlaid on an image (or sequence of images, e.g., video) of a user, such as user 124, that was captured during performance of the physical activity.

Figure 37:
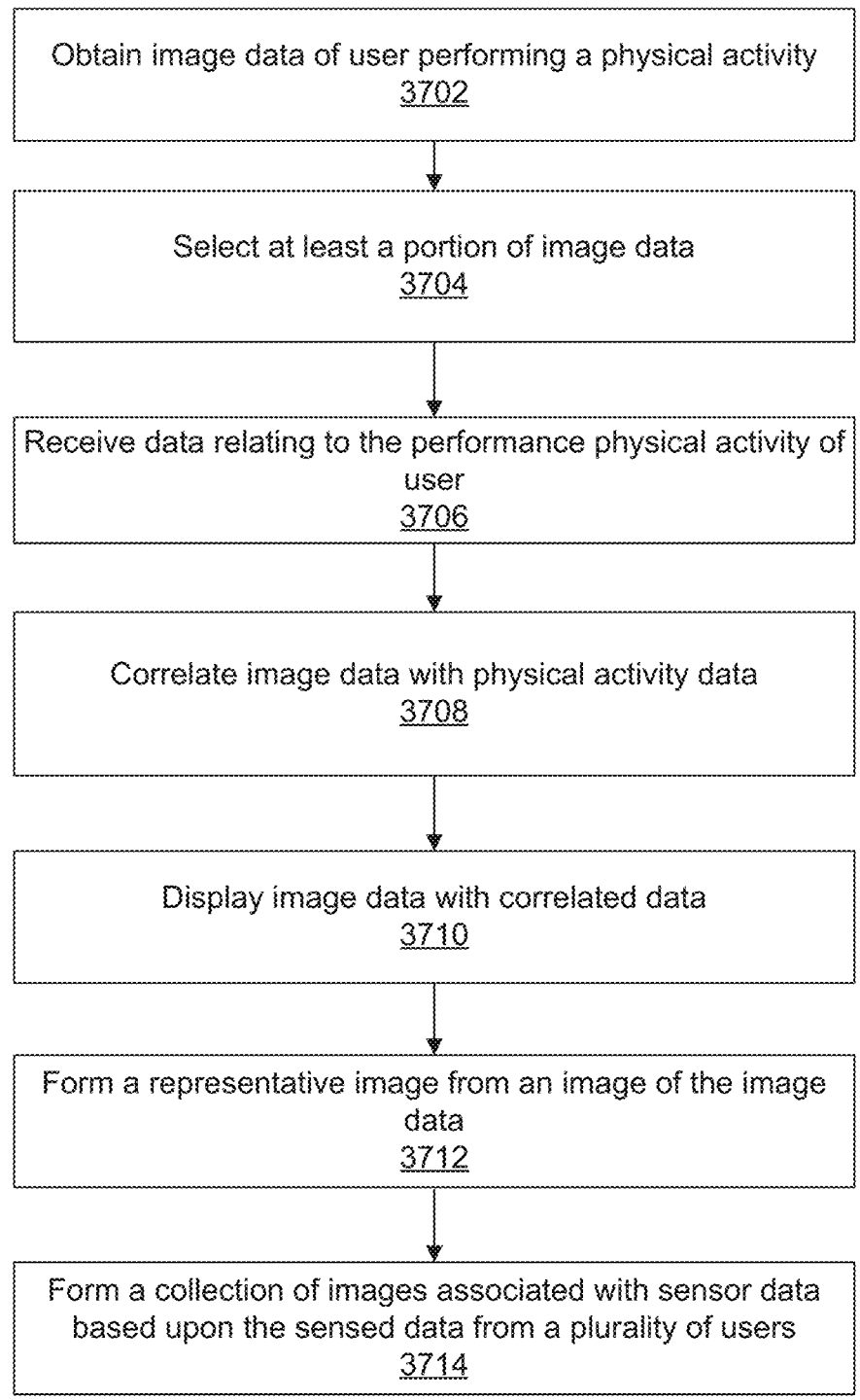
FIG. 37 illustrates a flow diagram of an example method of correlating image data and forming a collection of images that may be utilized in accordance with e embodiments.

FIG. 37 is a flowchart of an example method that may be utilized in accordance with various embodiments. At exemplary block 3702, image data may be obtained. Image data may be captured from one or more image-capturing devices, such as a camera located on a mobile terminal device (see, element 138 of FIG. 1A), a video camera, a still-image camera, and/or any apparatus configurable to detect wavelengths of energy, including light, magnetic fields, and/or thermal energy. As used herein, "image data" may encompass raw and/or compressed data, either in a physical tangible form or stored on a computer-readable medium as electronic information. Further, a plurality of images may form part of a video. Thus, references to images and/or pictures encompass videos and the like.

In one embodiment, image data, such as information obtained during the user's performance of physical activity (e.g., participating in a basketball game and/or performing a specific action, such as dunking a ball in a basket), may be captured from one or more devices. For example, a computer-readable medium may comprise computer-executable instructions that, when executed, may perform obtaining a plurality of images (e.g. a video) of the athlete playing a sport. For example, mobile terminal 138 may comprise an application that permits user 124 (or another user) to use an image capturing device (either part of the mobile terminal 138 or provide an input to an external image-capturing device, such as camera 126) to capture the image data.

In one embodiment, upon the user activating a record function (which may be a hard or soft button) on a host device (e.g., the mobile terminal 138), the simultaneous capturing of the video and physical activity sensor data may be initiated. In certain embodiments, multiple cameras may be utilized simultaneously. Multiple cameras may be used, for example, based upon the user's location, (e.g., through detection of the user by way of GPS, triangulation, or motion sensors). Image data may be obtained in response to a user operating a camera on a device, such as a camera of mobile terminal 138. In one embodiment, user 124 may provide mobile terminal 138 to another individual who can capture video of the user 124 playing a sport or performing a fitness activity. However, in further embodiments, one or more cameras may be in a fixed position, angle, focus, and/or combinations thereof. In certain embodiments, image data may be obtained from a broadcast source not directly controllable by user 124 (and/or individuals or entities under user's 124 direction), such as for example a content source provider. For example, a content source provider may broadcast (either live and/or delayed) a sporting event. In one embodiment, the event may comprise a scheduled basketball game. However in another embodiment, sporting event may comprise an unscheduled event, such as a pickup game. In certain embodiments, multiple camera feeds may be utilized to determine which feed(s) or sources of images to use.

In one embodiment, image data may only be captured based on sensor data. In one embodiment, sensor data may be physical activity data. For example, in certain implementations, image data may only be captured upon determining that user is within a "performance zone." In another embodiment, at least one physical attribute value must meet a threshold. Other embodiments may indiscriminately capture image data of user 124, and optional block 3704 or another process may be performed to select a portion of the captured image data. For example, block 3702 may capture over 20 minutes of image data of user 124, however, block 3704 may only select those portions in which the user 124 was in a performance zone. Those skilled in the art will readily appreciate that other selection criteria are within the scope of this disclosure.

The image data obtained in block 3702 (and/or selected at block 3704) may be stored on one or more non-transitory computer-readable mediums, such as on server 134, network 132, mobile terminal 138, and/or computer 102. The type and/or form of the image data may depend on a myriad of factors, including but not limited to: physical activity data (for example, as obtained from a sensor), user selection, calibration parameters, and combinations thereof. Image data may be time stamped. Time stamping of image data may be performed as part of the image data's collection and/or storage. The time stamp information may comprise a "relative" time stamp that does not depend on the actual time of capture, but rather is tied to another event, such as a data point of activity data, start time, and/or any other events. In another embodiment, an "actual" time stamp may be utilized in which the time of capture may or may not be related to another event. Those skilled in the art will appreciate that both types of stamps may be utilized, including the utilization of a single actual time stamp that is also correlated to another event.

At block 3706, physical activity data may be received. As discussed above in relation to image data, activity data may also be time stamped. In one embodiment, sensor data may be received, which may comprise raw and/or processed information relating to the user's 124 activity. Activity data may be obtained from one or more sensors described herein. For example, in one embodiment, the user's footwear may comprise at least one sensor. In certain embodiments, at least a portion of the athletic data may remain on the sensory device or another device operatively connected to the user (e.g., wrist-worn device and/or shoe-mounted sensors) until the capturing time period is over. The data may then be joined as a single file using time stamps. Certain implementations may store a single file, but transmit a first portion of the data (such as the image data) separate from a second portion (such as the activity data). In another embodiment, a first portion of data (such as the image data) may be stored separate from a second portion (such as the activity data), yet may be transmitted to a first tangible computer-readable medium as a single file.

Multiple sensors (from one or more devices) may be utilized. In one embodiment, raw accelerometer and/or gyroscope data may be obtained and processed. In another embodiment, force sensor data may be received. In yet another embodiment, physical activity parameters may be calculated based upon one or more raw parameters from a plurality of sensors. As one example, FIG. 9 shows a plurality of data parameters that may be obtained in accordance with certain implementations. In certain embodiments, user 124, the sensor data and/or sensors utilized to obtain the data (and/or the calculations for providing any processed data) may be selectable. For example, user 124 (or another input received from another source, either manually or automatically) may select a sensor 140 associated with shoes and/or other apparel. In this regard, inputs may not limited to user 124, for example, a coach, trainer, parent, friend, broadcast personnel, and/or any other individual may select one or more sources for activity data. Further embodiments may calibrate one or more sensors before utilization of corresponding data. In yet other embodiments, if calibration parameters are not obtained, data from one more sensors may be excluded from use. FIG. 10 shows an exemplary embodiment of calibration; however this disclosure is not limited to this embodiment. As discussed above in relation to image data, at least a portion of the physical activity data may be selected for processing and/or utilization.

At block 3708, image data and physical activity data may be correlated. The correlation may be based on the time stamps of the data, such that physical activity data is matched to the image data corresponding to the timing of capture. In yet other embodiments, data may be filtered, processed or otherwise adjusted to be matched with each other. For example, each image of a first video, of user 124 performing athletic activity, may represent 1/20th of a second of the first video, however, data from a first sensor may provide activity data values every 1/5th of a second, therefore, in one embodiment; four consecutive "frames" of image data during the 1/20th of a second may be associated with the sensor data captured during that 1/5 second increment. In yet other embodiments, a plurality of physical activity values may be weighted, averaged, or otherwise adjusted to be associated with a single "frame" or collective image. Correlation of the data may be implemented on one or more computer-readable mediums.

Correlation of at least a portion of the data may be implemented on a real-time basis, and/or later in time. Correlation may not occur until a selection of a portion of data is selected. In certain embodiments, the data may not be correlated until a specific user is selected. For example, image and/or physical activity data may be correlated upon the determination of a winner of a game, or upon the occurrence of an event (e.g., a user dunking a basketball). Further the type and amount of data to be correlated may also be selectable. For example, upon determining a user dunked a basketball, correlation may be performed on image and/or activity data that occurred 10 seconds prior to the dunk and continues to 3 seconds after the dunk. In one embodiment, upon determining that a player won a game or event, a larger portion of their data would be correlated. For example, data covering an entire time frame of a game or event may be utilized. Further, the data correlated may depend on the event, data collected, or other variables. For example, for a basketball dunk, activity data collected or derived from one or more force sensors within user's shoes may be utilized, yet in a soccer match, arm swing data may be utilized, alone or in combination with other data, to determine steps per second, speed, distance, or other parameters. Correlation data may include, but is not limited to: identification of the sensing unit, specific sensor, user, time stamp(s), calibration parameters, confidence values, and combinations thereof.

In further embodiments, system 100 may receive and/or process data generated by a sensor, such as a force sensor, to determine a weight distribution during a performance of an exercise task (e.g., shooting a jump shot in basketball). System 100 may associate a detected weight distribution, at a time preceding the user input, to determine an initiation point and/or cessation point for correlation of specific data. At a subsequent time, system 100 may also process additional user input indicating unsuccessful completion of the exercise task.

System 100 may process sensor data, such as for example, data received from the pod sensor 304 and/or the FSR sensor 206 over a session to determine which data may be classified and/or correlated. For example, a user's hustle during a session may be categorized into two or more categories. With reference to hustle display 1902B, system 100 may divide hustle into four categories: walking, jogging, running, and sprinting. With reference to hustle display 1902C, system 100 may divide hustle into three categories: low, medium and high. More or fewer categories of hustle may be defined. System 100 may process the data to identify a category based on a rate of steps taken by a user per interval of time (e.g., steps per minute). The correlated physical activity data may comprise information indicative of when and/or how often a user was in each category during a session. In certain embodiments, only physical activity indicative of being within one or more specific categories may be correlated with the corresponding image data.

In certain embodiments, data may be transmitted and displayed on one or more devices. In certain embodiments, the display device may be physically distinct from the device which is capturing the image(s) (see, e.g., block 3710). For example, in one embodiment, an individual may utilize a portable device, such as a mobile terminal, to capture a video of user 124 performing physical activity, such as participating in a basketball game. Information regarding the captured images may be transmitted (either before or after being correlated with data relating to the physical activity of user 124) via wired and/or wireless mediums.

FIG. 13, which was discussed above, shows an illustrative example GUI providing performance metrics during an event, game, or session in accordance with example embodiments. One or more of these metrics may relay information about a length of a current or previous session in field 1304, various performance metrics (e.g., top vertical, total airtime, tempo, etc.) for the user in field 1308, as well as who the user played with during the session in field 1310. One or more of these metrics may be overlaid with the corresponding imaging data in accordance with certain embodiments. The image data may be joined to form a video, which may be stored as a single file such that the data overlay is part of the video and is displayed with the corresponding video portion to which that data was captured. In further embodiments, a second file may store the data separate from video data.

In one embodiment, image data (and/or the physical activity) data may be transmitted in real-time. One or more images (with the corresponding activity data) may be displayed on one or more display devices, such as a display at the location of the basketball game, or any other display medium, including but not limited to being multi-casted to multiple display devices. The images (and correlated data) may be viewed via televisions, computing devices, web interfaces, and a combination thereof. In certain embodiments, user 124 and/or other individuals may selectively determine which activity data is displayed on one or more display devices. For example, a first viewer may selectively view the user's current speed and/or average speed, and a second viewer may selectively view the one or more different activity values, such as for example, highest vertical jump, number of sprints, average speed, and a combination thereof. In this regard, the data may be formed from, and/or be updated from a long duration, such as total play time during a game, portion of game (quarter, half, etc.). Thus, there is no requirement that the image data only be correlated to data obtained during capturing of the image data, but instead may further include (or be derived from) previously-obtained data. Further embodiments may present the image and/or physical activity data for sharing with friends and/or posting to a social networking website. The transmission of any data may be based on, at least in part, at least one criterion, such as for example, user-defined criteria that at least a portion of the data meets a threshold. For example, users may only want to upload their best performance(s).

Thus, certain embodiments may utilize historical data. As one example, leap data (such as that shown in leap display 1802B) may display a user's jumps chronologically over a session and may indicate a time when each jump occurred as well as vertical height for each jump during the session. The leap display 1802B may also display the user's current data and/or that user's personal best vertical leap during the event.

Further, as discussed above in relation to the correlation of data, the displaying of any data (and/or the selection of what physical activity data is displayed with the image data) may vary depending on one or more variables; including, for example, the type of game, event, user's 124 selection or input, a viewer's input, an indication that user's 124 performance has met a threshold; e.g., reached a performance zone, and/or a combination thereof. Further embodiments may determine, based on one or more computer-executable instructions on non-transitory computer readable mediums, which activity value(s) may be displayed to viewer(s) for a specific time period and the duration of displaying certain values.

In certain implementations, image data may not be correlated with at least a portion of activity data until a later time. Transmission and/or correlation of image data with activity data may be conducted on a routine basis, such as every 1 second, 10 seconds, 30 seconds, 1 minute, or any increment of time. In this regard, a system and/or user may determine to evaluate one or more metrics at a later time. These metrics may be based on, for example, a type of athletic activity performed in a session (e.g., basketball game, football game, running session, etc.). Certain embodiments may permit the evaluation and/or analysis of different metrics than initially viewed and/or desired upon capturing the image(s). For example, user 124 and/or a coach may be initially interested in evaluating a user's quantity of vertical jumps that meet a first threshold (e.g., about 4 inches), yet at a later time, the coach or user 124 may want to evaluate the image(s) with an overlay of a quantity of steps per unit time (e.g., number of steps per minute). In certain embodiments, computer 102 may prompt the user to indicate which metrics to monitor for each type of session (e.g., baseball, soccer, basketball, etc.) and store the identified metrics in a user profile. In yet another embodiment, the type of session may be derived from collected data, inclusive, but not limited to, activity data or the image data.

Computer 102 may also prompt the user for desired metrics at the beginning of each session for what data to collect—inclusive of data that may not be overlaid over the image. Further embodiments may adjust the image data collected and/or utilized. For example, variations may include the resolution, frame rate, storage format protocol, and combinations thereof. At the beginning of a session, sensors, such as sensors within a shoe (see device sensor 140) and/or other sensors, may be calibrated. Yet in other embodiments, sensors may be calibrated during, or after, a session or event. In certain embodiments, previously collected data may be utilized in determinations of whether to calibrate and/or parameters of calibration.

Block 3710 and/or other aspects of certain embodiments may relate to generating and/or displaying a summary segment with the image data. For example, the image data may be utilized to form a 25 second video. In certain embodiments, the video file may be formed to include a segment (e.g., 5 seconds), such as located at the end of the 25-seconds of image data, that provides a summary of certain statistics. In those embodiments, in which the video is a single file, this segment may also form part of the same single file. In certain embodiments, this summary screen (or another summary) may be presented to the user while the video file is being created (e.g., during the time in which the image data is being properly aligned with the sensor data). Further information may be displayed with the image data. For example, in one embodiment, an overlay may display the origination of the data; such as by a wrist-worn or shoe-mounted sensor, and/or specific manufactures or models of sensors.

Further aspects relate to creating and/or displaying a "representative image" that is formed from an image within the collection of images (see, e.g., block 3712). The representative image may be utilized as a "thumbnail" image or a cover image. In further embodiments, the representative image may be used to represent a specific video among a plurality of videos, in which each may have their own representative image. In one embodiment, the representative image may be selected based upon it being correlated in time with a data value that represents the highest value of at least one athletic parameter. For example, the highest value of a jump (e.g., vertical height) may be utilized to select an image. Yet in other embodiments, the highest value relating to velocity, acceleration, and/or other parameters may be utilized in selecting an image. Those skilled in the art will appreciate that the "best" data value may not be the highest, thus this disclosure is not limited to image data associated with the "highest" value, but rather is inclusive of any data.

In further embodiments, a user (or any individual) may select which parameter(s) are desired. In yet other embodiments, computer-executable instructions on a tangible computer-readable medium may select a parameter based upon the data collected. In yet further embodiments, a plurality of images may be selected based upon the correlated physical activity data, and allow the user to select one. Any physical activity data and/or image data may be associated with location data, such as GPS or a specific court.

Further embodiments relate to creating a collection of image data from a plurality of users, based upon sensed data (see, e.g., block 3714). In one embodiment, a "highlight reel" may be formed which comprises image data of a plurality of users. In one example, a highlight reel may be created from data obtained from a sporting event. For example, a plurality of players on one or more teams may be recorded, such as during a televised sporting event. Based upon sensed athletic data, images (e.g., video) obtained during performance of that data may be aggregated to create a highlight reel for the sporting event or a portion thereof (e.g., the first quarter and/or the final two minutes). For example, sensors may obtain athletic data from the players during the sporting event, and based upon at least one criterion (i.e., jumps higher than 24 inches and/or paces greater than 3 steps per second), correlated image data may be utilized in forming the highlight reel.

Certain embodiments relate to generating a feed or a plurality of image collections based upon at least one criterion. For example, viewers of sporting events often do not have the time to watch every game or competition, such as during playoffs of sporting events. Thus, in one embodiment, a feed may be selectively limited to physical activity of friends, teams or athletes followed, basketball games in which certain team(s) played and a specific player(s) that achieves a specific parameter value(s). Thus, in some embodiments of the invention, image data may comprise image data captured during a first time period and image data captured during a second time period that is different than the first time period. These feeds may also be categorized based upon activity type and/or sensors utilized to capture the activity. In certain embodiments, the highlight reels and/or feeds may be based, at least in part, on whether the player(s) are within a performance zone.

In one embodiment, the image data captured during the first time period is at a first geographic location and image data captured during the second time period is at a second geographic location. In certain implementations, images from two or more locations that are obtained during two different time periods, may be combined into a single image. In one embodiment, a user's physical performance may be captured with a mobile phone or other device and merged with image data corresponding to a historical athletic performance or known venue. For example, a video of a user shooting a basketball shot may be merged with a video of a famous athlete shooting a last minute three-point shot. In some embodiments, a user may capture an image of a scene prior to recording a video of a user performing an athletic move at the same location. A mobile phone, or other device, may then remove the scene data from the video to isolate the user. The isolated video of the user may then be merged with, or overlay, an image or video of another location or event. Similarly, selected portions of captured image data may be replaced. For example, a video of a user slam dunking a tennis ball may be edited to replace the tennis ball with a basketball. Various other features and devices may be used in accordance with the aspects described herein. Additional or alternative features may also be incorporated into the device and/or applications associated therewith.

CONCLUSION

While the invention has been described with respect to specific examples including presently preferred modes of carrying out the invention, those skilled in the art will appreciate that there are numerous variations and permutations of the above described systems and methods. For example, various aspects of the invention may be used in different combinations and various different sub-combinations of aspects of the invention may be used, together, in a single system or method without departing from the invention. In one example, software and applications described herein may be embodied as computer readable instructions stored in computer readable media. Also, various elements, components, and/or steps described above may be changed, changed in order, omitted, and/or additional elements, components, and/or steps may be added without departing from this invention. Thus, the invention should be construed broadly.

What is claimed is:

1. A computer-implemented method comprising:
receiving a first set of physical activity data corresponding to an athletic performance comprising at least a first activity performed by a first user, wherein the first set of physical activity data is generated by or derived from a first sensor;
capturing, by an image capturing device, image data corresponding to at least the first activity performed by the first user;
receiving, from a second user, an input identifying a first activity threshold,
determining, by a processor, whether a portion of the physical activity is indicative of the first user satisfying the first activity threshold;
correlating, in response to determining that the portion of the physical activity data indicates that the first user has satisfied the first activity threshold, the image data in accordance with the portion of the physical activity data;
overlaying, on the correlated image data, the portion of the physical activity data;
displaying, on a display device, the correlated image data with the overlaid portion of the physical activity data in real-time;
storing, as a single file, the correlated image data with the overlaid portion of the physical activity data, and
transmitting the stored correlated image data with the overlaid portion of the physical activity data to a computing device.

2. The computer-implemented method of claim 1, wherein the first activity threshold is speed or vertical jump.

3. The computer-implemented method of claim 1, wherein the image data comprises a plurality of frames, and wherein the correlating the image data further comprises:

associating a first number of frames of the image data with a corresponding time period of the first set of physical activity data.

4. The computer-implemented method of claim 1, wherein the image data comprises a plurality of frames, the computer-implemented method further comprising:
    determining, by the processor, a plurality of activity values for a first activity metric corresponding to the portion of the first set of physical activity data; and
    adjusting the plurality of activity values to be associated with at least a first frame of the image data.

5. The computer-implemented method of claim 1, further comprising:
    establishing a communication channel with the first sensor, wherein the first sensor comprises a force sensor; and
    in response to establishing the communication channel, outputting, to the display device, a communication prompting the user to perform the first activity.

6. The computer-implemented method of claim 5, further comprising:
    receiving, from the force sensor, a first set of data relating to the performance of the first activity by the first user.

7. The computer-implemented method of claim 6, wherein the first set of data further comprises at least one of: a shoe type, a shoe color, or a shoe size.

8. The computer-implemented method of claim 1, further comprising:
    receiving an input selection identifying the first user; and
    in response to receiving the input selection, initiating the correlation of the image data in accordance with the portion of the first set of physical activity data.

9. The computer-implemented method of claim 1, further comprising:
    determining, based on the portion of the first set of physical activity data, a second activity performed by the first user; and
    in response to the determining the second activity, initiating the correlation of the image data in accordance with the portion of the first set of physical activity data.

10. The computer-implemented method of claim 1, further comprising:
    receiving a second set of physical activity data corresponding to one or more previous athletic performances where the first user performed the first activity; and
    correlating the image data in accordance with the second set of physical activity data.

11. One or more non-transitory computer readable media storing instructions that, when executed by at least one processor, cause the at least one processor to:
    receive a first set of physical activity data corresponding to an athletic performance comprising at least a first activity performed by a first user, wherein the first set of physical activity data is generated by or derived from a first sensor;
    receive, from a second user, an input identifying a first activity threshold;
    capture, by an image capturing device, image data corresponding to at least the first activity performed by the user;
    determine that a portion of the physical activity data is indicative of the first user satisfying a first activity threshold;
    correlate the image data in accordance with the portion of the first set of physical activity data;
    overlay, on the correlated image data, the portion of the physical activity data;
    display, on a display device, the correlated image data with the overlaid portion of the physical activity data in real-time;
    store, as a single file, the correlated image data with the overlaid portion of the physical activity data, and
    transmit the stored correlated image data with the overlaid portion of the physical activity data to a computing device.

12. The one or more non-transitory computer readable media of claim 11, wherein the instructions, when executed, further cause the at least one processor to:
    receive a second set of physical activity data corresponding to one or more previous athletic performances where the first user performed the first activity; and
    correlate the image data in accordance with the second set of physical activity data.

13. The one or more non-transitory computer readable media of claim 11, wherein the instructions, when executed, further cause the at least one processor to:
    establish a communication channel with the first sensor, wherein the first sensor comprises a force sensor; and
    in response to establishing the communication channel, output, to thea display device, a communication prompting the first user to perform the first activity.

14. The one or more non-transitory computer readable media of claim 13, wherein the instructions, when executed, further cause the at least one processor to:
    receive, from the force sensor, a first set of data relating to the first user performing the first activity.

15. The one or more non-transitory computer readable media of claim 14, wherein the first set of data further comprises at least one of: a shoe type, a shoe color, or a shoe size.

16. The one or more non-transitory computer readable media of claim 11, wherein the instructions, when executed, further cause the at least one processor to:
    determine, based on the portion of the first set of physical activity data, a second activity performed by the first user; and
    in response to the determining the second activity, initiate the correlation of the image data in accordance with the portion of the first set of physical activity data.

17. A computer-implemented method comprising:
    receiving physical activity data corresponding to an athletic performance for a plurality of players, the physical activity data comprising data generated by or derived from a plurality of sensors;
    receiving, from a user, an input identifying a first activity threshold,
    determining, by a processor, that one or more portions of the physical activity data is indicative of one or more players, of the plurality of players, satisfying the first activity threshold;
    capturing, by an image capturing device, image data relating to the athletic performance;
    correlating the captured image data with the corresponding one or more portions of the physical activity data;
    aggregating the image data and the correlated one or more portions of the physical activity data to generate a highlight reel of the athletic performance wherein the one of more portions of the physical activity data is overlaid on the image data;
    displaying, on a display device, the highlight reel of the athletic performance wherein the one of more portions of the physical activity data is overlaid on the image data in real-time;
    storing, as a single file, the highlight reel; and
    transmitting the highlight reel to a computing device.

18. The computer-implemented method of claim 17, wherein the first activity threshold is speed or vertical jump.

19. The computer-implemented method of claim 18, wherein the image data comprises a plurality of frames, the computer-implemented method further comprising:
- determining a plurality of activity values for a first activity metric corresponding to the one or more portions of the physical activity data; and
- adjusting the plurality of activity values to be associated with at least a first frame of the image data.

20. The computer-implemented method of claim 19, wherein the image data comprises a plurality of frames, and wherein the correlating the image data further comprises:
- associating a first number of frames of the image data with a corresponding time period of a first portion, of the one or more portions, of the physical activity data.

* * * * *

UNITED STATES PATENT AND TRADEMARK OFFICE
CERTIFICATE OF CORRECTION

| | | |
|---|---|---|
| PATENT NO. | : 12,046,347 B2 | Page 1 of 1 |
| APPLICATION NO. | : 17/495071 | |
| DATED | : July 23, 2024 | |
| INVENTOR(S) | : Burroughs et al. | |

It is certified that error appears in the above-identified patent and that said Letters Patent is hereby corrected as shown below:

In the Claims

Column 38, Claim 13, Line 22:
Delete "thea" and insert --the--

Signed and Sealed this
Fifteenth Day of April, 2025

Coke Morgan Stewart
*Acting Director of the United States Patent and Trademark Office*